(12) United States Patent
Chung et al.

(10) Patent No.: US 10,378,061 B2
(45) Date of Patent: Aug. 13, 2019

(54) BIOMARKER FOR PREDICTING EFFECT OF AN ANTI-C-MET ANTIBODY

(71) Applicant: Samsung Electronics Co., Ltd., Suwon-si, Gyeonggi-do (KR)

(72) Inventors: Jongsuk Chung, Hwaseong-si (KR); Tae Jin Ahn, Seoul (KR); Dae-Soon Son, Seoul (KR); Eunjin Lee, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 183 days.

(21) Appl. No.: 14/678,108

(22) Filed: Apr. 3, 2015

(65) Prior Publication Data
US 2015/0284808 A1    Oct. 8, 2015

(30) Foreign Application Priority Data

Apr. 3, 2014 (KR) .................. 10-2014-0040146
Apr. 1, 2015 (KR) .................. 10-2015-0046413

(51) Int. Cl.
*C12Q 1/68*       (2018.01)
*C12P 19/34*      (2006.01)
*C12Q 1/6886*     (2018.01)

(52) U.S. Cl.
CPC ..... *C12Q 1/6886* (2013.01); *C12Q 2600/106* (2013.01); *C12Q 2600/158* (2013.01); *C12Q 2600/16* (2013.01); *C12Q 2600/166* (2013.01)

(58) Field of Classification Search
CPC ............ C12Q 1/6886; C12Q 2600/106; C12Q 2600/158
See application file for complete search history.

(56) References Cited

U.S. PATENT DOCUMENTS

| | | | |
|---|---|---|---|
| 8,563,696 B2 | 10/2013 | Cheong et al. | |
| 2011/0262436 A1 | 10/2011 | Bender et al. | |
| 2013/0018024 A1 | 1/2013 | Bianchi et al. | |
| 2013/0089557 A1* | 4/2013 | Cheong .............. | C07K 16/2863 424/138.1 |
| 2014/0024548 A1 | 1/2014 | Singh et al. | |

FOREIGN PATENT DOCUMENTS

| | | |
|---|---|---|
| CN | 102216331 A | 10/2011 |
| CN | 103384828 A | 11/2012 |
| KR | 20110047698 A | 5/2011 |
| WO | WO 2010/045345 A2 | 4/2010 |
| WO | WO 2011/048033 A2 | 4/2011 |
| WO | WO 2012/088337 A1 | 6/2012 |

OTHER PUBLICATIONS

Michael J. Boedigheimer et al., Neoplasia, vol. 15, Issue 2, Feb. 2013, pp. 125-132.*
Peter C. Huszthy et al., Neuro Oncol. Aug. 2012; 14(8): 979-993.*
Morgan, R.A. Moelcular Therapy, vol. 20, No. 5, May 2012, p. 882-884.*
Choi, S.Y.C. et al., Advanced Drug Delivery Reviews, vols. 79-80, Dec. 15, 2014, pp. 222-237.*
Yedavalli, V.S.R.K. et al., Retrovirology 2011 8:61.*
Chen G. et al., Molecular & Cellular Proteomics 1:304-313, 2002.*
Cheung V.G. et al., Nature Genetics, (2003) vol. 33, p. 422-425.*
Hoshikawa Y. et al., Physiol Genomics 12: 209-219, 2003.*
Cobb J.P. et al., Crit Care Med 2002 vol. 30, No. 12, p. 2711-2721.*
Affymetrix Show Results for a search of THSD7A in the U95 arrays, 2 printed pages from www.affymetrix.com/analysis/netaffx, May 11, 2018 (Year: 2018).*
Affymetrix Show Results for a search of MATR3in the U95 arrays, 2 printed pages from www.affymetrix.com/analysis/netaffx, May 11, 2018 (Year: 2018).*
Kuo et al., Soluble THSD7A Is an N-Glycoprotein That Promotes Endothelial Cell Migration and Tube Formation in Angiogenesis, *PLoS ONE*, 6(12): 1-12 (2011).
Torti et al., A preclinical algorithm of soluble surrogate biomarkers that correlate with therapeutic inhibition of the MET oncogene in gastric tumors, *International Journal of Cancer*, 130(6): 1357-1366 (2012).
European Patent Office, partial European Search Report in Application No. 15162330.3 dated Sep. 7, 2015, 8pgs.
Patent Office of the People's Republic of China, First Office Action in Application No. 201510156233.5, dated Oct. 10, 2017, 5 pages.

* cited by examiner

*Primary Examiner* — Stephen T Kapushoc
(74) *Attorney, Agent, or Firm* — Leydig, Voit & Mayer, Ltd.

(57) ABSTRACT

A method of predicting an effect of an anti-c-Met antibody and/or selecting a subject for application of an anti-c-Met antibody including measuring a level of the biomarker in a biological sample, is provided.

24 Claims, 6 Drawing Sheets
Specification includes a Sequence Listing.

Non-responding (non-efficacy) sample

LXFA 297 (score : 2-3)   LXFA 983 (score : 2-3)   LXFA 1041 (score : 3)

LXFA 623 (score : 3)   LXFA 526 (score : 3)   LXFA 1647 (score : 3)

Responding (Efficacy) sample

SEQUENCE LISTING

```
<160> NUMBER OF SEQ ID NOS: 306

<210> SEQ ID NO 1
<211> LENGTH: 5
<212> TYPE: PRT
<213> ORGANISM: Artificial Sequence
<220> FEATURE:
<223> OTHER INFORMATION: Synthetic heavy chain CDR1 of AbF46

<400> SEQUENCE: 1

Asp Tyr Tyr Met Ser
 1               5

<210> SEQ ID NO 2
<211> LENGTH: 19
<212> TYPE: PRT
<213> ORGANISM: Artificial Sequence
<220> FEATURE:
<223> OTHER INFORMATION: Synthetic heavy chain CDR2 of AbF46

<400> SEQUENCE: 2

Phe Ile Arg Asn Lys Ala Asn Gly Tyr Thr Thr Glu Tyr Ser Ala Ser
 1               5                  10                  15

Val Lys Gly

<210> SEQ ID NO 3
<211> LENGTH: 6
<212> TYPE: PRT
<213> ORGANISM: Artificial Sequence
<220> FEATURE:
<223> OTHER INFORMATION: Synthetic heavy chain CDR3 of AbF46

<400> SEQUENCE: 3

Asp Asn Trp Phe Ala Tyr
 1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic heavy chain CDR1 of c-Met antibody
<220> FEATURE:
<221> NAME/KEY: MOD_RES
<222> LOCATION: (1)
<223> OTHER INFORMATION: Xaa is Pro or Ser or absent
<220> FEATURE:
<221> NAME/KEY: MOD_RES
<222> LOCATION: (2)
<223> OTHER INFORMATION: Xaa is Glu or Asp
```

```
<400> SEQUENCE: 4

Xaa Xaa Tyr Tyr Met Ser
  1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic heavy chain CDR2 of c-Met antibody
<220> FEATURE:
<221> NAME/KEY: MOD_RES
<222> LOCATION: (3)
<223> OTHER INFORMATION: X is Asn or Lys
<220> FEATURE:
<221> NAME/KEY: MOD_RES
<222> LOCATION: (4)
<223> OTHER INFORMATION: Xaa is Ala or Val
<220> FEATURE:
<221> NAME/KEY: MOD_RES
<222> LOCATION: (7)
<223> OTHER INFORMATION: Xaa is Asn or Thr

<400> SEQUENCE: 5

Arg Asn Xaa Xaa Asn Gly Xaa Thr
  1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic heavy chain CDR3 of c-Met antibody
<220> FEATURE:
<221> NAME/KEY: MOD_RES
<222> LOCATION: (5)
<223> OTHER INFORMATION: Xaa is Ser or Thr

<400> SEQUENCE: 6

Asp Asn Trp Leu Xaa Tyr
  1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic light chain CDR1 of c-Met antibody
<220> FEATURE:
<221> NAME/KEY: MOD_RES
<222> LOCATION: (4)
<223> OTHER INFORMATION: Xaa is His, Arg, Gln or Lys
<220> FEATURE:
<221> NAME/KEY: MOD_RES
<222> LOCATION: (9)
<223> OTHER INFORMATION: Xaa is Ser or Trp
<220> FEATURE:
<221> NAME/KEY: MOD_RES
<222> LOCATION: (12)
<223> OTHER INFORMATION: Xaa is His or Gln
<220> FEATURE:
<221> NAME/KEY: MOD_RES
<222> LOCATION: (13)
<223> OTHER INFORMATION: Xaa is Lys or Asn

<400> SEQUENCE: 7

Lys Ser Ser Xaa Ser Leu Leu Ala Xaa Gly Asn Xaa Xaa Asn Tyr Leu
  1               5                  10                  15

Ala
```

```
<210> SEQ ID NO 8
<211> LENGTH: 7
<212> TYPE: PRT
<213> ORGANISM: Artificial Sequence
<220> FEATURE:
<223> OTHER INFORMATION: Synthetic light chain CDR2 of c-Met antibody
<220> FEATURE:
<221> NAME/KEY: MOD_RES
<222> LOCATION: (2)
<223> OTHER INFORMATION: Xaa is Ala or Gly
<220> FEATURE:
<221> NAME/KEY: MOD_RES
<222> LOCATION: (4)
<223> OTHER INFORMATION: Xaa is Thr or Lys
<220> FEATURE:
<221> NAME/KEY: MOD_RES
<222> LOCATION: (7)
<223> OTHER INFORMATION: Xaa is Ser or Pro

<400> SEQUENCE: 8

Trp Xaa Ser Xaa Arg Val Xaa
  1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic light chain CDR3 of c-Met antibody
<220> FEATURE:
<221> NAME/KEY: MOD_RES
<222> LOCATION: (1)
<223> OTHER INFORMATION: Xaa is Gly, Ala or Gln
<220> FEATURE:
<221> NAME/KEY: MOD_RES
<222> LOCATION: (6)
<223> OTHER INFORMATION: Xaa is Arg, His, Ser, Ala, Gly or Lys
<220> FEATURE:
<221> NAME/KEY: MOD_RES
<222> LOCATION: (8)
<223> OTHER INFORMATION: Xaa is Leu, Tyr, Phe or Met

<400> SEQUENCE: 9

Xaa Gln Ser Tyr Ser Xaa Pro Xaa Thr
  1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic light chain CDR1 of AbF46

<400> SEQUENCE: 10

Lys Ser Ser Gln Ser Leu Leu Ala Ser Gly Asn Gln Asn Asn Tyr Leu
  1               5                  10                  15

Ala

<210> SEQ ID NO 11
<211> LENGTH: 7
<212> TYPE: PRT
<213> ORGANISM: Artificial Sequence
<220> FEATURE:
<223> OTHER INFORMATION: Synthetic light chain CDR2 of AbF46

<400> SEQUENCE: 11

Trp Ala Ser Thr Arg Val Ser
  1               5
```

```
<210> SEQ ID NO 12
<211> LENGTH: 9
<212> TYPE: PRT
<213> ORGANISM: Artificial Sequence
<220> FEATURE:
<223> OTHER INFORMATION: Synthetic light chain CDR3 of AbF46

<400> SEQUENCE: 12

Gln Gln Ser Tyr Ser Ala Pro Leu Thr
 1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic CDR-L3 derived from L3-1 clone

<400> SEQUENCE: 13

Gln Gln Ser Tyr Ser Arg Pro Tyr Thr
 1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic CDR-L3 derived from L3-2 clone

<400> SEQUENCE: 14

Gly Gln Ser Tyr Ser Arg Pro Leu Thr
 1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic CDR-L3 derived from L3-3 clone

<400> SEQUENCE: 15

Ala Gln Ser Tyr Ser His Pro Phe Ser
 1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic CDR-L3 derived from L3-5 clone

<400> SEQUENCE: 16

Gln Gln Ser Tyr Ser Arg Pro Phe Thr
 1               5

<210> SEQ ID NO 17
<211> LENGTH: 117
<212> TYPE: PRT
<213> ORGANISM: Artificial Sequence
<220> FEATURE:
<223> OTHER INFORMATION: Synthetic heavy chain variable region of anti
      c-Met humanized antibody(huAbF46-H4)

<400> SEQUENCE: 17

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
```

```
            20                  25                  30
Tyr Met Ser Trp Val Arg Gln Ala Pro Gly Lys Gly Leu Glu Trp Leu
        35                  40                  45
Gly Phe Ile Arg Asn Lys Ala Asn Gly Tyr Thr Thr Glu Tyr Ser Ala
    50                  55                  60
Ser Val Lys Gly Arg Phe Thr Ile Ser Arg Asp Asn Ser Lys Asn Thr
65                  70                  75                  80
Leu Tyr Leu Gln Met Asn Ser Leu Arg Ala Glu Asp Thr Ala Val Tyr
                85                  90                  95
Tyr Cys Ala Arg Asp Asn Trp Phe Ala Tyr Trp Gly Gln Gly Thr Leu
            100                 105                 110
Val Thr Val Ser Ser
        115

<210> SEQ ID NO 18
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 18

Asp Ile Gln Met Thr Gln Ser Pro Ser Ser Leu Ser Ala Ser Val Gly
1               5                   10                  15
Asp Arg Val Thr Ile Thr Cys Lys Ser Ser Gln Ser Leu Leu Ala Ser
            20                  25                  30
Gly Asn Gln Asn Asn Tyr Leu Ala Trp His Gln Gln Lys Pro Gly Lys
        35                  40                  45
Ala Pro Lys Met Leu Ile Ile Trp Ala Ser Thr Arg Val Ser Gly Val
    50                  55                  60
Pro Ser Arg Phe Ser Gly Ser Gly Ser Gly Thr Asp Phe Thr Leu Thr
65                  70                  75                  80
Ile Ser Ser Leu Gln Pro Glu Asp Phe Ala Thr Tyr Tyr Cys Gln Gln
                85                  90                  95
Ser Tyr Ser Arg Pro Tyr Thr Phe Gly Gln Gly Thr Lys Val Glu Ile
            100                 105                 110
Lys Arg

<210> SEQ ID NO 19
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 19

Asp Ile Gln Met Thr Gln Ser Pro Ser Ser Leu Ser Ala Ser Val Gly
1               5                   10                  15
Asp Arg Val Thr Ile Thr Cys Lys Ser Ser Gln Ser Leu Leu Ala Ser
            20                  25                  30
Gly Asn Gln Asn Asn Tyr Leu Ala Trp His Gln Gln Lys Pro Gly Lys
        35                  40                  45
Ala Pro Lys Met Leu Ile Ile Trp Ala Ser Thr Arg Val Ser Gly Val
    50                  55                  60
Pro Ser Arg Phe Ser Gly Ser Gly Ser Gly Thr Asp Phe Thr Leu Thr
65                  70                  75                  80
```

```
Ile Ser Ser Leu Gln Pro Glu Asp Phe Ala Thr Tyr Tyr Cys Gly Gln
            85                  90                  95

Ser Tyr Ser Arg Pro Leu Thr Phe Gly Gln Gly Thr Lys Val Glu Ile
            100                 105                 110

Lys Arg

<210> SEQ ID NO 20
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 20

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Ala Gln
            85                  90                  95

Ser Tyr Ser His Pro Phe Ser Phe Gly Gln Gly Thr Lys Val Glu Ile
            100                 105                 110

Lys Arg

<210> SEQ ID NO 21
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 21

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
            85                  90                  95

Ser Tyr Ser Arg Pro Phe Thr Phe Gly Gln Gly Thr Lys Val Glu Ile
            100                 105                 110

Lys Arg

<210> SEQ ID NO 22
```

```
<211> LENGTH: 6
<212> TYPE: PRT
<213> ORGANISM: Artificial Sequence
<220> FEATURE:
<223> OTHER INFORMATION: Synthetic CDR-H1 derived from H11-4 clone

<400> SEQUENCE: 22

Pro Glu Tyr Tyr Met Ser
 1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic CDR-H1 derived from YC151 clone

<400> SEQUENCE: 23

Pro Asp Tyr Tyr Met Ser
 1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic CDR-H1 derived from YC193 clone

<400> SEQUENCE: 24

Ser Asp Tyr Tyr Met Ser
 1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic CDR-H2 derived from YC244 clone

<400> SEQUENCE: 25

Arg Asn Asn Ala Asn Gly Asn Thr
 1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic CDR-H2 derived from YC321 clone

<400> SEQUENCE: 26

Arg Asn Lys Val Asn Gly Tyr Thr
 1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic CDR-H3 derived from YC354 clone

<400> SEQUENCE: 27

Asp Asn Trp Leu Ser Tyr
 1               5

<210> SEQ ID NO 28
<211> LENGTH: 6
```

```
<212> TYPE: PRT
<213> ORGANISM: Artificial Sequence
<220> FEATURE:
<223> OTHER INFORMATION: Synthetic CDR-H3 derived from YC374 clone

<400> SEQUENCE: 28

Asp Asn Trp Leu Thr Tyr
 1               5

<210> SEQ ID NO 29
<211> LENGTH: 17
<212> TYPE: PRT
<213> ORGANISM: Artificial Sequence
<220> FEATURE:
<223> OTHER INFORMATION: Synthetic CDR-L1 derived from L1-1 clone

<400> SEQUENCE: 29

Lys Ser Ser His Ser Leu Leu Ala Ser Gly Asn Gln Asn Asn Tyr Leu
 1               5                  10                  15

Ala

<210> SEQ ID NO 30
<211> LENGTH: 17
<212> TYPE: PRT
<213> ORGANISM: Artificial Sequence
<220> FEATURE:
<223> OTHER INFORMATION: Synthetic CDR-L1 derived from L1-3 clone

<400> SEQUENCE: 30

Lys Ser Ser Arg Ser Leu Leu Ser Ser Gly Asn His Lys Asn Tyr Leu
 1               5                  10                  15

Ala

<210> SEQ ID NO 31
<211> LENGTH: 17
<212> TYPE: PRT
<213> ORGANISM: Artificial Sequence
<220> FEATURE:
<223> OTHER INFORMATION: Synthetic CDR-L1 derived from L1-4 clone

<400> SEQUENCE: 31

Lys Ser Ser Lys Ser Leu Leu Ala Ser Gly Asn Gln Asn Asn Tyr Leu
 1               5                  10                  15

Ala

<210> SEQ ID NO 32
<211> LENGTH: 17
<212> TYPE: PRT
<213> ORGANISM: Artificial Sequence
<220> FEATURE:
<223> OTHER INFORMATION: Synthetic CDR-L1 derived from L1-12 clone

<400> SEQUENCE: 32

Lys Ser Ser Arg Ser Leu Leu Ala Ser Gly Asn Gln Asn Asn Tyr Leu
 1               5                  10                  15

Ala

<210> SEQ ID NO 33
<211> LENGTH: 17
<212> TYPE: PRT
<213> ORGANISM: Artificial Sequence
<220> FEATURE:
<223> OTHER INFORMATION: Synthetic CDR-L1 derived from L1-22 clone

<400> SEQUENCE: 33
```

Lys Ser Ser His Ser Leu Leu Ala Ser Gly Asn Gln Asn Asn Tyr Leu
1               5                   10                  15

Ala

<210> SEQ ID NO 34
<211> LENGTH: 7
<212> TYPE: PRT
<213> ORGANISM: Artificial Sequence
<220> FEATURE:
<223> OTHER INFORMATION: Synthetic CDR-L2 derived from L2-9 clone

<400> SEQUENCE: 34

Trp Ala Ser Lys Arg Val Ser
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic CDR-L2 derived from L2-12 clone

<400> SEQUENCE: 35

Trp Gly Ser Thr Arg Val Ser
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic CDR-L2 derived from L2-16 clone

<400> SEQUENCE: 36

Trp Gly Ser Thr Arg Val Pro
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic CDR-L3 derived from L3-32 clone

<400> SEQUENCE: 37

Gln Gln Ser Tyr Ser Lys Pro Phe Thr
1               5

<210> SEQ ID NO 38
<211> LENGTH: 1416
<212> TYPE: DNA
<213> ORGANISM: Artificial Sequence
<220> FEATURE:
<223> OTHER INFORMATION: Synthetic nucleotide sequence of heavy chain of
      chAbF46
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:

```
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 38
gaattcgccg ccaccatgga atggagctgg gttttctcg taacactttt aaatggtatc        60
cagtgtgagg tgaagctggt ggagtctgga ggaggcttgg tacagcctgg gggttctctg      120
agactctcct gtgcaacttc tgggttcacc ttcactgatt actacatgag ctgggtccgc      180
cagcctccag gaaaggcact gagtggttg gttttatta gaaacaaagc taatggttac       240
acaacagagt acagtgcatc tgtgaagggt cggttcacca tctccagaga taattcccaa      300
agcatcctct atcttcaaat ggacaccctg agagctgagg acagtgccac ttattactgt      360
gcaagagata actggtttgc ttactggggc caagggactc tggtcactgt ctctgcagct      420
agcaccaagg gcccatcggt cttccccctg gcaccctcct ccaagagcac ctctgggggc      480
acagcggccc tgggctgcct ggtcaaggac tacttccccg aaccggtgac ggtgtcgtgg      540
aactcaggcg ccctgaccag cggcgtgcac accttcccgg ctgtcctaca gtcctcagga      600
ctctactccc tcagcagcgt ggtgaccgtg ccctccagca gcttgggcac ccagacctac      660
atctgcaacg tgaatcacaa gcccagcaac accaaggtgg acaagaaagt tgagcccaaa      720
tcttgtgaca aaactcacac atgcccaccg tgcccagcac ctgaactcct ggggggaccg      780
tcagtcttcc tcttccccccc aaaacccaag gacaccctca tgatctcccg gacccctgag      840
gtcacatgcg tggtggtgga cgtgagccac gaagaccctg aggtcaagtt caactggtac      900
gtggacggcg tggaggtgca taatgccaag acaaagccgc gggaggagca gtacaacagc      960
acgtaccgtg tggtcagcgt cctcaccgtc ctgcaccagg actggctgaa tggcaaggag     1020
tacaagtgca aggtctccaa caaagccctc ccagccccca tcgagaaaac catctccaaa     1080
gccaaagggc agccccgaga accacaggtg tacaccctgc ccccatcccg ggaggagatg     1140
accaagaacc aggtcagcct gacctgcctg gtcaaaggct tctatcccag cgacatcgcc     1200
gtggagtggg agagcaatgg gcagccggag aacaactaca agaccacgcc tcccgtgctg     1260
gactccgacg gctccttctt cctctacagc aagctcaccg tggacaagag caggtggcag     1320
caggggaacg tcttctcatg ctccgtgatg catgaggctc tgcacaacca ctacacgcag     1380
aagagcctct ccctgtctcc gggtaaatga ctcgag                               1416

<210> SEQ ID NO 39
<211> LENGTH: 759
<212> TYPE: DNA
<213> ORGANISM: Artificial Sequence
<220> FEATURE:
<223> OTHER INFORMATION: Synthetic nucleotide sequence of light chain of
      chAbF46
<220> FEATURE:
<221> NAME/KEY: misc_difference
<222> LOCATION: (1)..(6)
<223> OTHER INFORMATION: EcoRI restriction site
<220> FEATURE:
```

```
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 39
gaattcacta gtgattaatt cgccgccacc atggattcac aggcccaggt cctcatgttg      60
ctgctgctat cggtatctgg tacctgtgga gacattttga tgacccagtc tccatcctcc     120
ctgactgtgt cagcaggaga aaggtcact atgagctgca agtccagtca gagtctttta     180
gctagtggca accaaaataa ctacttggcc tggcaccagc agaaaccagg acgatctcct     240
aaaatgctga taatttgggc atccactagg gtatctggag tccctgatcg cttcataggc     300
agtggatctg ggacggattt cactctgacc atcaacagtg tgcaggctga agatctggct     360
gtttattact gtcagcagtc ctacagcgct ccgctcacgt tcggtgctgg gaccaagctg     420
gagctgaaac gtacggtggc tgcaccatct gtcttcatct tcccgccatc tgatgagcag     480
ttgaaatctg gaactgcctc tgttgtgtgc ctgctgaata acttctatcc cagagaggcc     540
aaagtacagt ggaaggtgga taacgcccte caatcgggta actcccagga gagtgtcaca     600
gagcaggaca gcaaggacag cacctacagc ctcagcagca ccctgacgct gagcaaagca     660
gactacgaga aacacaaagt ctacgcctgc gaagtcaccc atcagggcct gagctcgccc     720
gtcacaaaga gcttcaacag gggagagtgt tgactcgag                            759

<210> SEQ ID NO 40
<211> LENGTH: 447
<212> TYPE: PRT
<213> ORGANISM: Artificial Sequence
<220> FEATURE:
<223> OTHER INFORMATION: Synthetic amino acid sequence of H1-heavy

<400> SEQUENCE: 40

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Tyr
             20                  25                  30

Tyr Met Ser Trp Val Arg Gln Ala Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Ser
 65                  70                  75                  80

Leu Tyr Leu Gln Met Asn Ser Leu Lys Thr Glu Asp Thr Ala Val Tyr
                 85                  90                  95
```

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 41
<211> LENGTH: 447
<212> TYPE: PRT
<213> ORGANISM: Artificial Sequence
<220> FEATURE:
<223> OTHER INFORMATION: Synthetic amino acid sequence of H3-heavy

<400> SEQUENCE: 41

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430
```

His Asn His Tyr Thr Gln Lys Ser Leu Ser Leu Ser Pro Gly Lys
            435                 440                 445

<210> SEQ ID NO 42
<211> LENGTH: 447
<212> TYPE: PRT
<213> ORGANISM: Artificial Sequence
<220> FEATURE:
<223> OTHER INFORMATION: Synthetic amino acid sequence of H4-heavy

<400> SEQUENCE: 42

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

```
Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445
```

<210> SEQ ID NO 43
<211> LENGTH: 220
<212> TYPE: PRT
<213> ORGANISM: Artificial Sequence
<220> FEATURE:
<223> OTHER INFORMATION: Synthetic amino acid sequence of H1-light

<400> SEQUENCE: 43

```
Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Leu Leu Ala Ser
             20                  25                  30

Gly Asn Gln Asn Asn Tyr Leu Ala Trp His Gln Gln Lys Pro Gly Gln
         35                  40                  45

Pro Pro Lys Met Leu Ile Ile Trp Ala Ser Thr Arg Val Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 44
<211> LENGTH: 220
<212> TYPE: PRT
<213> ORGANISM: Artificial Sequence
<220> FEATURE:
<223> OTHER INFORMATION: Synthetic amino acid sequence of H2-light

<400> SEQUENCE: 44

Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Leu Ala Ser
            20                  25                  30

Gly Asn Gln Asn Asn Tyr Leu Ala Trp His Leu Gln Lys Pro Gly Gln
        35                  40                  45

Ser Pro Gln Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

Ser Tyr Ser Ala Pro Leu Thr Phe Gly Gln Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 45
<211> LENGTH: 220
<212> TYPE: PRT
<213> ORGANISM: Artificial Sequence
<220> FEATURE:
<223> OTHER INFORMATION: Synthetic amino acid sequence of H3-light

<400> SEQUENCE: 45

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp Tyr Gln Gln Lys Pro Gly Gln
        35                  40                  45

Pro Pro Lys Leu Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

```
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 46
<211> LENGTH: 219
<212> TYPE: PRT
<213> ORGANISM: Artificial Sequence
<220> FEATURE:
<223> OTHER INFORMATION: Synthetic amino acid sequence of H4-light

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu
    210                 215

<210> SEQ ID NO 47
<211> LENGTH: 1350
<212> TYPE: DNA
<213> ORGANISM: Artificial Sequence
<220> FEATURE:
<223> OTHER INFORMATION: Synthetic nucleotide sequence of H1-heavy

<400> SEQUENCE: 47
gaggtgcagc tggtggagtc tgggggaggc ttggtccagc ctggagggtc cctgagactc    60
```

```
tcctgtgcag cctctggatt caccttcact gactactaca tgagctgggt ccgccaggct      120
ccagggaagg ggctggagtg gttgggcttt attagaaaca aagctaacgg ttacaccaca      180
gaatacagtg cgtctgtgaa aggcagattc accatctcaa gagataattc aaagaactca      240
ctgtatctgc aaatgaacag cctgaaaacc gaggacacgg ccgtgtatta ctgtgctaga      300
gataactggt ttgcttactg gggtcaagga accctggtca ccgtctcctc ggctagcacc      360
aagggcccat cggtcttccc cctggcaccc tcctccaaga gcacctctgg gggcacagcg      420
gccctgggct gcctggtcaa ggactacttc cccgaaccgg tgacggtgtc gtggaactca      480
ggcgccctga ccagcggcgt gcacaccttc ccggctgtcc tacagtcctc aggactctac      540
tccctcagca gcgtggtgac cgtgccctcc agcagcttgg gcacccagac ctacatctgc      600
aacgtgaatc acaagcccag caacaccaag gtggacaaga agttgagcc caaatcttgt       660 gacaaaactc acacatgccc accgtgccca gcacctgaac tcctgggggg accgtcagtc      720
ttcctcttcc cccccaaaacc caaggacacc ctcatgatct cccggacccc tgaggtcaca     780
tgcgtggtgg tggacgtgag ccacgaagac cctgaggtca agttcaactg gtacgtggac      840
ggcgtggagg tgcataatgc caagacaaag ccgcgggagg agcagtacaa cagcacgtac      900
cgtgtggtca gcgtcctcac cgtcctgcac caggactggc tgaatggcaa ggagtacaag      960
tgcaaggtct ccaacaaagc cctcccagcc cccatcgaga aaaccatctc caaagccaaa     1020
gggcagcccc gagaaccaca ggtgtacacc ctgcccccat cccgggagga gatgaccaag     1080
aaccaggtca gcctgacctg cctggtcaaa ggcttctatc ccagcgacat cgccgtggag     1140
tgggagagca atgggcagcc ggagaacaac tacaagacca cgcctcccgt gctggactcc     1200
gacggctcct tcttcctcta cagcaagctc accgtggaca agagcaggtg gcagcagggg     1260
aacgtcttct catgctccgt gatgcatgag gctctgcaca accactacac gcagaagagc     1320
ctctccctgt ctccgggtaa atgactcgag                                      1350
```

<210> SEQ ID NO 48
<211> LENGTH: 1350
<212> TYPE: DNA
<213> ORGANISM: Artificial Sequence
<220> FEATURE:
<223> OTHER INFORMATION: Synthetic nucleotide sequence of H3-heavy

<400> SEQUENCE: 48

```
gaggtgcagc tggtggagtc tgggggaggc ttggtccagc ctggagggtc cctgagactc       60
tcctgtgcag cctctggatt caccttcact gactactaca tgagctgggt ccgccaggct      120
ccagggaagg ggctggagtg gttgggcttt attagaaaca aagctaacgg ttacaccaca      180
gaatacagtg cgtctgtgaa aggcagattc accatctcaa gagataattc aaagaactca      240
ctgtatctgc aaatgaacag cctgcgtgct gaggacacgg ccgtgtatta ctgtgctaga      300
gataactggt ttgcttactg gggtcaagga accctggtca ccgtctcctc ggctagcacc      360
aagggcccat cggtcttccc cctggcaccc tcctccaaga gcacctctgg gggcacagcg      420
gccctgggct gcctggtcaa ggactacttc cccgaaccgg tgacggtgtc gtggaactca      480
ggcgccctga ccagcggcgt gcacaccttc ccggctgtcc tacagtcctc aggactctac      540
tccctcagca gcgtggtgac cgtgccctcc agcagcttgg gcacccagac ctacatctgc      600
aacgtgaatc acaagcccag caacaccaag gtggacaaga agttgagcc caaatcttgt       660 gacaaaactc acacatgccc accgtgccca gcacctgaac tcctgggggg accgtcagtc      720
```

```
ttcctcttcc ccccaaaacc caaggacacc ctcatgatct cccggacccc tgaggtcaca      780
tgcgtggtgg tggacgtgag ccacgaagac cctgaggtca agttcaactg gtacgtggac      840
ggcgtggagg tgcataatgc caagacaaag ccgcgggagg agcagtacaa cagcacgtac      900
cgtgtggtca gcgtcctcac cgtcctgcac caggactggc tgaatggcaa ggagtacaag      960
tgcaaggtct ccaacaaagc cctcccagcc cccatcgaga aaaccatctc caaagccaaa     1020
gggcagcccc gagaaccaca ggtgtacacc ctgcccccat cccgggagga gatgaccaag     1080
aaccaggtca gcctgacctg cctggtcaaa ggcttctatc ccagcgacat cgccgtggag     1140
tgggagagca atgggcagcc ggagaacaac tacaagacca cgcctcccgt gctggactcc     1200
gacggctcct tcttcctcta cagcaagctc accgtggaca agagcaggtg gcagcagggg     1260
aacgtcttct catgctccgt gatgcatgag gctctgcaca accactacac gcagaagagc     1320
ctctccctgt ctccgggtaa atgactcgag                                      1350
```

<210> SEQ ID NO 49
<211> LENGTH: 1350
<212> TYPE: DNA
<213> ORGANISM: Artificial Sequence
<220> FEATURE:
<223> OTHER INFORMATION: Synthetic nucleotide sequence of H4-heavy

<400> SEQUENCE: 49

```
gaggttcagc tggtggagtc tggcggtggc ctggtgcagc caggggggctc actccgtttg      60 tcctgtgcag cttctggctt caccttcact gattactaca tgagctgggt gcgtcaggcc     120
ccgggtaagg gcctggaatg gttgggtttt attagaaaca agctaatgg ttacacaaca      180 gagtacagtg catctgtgaa gggtcgtttc actataagca gagataattc caaaaacaca     240
ctgtacctgc agatgaacag cctgcgtgct gaggacactg ccgtctatta ttgtgctaga     300
gataactggt ttgcttactg gggccaaggg actctggtca ccgtctcctc ggctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt      660 gacaaaactc acacatgccc accgtgccca gcacctgaac tcctgggggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac      900
cgtgtggtca gcgtcctcac cgtcctgcac caggactggc tgaatggcaa ggagtacaag      960
tgcaaggtct ccaacaaagc cctcccagcc cccatcgaga aaaccatctc caaagccaaa     1020
gggcagcccc gagaaccaca ggtgtacacc ctgcccccat cccgggagga gatgaccaag     1080
aaccaggtca gcctgacctg cctggtcaaa ggcttctatc ccagcgacat cgccgtggag     1140
tgggagagca atgggcagcc ggagaacaac tacaagacca cgcctcccgt gctggactcc     1200
gacggctcct tcttcctcta cagcaagctc accgtggaca agagcaggtg gcagcagggg     1260
aacgtcttct catgctccgt gatgcatgag gctctgcaca accactacac gcagaagagc     1320
ctctccctgt ctccgggtaa atgactcgag                                      1350
```

<210> SEQ ID NO 50
<211> LENGTH: 669
<212> TYPE: DNA
<213> ORGANISM: Artificial Sequence
<220> FEATURE:
<223> OTHER INFORMATION: Synthetic nucleotide sequence of H1-light

<400> SEQUENCE: 50

```
gacatcgtga tgacccagtc tccagactcc ctggctgtgt ctctgggcga gagggccacc    60
atcaactgca gtccagcca gagtcttta gctagcggca accaaaataa ctacttagct     120
tggcaccagc agaaaccagg acagcctcct aagatgctca ttatttgggc atctacccgg   180
gtatccgggg tccctgaccg attcagtggc agcgggtctg ggacagattt cactctcacc   240
atcagcagcc tgcaggctga agatgtggca gtttattact gtcagcaatc ctatagtgct   300
cctctcacgt tcggaggcgg taccaaggtg gagatcaaac gtacggtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga acacaaagt ctacgcctgc    600
gaagtcaccc atcagggcct gagctcgccc gtcacaaaga gcttcaacag gggagagtgt   660
tgactcgag                                                            669
```

<210> SEQ ID NO 51
<211> LENGTH: 669
<212> TYPE: DNA
<213> ORGANISM: Artificial Sequence
<220> FEATURE:
<223> OTHER INFORMATION: Synthetic nucleotide sequence of H2-light

<400> SEQUENCE: 51

```
gatattgtga tgacccagac tccactctcc ctgcccgtca cccctggaga gccggcctcc    60
atctcctgca agtccagtca gagtctttta gctagtggca accaaaataa ctacttggcc   120
tggcacctgc agaagccagg gcagtctcca cagatgctga tcatttgggc atccactagg    180
gtatctggag tcccagacag gttcagtggc agtgggtcag gcactgattt cacactgaaa   240
atcagcaggg tggaggctga ggatgttgga gtttattact gccagcagtc ctacagcgct   300
ccgctcacgt tcggacaggg taccaagctg gagctcaaac gtacggtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga acacaaagt ctacgcctgc    600
gaagtcaccc atcagggcct gagctcgccc gtcacaaaga gcttcaacag gggagagtgt   660
tgactcgag                                                            669
```

<210> SEQ ID NO 52
<211> LENGTH: 669
<212> TYPE: DNA
<213> ORGANISM: Artificial Sequence
<220> FEATURE:
<223> OTHER INFORMATION: Synthetic nucleotide sequence of H3-light

<400> SEQUENCE: 52

```
gacatcgtga tgacccagtc tccagactcc ctggctgtgt ctctgggcga gagggccacc    60
```

| | |
|---|---|
| atcaactgca agtccagcca gagtcttta gctagcggca accaaaataa ctacttagct | 120 |
| tggtaccagc agaaaccagg acagcctcct aagctgctca ttatttgggc atctacccgg | 180 |
| gtatccgggg tccctgaccg attcagtggc agcgggtctg ggacagattt cactctcacc | 240 |
| atcagcagcc tgcaggctga agatgtggca gtttattact gtcagcaatc ctatagtgct | 300 |
| cctctcacgt tcggaggcgg taccaaggtg gagatcaaac gtacggtggc tgcaccatct | 360 |
| gtcttcatct tcccgccatc tgatgagcag ttgaaatctg gaactgcctc tgttgtgtgc | 420 |
| ctgctgaata acttctatcc cagagaggcc aaagtacagt ggaaggtgga taacgccctc | 480 |
| caatcgggta actcccagga gagtgtcaca gagcaggaca gcaaggacag cacctacagc | 540 |
| ctcagcagca ccctgacgct gagcaaagca gactacgaga aacacaaagt ctacgcctgc | 600 |
| gaagtcaccc atcagggcct gagctcgccc gtcacaaaga gcttcaacag gggagagtgt | 660 |
| tgactcgag | 669 |

<210> SEQ ID NO 53
<211> LENGTH: 669
<212> TYPE: DNA
<213> ORGANISM: Artificial Sequence
<220> FEATURE:
<223> OTHER INFORMATION: Synthetic nucleotide sequence of H4-light

<400> SEQUENCE: 53

| | |
|---|---|
| gatatccaga tgacccagtc cccgagctcc ctgtccgcct ctgtgggcga tagggtcacc | 60 |
| atcacctgca agtccagtca gagtcttta gctagtggca accaaaataa ctacttggcc | 120 |
| tggcaccaac agaaaccagg aaaagctccg aaaatgctga ttatttgggc atccactagg | 180 |
| gtatctggag tccttctcg cttctctgga tccgggtctg ggacggattt cactctgacc | 240 |
| atcagcagtc tgcagccgga agacttcgca acttattact gtcagcagtc ctacagcgct | 300 |
| ccgctcacgt tcggacaggg taccaaggtg gagatcaaac gtacggtggc tgcaccatct | 360 |
| gtcttcatct tcccgccatc tgatgagcag ttgaaatctg gaactgcctc tgttgtgtgc | 420 |
| ctgctgaata acttctatcc cagagaggcc aaagtacagt ggaaggtgga taacgccctc | 480 |
| caatcgggta actcccagga gagtgtcaca gagcaggaca gcaaggacag cacctacagc | 540 |
| ctcagcagca ccctgacgct gagcaaagca gactacgaga aacacaaagt ctacgcctgc | 600 |
| gaagtcaccc atcagggcct gagctcgccc gtcacaaaga gcttcaacag gggagagtgt | 660 |
| tgactcgag | 669 |

<210> SEQ ID NO 54
<211> LENGTH: 23
<212> TYPE: PRT
<213> ORGANISM: Artificial Sequence
<220> FEATURE:
<223> OTHER INFORMATION: Synthetic linker between VH and VL

<400> SEQUENCE: 54

Gly Leu Gly Gly Leu Gly Gly Gly Ser Gly Gly Gly Gly Ser Gly
1               5                   10                  15

Gly Ser Ser Gly Val Gly Ser
            20

<210> SEQ ID NO 55
<211> LENGTH: 1088
<212> TYPE: DNA
<213> ORGANISM: Artificial Sequence
<220> FEATURE:
<223> OTHER INFORMATION: Synthetic polynucleotide encoding scFv of huAbF46 antibody

<400> SEQUENCE: 55

| | | | | | |
|---|---|---|---|---|---|
| gctagcgttt | tagcagaagt | tcaattggtt | gaatctggtg | gtggtttggt | tcaaccaggt | 60 |
| ggttctttga | gattgtcttg | tgctgcttct | ggttttactt | tcaccgatta | ttacatgtcc | 120 |
| tgggttagac | aagctccagg | taaaggtttg | gaatggttgg | gtttcattag | aaacaaggct | 180 |
| aacggttaca | ctaccgaata | ttctgcttct | gttaagggta | gattcaccat | ttctagagac | 240 |
| aactctaaga | cacccttgta | cttgcaaatg | aactccttga | gagctgaaga | tactgctgtt | 300 |
| tattactgcg | ctagagataa | ttggtttgct | tattggggtc | aaggtacttt | ggttactgtt | 360 |
| tcttctggcc | tcgggggcct | cggaggagga | ggtagtggcg | gaggaggctc | cggtggatcc | 420 |
| agcggtgtgg | gttccgatat | tcaaatgacc | caatctccat | cttctttgtc | tgcttcagtt | 480 |
| ggtgatagag | ttaccattac | ttgtaagtcc | tcccaatctt | tgttggcttc | tggtaatcag | 540 |
| aacaattact | ggcttggca | tcaacaaaaa | ccaggtaaag | ctccaaagat | gttgattatt | 600 |
| tgggcttcta | ccagagtttc | tggtgttcca | tctagatttt | ctggttctgg | ttccggtact | 660 |
| gattttactt | tgaccatttc | atccttgcaa | ccagaagatt | tcgctactta | ctactgtcaa | 720 |
| caatcttact | ctgctccatt | gacttttggt | caaggtacaa | aggtcgaaat | caagagagaa | 780 |
| ttcggtaagc | ctatccctaa | ccctctcctc | ggtctcgatt | ctacgggtgg | tggtggatct | 840 |
| ggtggtggtg | gttctggtgg | tggtggttct | caggaactga | caactatatg | cgagcaaatc | 900 |
| ccctcaccaa | ctttagaatc | gacgccgtac | tctttgtcaa | cgactactat | tttggccaac | 960 |
| gggaaggcaa | tgcaaggagt | ttttgaatat | tacaaatcag | taacgtttgt | cagtaattgc | 1020 |
| ggttctcacc | cctcaacaac | tagcaaaggc | agccccataa | acacacagta | tgttttttga | 1080 |
| gtttaaac | | | | | 1088 |

<210> SEQ ID NO 56
<211> LENGTH: 5597
<212> TYPE: DNA
<213> ORGANISM: Artificial Sequence
<220> FEATURE:
<223> OTHER INFORMATION: Synthetic expression vector including
      polynucleotide encoding scFv of huAbF46 antibody
<220> FEATURE:
<221> NAME/KEY: misc_difference
<222> LOCATION: (573)..(578)
<223> OTHER INFORMATION: NheI restriction site
<220> FEATURE:
<221> NAME/KEY: misc_difference
<222> LOCATION: (588)..(938)
<223> OTHER INFORMATION: huAbF46 VH
<220> FEATURE:
<221> NAME/KEY: misc_difference
<222> LOCATION: (939)..(1007)
<223> OTHER INFORMATION: linker
<220> FEATURE:
<221> NAME/KEY: misc_difference
<222> LOCATION: (1008)..(1349)
<223> OTHER INFORMATION: huAbF46 VL
<220> FEATURE:
<221> NAME/KEY: misc_difference
<222> LOCATION: (1350)..(1355)
<223> OTHER INFORMATION: EcoRI restriction site
<220> FEATURE:
<221> NAME/KEY: misc_difference
<222> LOCATION: (1356)..(1397)
<223> OTHER INFORMATION: V5 epitope
<220> FEATURE:
<221> NAME/KEY: misc_difference
<222> LOCATION: (1398)..(1442)
<223> OTHER INFORMATION: (G4S)3 linker
<220> FEATURE:

```
<221> NAME/KEY: misc_difference
<222> LOCATION: (1443)..(1649)
<223> OTHER INFORMATION: Aga2
<220> FEATURE:
<221> NAME/KEY: misc_difference
<222> LOCATION: (1650)..(1652)
<223> OTHER INFORMATION: TGA(stop codon)
<220> FEATURE:
<221> NAME/KEY: misc_difference
<222> LOCATION: (1653)..(1660)
<223> OTHER INFORMATION: PmeI restriction site

<400> SEQUENCE: 56
```

| | | | | | |
|---|---|---|---|---|---|
| acggattaga | agccgccgag | cgggtgacag | ccctccgaag | gaagactctc | ctccgtgcgt | 60 |
| cctcgtcttc | accggtcgcg | ttcctgaaac | gcagatgtgc | ctcgcgccgc | actgctccga | 120 |
| acaataaaga | ttctacaata | ctagcttttg | tggttatgaa | gaggaaaaat | tggcagtaac | 180 |
| ctggccccac | aaaccttcaa | atgaacgaat | caaattaaca | accataggat | gataatgcga | 240 |
| ttagttttt | agccttattt | ctggggtaat | taatcagcga | agcgatgatt | tttgatctat | 300 |
| taacagatat | ataaatgcaa | aaactgcata | accactttaa | ctaatacttt | caacattttc | 360 |
| ggtttgtatt | acttcttatt | caaatgtaat | aaaagtatca | acaaaaaatt | gttaatatac | 420 |
| ctctatactt | taacgtcaag | gagaaaaaac | cccggatcgg | actactagca | gctgtaaatac | 480 |
| gactcactat | agggaatatt | aagctaattc | tacttcatac | attttcaatt | aagatgcagt | 540 |
| tacttcgctg | tttttcaata | ttttctgtta | ttgctagcgt | tttagcagaa | gttcaattgg | 600 |
| ttgaatctgg | tggtggtttg | gttcaaccag | gtggttcttt | gagattgtct | tgtgctgctt | 660 |
| ctggttttac | tttcaccgat | tattacatgt | cctgggttag | acaagctcca | ggtaaaggtt | 720 |
| tggaatggtt | gggtttcatt | agaaacaagg | ctaacggtta | cactaccgaa | tattctgctt | 780 |
| ctgttaaggg | tagattcacc | atttctagag | acaactctaa | gaacaccttg | tacttgcaaa | 840 |
| tgaactccct | gagagctgaa | gatactgctg | tttattactg | cgctagagat | aattggtttg | 900 |
| cttattgggg | tcaaggtact | ttggttactg | tttcttctgg | cctcggggc | ctcggaggag | 960 |
| gaggtagtgg | cggaggaggc | tccggtggat | ccagcggtgt | gggttccgat | attcaaatga | 1020 |
| cccaatctcc | atcttctttg | tctgcttcag | ttggtgatag | agttaccatt | acttgtaagt | 1080 |
| cctcccaatc | tttgttggct | tctggtaatc | agaacaatta | cttggcttgg | catcaacaaa | 1140 |
| aaccaggtaa | agctccaaag | atgttgatta | tttgggcttc | taccagagtt | tctggtgttc | 1200 |
| catctagatt | ttctggttct | ggttccggta | ctgattttac | tttgaccatt | tcatccttgc | 1260 |
| aaccagaaga | tttcgctact | tactactgtc | aacaatctta | ctctgctcca | ttgacttttg | 1320 |
| gtcaaggtac | aaaggtcgaa | atcaagagag | aattcggtaa | gcctatccct | aaccctctcc | 1380 |
| tcggtctcga | ttctacgggt | ggtggtggat | ctggtggtgg | tggttctggt | ggtggtggtt | 1440 |
| ctcaggaact | gacaactata | tgcgagcaaa | tcccctcacc | aactttagaa | tcgacgccgt | 1500 |
| actctttgtc | aacgactact | attttggcca | acgggaaggc | aatgcaagga | gttttgaat | 1560 |
| attacaaatc | agtaacgttt | gtcagtaatt | gcggttctca | cccctcaaca | actagcaaag | 1620 |
| gcagccccat | aaacacacag | tatgtttttt | gagtttaaac | ccgctgatct | gataacaaca | 1680 |
| gtgtagatgt | aacaaaatcg | actttgttcc | cactgtactt | ttagctcgta | caaaatacaa | 1740 |
| tatacttttc | atttctccgt | aaacaacatg | ttttcccatg | taatatcctt | ttctattttt | 1800 |
| cgttccgtta | ccaactttac | acatacttta | tatagctatt | cacttctata | cactaaaaaa | 1860 |
| ctaagacaat | tttaattttg | ctgcctgcca | tatttcaatt | tgttataaat | tcctataatt | 1920 |
| tatcctatta | gtagctaaaa | aaagatgaat | gtgaatcgaa | tcctaagaga | attgggcaag | 1980 |

```
tgcacaaaca atacttaaat aaatactact cagtaataac ctatttctta gcattttga     2040
cgaaatttgc tattttgtta gagtctttta caccatttgt ctccacacct ccgcttacat     2100
caacaccaat aacgccattt aatctaagcg catcaccaac attttctggc gtcagtccac     2160
cagctaacat aaaatgtaag ctctcggggc tctcttgcct tccaacccag tcagaaatcg     2220
agttccaatc caaaagttca cctgtcccac ctgcttctga atcaaacaag ggaataaacg     2280
aatgaggttt ctgtgaagct gcactgagta gtatgttgca gtcttttgga aatacgagtc     2340
ttttaataac tggcaaaccg aggaactctt ggtattcttg ccacgactca tctccgtgca     2400
gttggacgat atcaatgccg taatcattga ccagagccaa aacatcctcc ttaggttgat     2460
tacgaaacac gccaaccaag tatttcggag tgcctgaact attttatat gcttttacaa     2520
gacttgaaat tttccttgca ataaccgggt caattgttct ctttctattg ggcacacata     2580
taatacccag caagtcagca tcggaatcta gagcacattc tgcggcctct gtgctctgca     2640
agccgcaaac tttcaccaat ggaccagaac tacctgtgaa attaataaca gacatactcc     2700
aagctgcctt tgtgtgctta atcacgtata ctcacgtgct caatagtcac caatgccctc     2760
cctcttggcc ctctccttt cttttttcga ccgaatttct tgaagacgaa agggcctcgt     2820
gatacgccta tttttatagg ttaatgtcat gataataatg gtttcttagg acggatcgct     2880
tgcctgtaac ttacacgcgc ctcgtatctt ttaatgatgg aataaatttgg gaatttactc     2940
tgtgtttatt tattttatg ttttgtattt ggattttaga aagtaaataa agaaggtaga     3000
agagttacgg aatgaagaaa aaaaaataaa caaaggttta aaaaatttca acaaaaagcg     3060
tactttacat atatatttat tagacaagaa aagcagatta aatagatata cattcgatta     3120
acgataagta aaatgtaaaa tcacaggatt ttcgtgtgtg gtcttctaca cagacaagat     3180
gaaacaattc ggcattaata cctgagagca ggaagagcaa gataaaaggt agtatttgtt     3240
ggcgatcccc ctagagtctt ttacatcttc ggaaaacaaa aactattttt tcttaatt    3300
cttttttac tttctatttt taatttatat atttatatta aaaaatttaa attataatta     3360
ttttatagc acgtgatgaa aaggacccag gtggcacttt tcggggaaat gtgcgcggaa     3420
cccctatttg tttattttc taaatacatt caaatatgta tccgctcatg agacaataac     3480
cctgataaat gcttcaataa tattgaaaaa ggaagagtat gagtattcaa catttccgtg     3540
tcgcccttat tcccttttt gcggcatttt gccttcctgt ttttgctcac ccagaaacgc     3600
tggtgaaagt aaaagatgct gaagatcagt tgggtgcacg agtgggttac atcgaactgg     3660
atctcaacag cggtaagatc cttgagagtt ttcgccccga agaacgtttt ccaatgatga     3720
gcactttaa agttctgcta tgtggcgcgg tattatcccg tgttgacgcc gggcaagagc     3780
aactcggtcg ccgcatacac tattctcaga atgacttggt tgagtactca ccagtcacag     3840
aaaagcatct tacgatggc atgacagtaa gagaattatg cagtgctgcc ataaccatga     3900
gtgataacac tgcggccaac ttacttctga caacgatcgg aggaccgaag gagctaaccg     3960
cttttttgca acatggggg gatcatgtaa ctcgccttga tcgttgggaa ccggagctga     4020
atgaagccat accaaacgac gagcgtgaca ccacgatgcc tgtagcaatg gcaacaacgt     4080
tgcgcaaact attaactggc gaactactta ctctagcttc ccggcaacaa ttaatagact     4140
ggatggaggc ggataaagtt gcaggaccac ttctgcgctc ggcccttccg gctggctggt     4200
ttattgctga taaatctgga gccggtgagc gtgggtctcg cggtatcatt gcagcactgg     4260
ggccagatgg taagccctcc cgtatcgtag ttatctacac gacgggcagt caggcaacta     4320
```

```
tggatgaacg aaatagacag atcgctgaga taggtgcctc actgattaag cattggtaac    4380
tgtcagacca agtttactca tatatacttt agattgattt aaaacttcat ttttaattta    4440
aaaggatcta ggtgaagatc cttttttgata atctcatgac caaaatccct taacgtgagt   4500
tttcgttcca ctgagcgtca gaccccgtag aaaagatcaa aggatcttct tgagatcctt    4560 ttttttctgcg cgtaatctgc tgcttgcaaa caaaaaaacc accgctacca gcggtggttt   4620
gtttgccgga tcaagagcta ccaactcttt ttccgaaggt aactggcttc agcagagcgc    4680
agataccaaa tactgtcctt ctagtgtagc cgtagttagg ccaccacttc aagaactctg    4740
tagcaccgcc tacatacctc gctctgctaa tcctgttacc agtggctgct gccagtggcg    4800
ataagtcgtg tcttaccggg ttggactcaa gacgatagtt accggataag gcgcagcggt    4860
cgggctgaac ggggggttcg tgcacacagc ccagcttgga gcgaacgacc tacaccgaac    4920
tgagatacct acagcgtgag cattgagaaa gcgccacgct tcccgaaggg agaaaggcgg    4980
acaggtatcc ggtaagcggc agggtcggaa caggagagcg cacgagggag cttccagggg    5040
ggaacgcctg gtatctttat agtcctgtcg ggtttcgcca cctctgactt gagcgtcgat    5100
ttttgtgatg ctcgtcaggg gggccgagcc tatggaaaaa cgccagcaac gcggcctttt    5160
tacggttcct ggccttttgc tggccttttg ctcacatgtt ctttcctgcg ttatcccctg    5220
attctgtgga taaccgtatt accgcctttg agtgagctga taccgctcgc cgcagccgaa    5280
cgaccgagcg cagcgagtca gtgagcgagg aagcggaaga gcgcccaata cgcaaaccgc    5340
ctctccccgc gcgttggccg attcattaat gcagctggca cgacaggttt cccgactgga    5400
aagcgggcag tgagcgcaac gcaattaatg tgagttacct cactcattag gcaccccagg    5460
ctttacactt tatgcttccg gctcctatgt tgtgtggaat tgtgagcgga taacaatttc    5520
acacaggaaa cagctatgac catgattacg ccaagctcgg aattaaccct cactaaaggg    5580
aacaaaagct ggctagt                                                   5597
```

<210> SEQ ID NO 57
<211> LENGTH: 13
<212> TYPE: PRT
<213> ORGANISM: Artificial Sequence
<220> FEATURE:
<223> OTHER INFORMATION: Synthetic U6-HC7 hinge

<400> SEQUENCE: 57

Glu Pro Lys Ser Cys Asp Cys His Cys Pro Pro Cys Pro
 1               5                  10

<210> SEQ ID NO 58
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-1 clone

<400> SEQUENCE: 58

```
gaattcacta gtgattaatt cgccgccacc atggattcac aggcccaggt cctcatgttg     60
ctgctgctat cggtatctgg tacctgtgga gatatccaga tgacccagtc ccgagctcc     120 ctgtccgcct ctgtgggcga tagggtcacc atcacctgca gtccagtca gagtctttta    180 gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg gacggatttc actctgacc atcagcagtc tgcagccgga agacttcgca    360
```

```
acttattact gtcagcagtc ctacagccgc ccgtacacgt tcggacaggg taccaaggtg    420
gagatcaaac gtacg                                                     435

<210> SEQ ID NO 59
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-2 clone

<400> SEQUENCE: 59
gaattcacta gtgattaatt cgccgccacc atggattcac aggcccaggt cctcatgttg     60
ctgctgctat cggtatctgg tacctgtgga gatatccaga tgacccagtc cccgagctcc    120
ctgtccgcct ctgtgggcga tagggtcacc atcacctgca agtccagtca gagtctttta    180
gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg gacggattt cactctgacc atcagcagtc tgcagccgga agacttcgca    360
acttattact gtgggcagtc ctacagccgt ccgctcacgt tcggacaggg taccaaggtg    420
gagatcaaac gtacg                                                     435

<210> SEQ ID NO 60
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-3 clone

<400> SEQUENCE: 60
gaattcacta gtgattaatt cgccgccacc atggattcac aggcccaggt cctcatgttg     60
ctgctgctat cggtatctgg tacctgtgga gatatccaga tgacccagtc cccgagctcc    120
ctgtccgcct ctgtgggcga tagggtcacc atcacctgca agtccagtca gagtctttta    180
gctagtggca accaaaataa ctacttggcc tggcaccaac agaaaccagg aaaagctccg    240
aaaatgctga ttatttgggc atccactagg gtatctggag tcccttctcg cttctctgga    300
tccgggtctg gacggattt cactctgacc atcagcagtc tgcagccgga agacttcgca    360
acttattact gtgcacagtc ctacagccat ccgttctctt tcggacaggg taccaaggtg    420
gagatcaaac gtacg                                                     435

<210> SEQ ID NO 61
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-5 clone

<400> SEQUENCE: 61
gaattcacta gtgattaatt cgccgccacc atggattcac aggcccaggt cctcatgttg     60
ctgctgctat cggtatctgg tacctgtgga gatatccaga tgacccagtc cccgagctcc    120
ctgtccgcct ctgtgggcga tagggtcacc atcacctgca agtccagtca gagtctttta    180
gctagtggca accaaaataa ctacttggcc tggcaccaac agaaaccagg aaaagctccg    240
aaaatgctga ttatttgggc atccactagg gtatctggag tcccttctcg cttctctgga    300
```

```
tccgggtctg ggacggattt cactctgacc atcagcagtc tgcagccgga agacttcgca    360
acttattact gtcagcagtc ctacagccgc ccgtttacgt tcggacaggg taccaaggtg    420
gagatcaaac gtacg                                                    435
```

<210> SEQ ID NO 62
<211> LENGTH: 462
<212> TYPE: PRT
<213> ORGANISM: Artificial Sequence
<220> FEATURE:
<223> OTHER INFORMATION: Synthetic polypeptide consisting of heavy chain
of huAbF46-H4-A1, U6-HC7 hinge and constant region of
human IgG1

<400> SEQUENCE: 62

```
Met Glu Trp Ser Trp Val Phe Leu Val Thr Leu Leu Asn Gly Ile Gln
 1               5                  10                  15

Cys Glu Val Gln Leu Val Glu Ser Gly Gly Gly Leu Val Gln Pro Gly
                20                  25                  30

Gly Ser Leu Arg Leu Ser Cys Ala Ala Ser Gly Phe Thr Phe Thr Asp
            35                  40                  45

Tyr Tyr Met Ser Trp Val Arg Gln Ala Pro Gly Lys Gly Leu Glu Trp
        50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Cys His
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320
```

```
Leu Thr Val Leu His Gln Asp Trp Leu Asn Gly Lys Glu Tyr Lys Cys
            325                 330                 335

Lys Val Ser Asn Lys Ala Leu Pro Ala Pro Ile Glu Lys Thr Ile Ser
        340                 345                 350

Lys Ala Lys Gly Gln Pro Arg Glu Pro Gln Val Tyr Thr Leu Pro Pro
    355                 360                 365

Ser Arg Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
            405                 410                 415

Gly Ser Phe Phe Leu Tyr Ser Lys Leu Thr Val Asp Lys Ser Arg Trp
        420                 425                 430

Gln Gln Gly Asn Val Phe Ser Cys Ser Val Met His Glu Ala Leu His
    435                 440                 445

Asn His Tyr Thr Gln Lys Ser Leu Ser Leu Ser Pro Gly Lys
450                 455                 460
```

<210> SEQ ID NO 63
<211> LENGTH: 1410
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, U6-HC7 hinge and
      constant region of human IgG1

<400> SEQUENCE: 63

```
gaattcgccg ccaccatgga atggagctgg gttttctcg taacactttt aaatggtatc      60
cagtgtgagg ttcagctggt ggagtctggc ggtggcctgg tgcagccagg gggctcactc    120
cgtttgtcct gtgcagcttc tggcttcacc ttcactgatt actacatgag ctgggtgcgt    180
caggccccgg gtaagggcct ggaatggttg gttttatta gaaacaaagc taatggttac    240
acaacagagt acagtgcatc tgtgaagggt cgtttcacta taagcagaga taattccaaa    300
aacacactgt acctgcagat gaacagcctg cgtgctgagg acactgccgt ctattattgt    360
gctagagata actggtttgc ttactggggc caagggactc tggtcaccgt ctcctcggct    420
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
agctgcgatt gccactgtcc tccatgtcca gcacctgaac tcctgggggg accgtcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggagga gatgaccaag   1140
aaccaggtca gcctgacctg cctggtcaaa ggcttctatc ccagcgacat cgccgtggag   1200
```

```
tgggagagca atgggcagcc ggagaacaac tacaagacca cgcctcccgt gctggactcc    1260
gacggctcct tcttcctcta cagcaagctc accgtggaca agagcaggtg gcagcagggg    1320
aacgtcttct catgctccgt gatgcatgag gctctgcaca accactacac gcagaagagc    1380
ctctccctgt ctccgggtaa atgactcgag                                     1410
```

<210> SEQ ID NO 64
<211> LENGTH: 461
<212> TYPE: PRT
<213> ORGANISM: Artificial Sequence
<220> FEATURE:
<223> OTHER INFORMATION: Synthetic polypeptide consisting of heavy chain
      of huAbF46-H4-A1, human IgG2 hinge and constant region of
      human IgG1

<400> SEQUENCE: 64

```
Met Glu Trp Ser Trp Val Phe Leu Val Thr Leu Leu Asn Gly Ile Gln
  1               5                  10                  15

Cys Glu Val Gln Leu Val Glu Ser Gly Gly Gly Leu Val Gln Pro Gly
             20                  25                  30

Gly Ser Leu Arg Leu Ser Cys Ala Ala Ser Gly Phe Thr Phe Thr Asp
         35                  40                  45

Tyr Tyr Met Ser Trp Val Arg Gln Ala Pro Gly Lys Gly Leu Glu Trp
     50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Arg Lys Cys Cys Val Glu Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320
```

```
Thr Val Leu His Gln Asp Trp Leu Asn Gly Lys Glu Tyr Lys Cys Lys
            325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
            355                 360                 365

Arg Glu Glu Met Thr Lys Asn Gln Val Ser Leu Thr Cys Leu Val Lys
            370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
            405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
            435                 440                 445

His Tyr Thr Gln Lys Ser Leu Ser Leu Ser Pro Gly Lys
            450                 455                 460
```

<210> SEQ ID NO 65
<211> LENGTH: 1407
<212> TYPE: DNA
<213> ORGANISM: Artificial Sequence
<220> FEATURE:
<223> OTHER INFORMATION: Synthetic polynucleotide encoding polypeptide
    consisting of heavy chain of huAbF46-H4-A1, human IgG2 hinge and
    constant region of human IgG1

<400> SEQUENCE: 65

```
gaattcgccg ccaccatgga atggagctgg gttttttctcg taacactttt aaatggtatc    60
cagtgtgagg ttcagctggt ggagtctggc ggtggcctgg tgcagccagg gggctcactc   120
cgtttgtcct gtcagcttc tggcttcacc ttcactgatt actacatgag ctgggtgcgt   180
caggccccgg gtaagggcct ggaatggttg ggttttatta gaaacaaagc taatggttac   240
acaacagagt acagtgcatc tgtgaagggt cgtttcacta taagcagaga taattccaaa   300
aacacactgt acctgcagat gaacagcctg cgtgctgagg acactgccgt ctattattgt   360
gctagagata ctggtttgc ttactggggc caagggactc tggtcaccgt ctcctcggct   420
agcaccaagg gcccatcggt cttccccctg gcaccctcct ccaagagcac ctctgggggc   480
acagcggccc tgggctgcct ggtcaaggac tacttccccg aaccggtgac ggtgtcgtgg   540
aactcaggcg ccctgaccag cggcgtgcac accttcccgg ctgtcctaca gtcctcagga   600
ctctactccc tcagcagcgt ggtgaccgtg ccctccagca gcttgggcac ccagacctac   660
atctgcaacg tgaatcacaa gcccagcaac accaaggtgg acaagaaagt tgagaggaag   720
tgctgtgtgg agtgccccc ctgcccagca cctgaactcc tggggggacc gtcagtcttc   780
ctcttccccc caaaacccaa ggacaccctc atgatctccc ggaccctga ggtcacatgc   840
gtggtggtgg acgtgagcca cgaagaccct gaggtcaagt tcaactggta cgtggacggc   900
gtggaggtgc ataatgccaa gacaaagccg cgggaggagc agtacaacag cacgtaccgt   960
gtggtcagcg tcctcaccgt cctgcaccag gactggctga atggcaagga gtacaagtgc  1020
aaggtctcca acaaagccct cccagccccc atcgagaaaa ccatctccaa agccaagggg  1080
cagccccgag aaccacaggt gtacaccctg cccccatccc gggaggagat gaccaagaac  1140
caggtcagcc tgacctgcct ggtcaaaggc ttctatccca gcgacatcgc cgtggagtgg  1200
```

```
gagagcaatg ggcagccgga gaacaactac aagaccacgc ctcccgtgct ggactccgac   1260
ggctccttct tcctctacag caagctcacc gtggacaaga gcaggtggca gcaggggaac   1320
gtcttctcat gctccgtgat gcatgaggct ctgcacaacc actacacgca gaagagcctc   1380
tccctgtctc cgggtaaatg actcgag                                       1407
```

```
<210> SEQ ID NO 66
<211> LENGTH: 460
<212> TYPE: PRT
<213> ORGANISM: Artificial Sequence
<220> FEATURE:
<223> OTHER INFORMATION: Synthetic polypeptide consisting of heavy chain
      of huAbF46-H4-A1, human IgG2 hinge and constant region
      of human IgG2

<400> SEQUENCE: 66
```

```
Met Glu Trp Ser Trp Val Phe Leu Val Thr Leu Leu Asn Gly Ile Gln
 1               5                  10                  15

Cys Glu Val Gln Leu Val Glu Ser Gly Gly Gly Leu Val Gln Pro Gly
             20                  25                  30

Gly Ser Leu Arg Leu Ser Cys Ala Ala Ser Gly Phe Thr Phe Thr Asp
         35                  40                  45

Tyr Tyr Met Ser Trp Val Arg Gln Ala Pro Gly Lys Gly Leu Glu Trp
     50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Asn Phe Gly Thr Gln Thr Tyr Thr Cys Asn Val Asp His Lys Pro Ser
    210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Gln Phe
        275                 280                 285

Asn Trp Tyr Val Asp Gly Val Glu Val His Asn Ala Lys Thr Lys Pro
    290                 295                 300

Arg Glu Glu Gln Phe Asn Ser Thr Phe Arg Val Val Ser Val Leu Thr
```

```
                    305                 310                 315                 320
Val Val His Gln Asp Trp Leu Asn Gly Lys Glu Tyr Lys Cys Lys Val
                325                 330                 335

Ser Asn Lys Gly Leu Pro Ala Pro Ile Glu Lys Thr Ile Ser Lys Thr
                340                 345                 350

Lys Gly Gln Pro Arg Glu Pro Gln Val Tyr Thr Leu Pro Pro Ser Arg
                355                 360                 365

Glu Glu Met Thr Lys Asn Gln Val Ser Leu Thr Cys Leu Val Lys Gly
            370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Met Leu Asp Ser Asp Gly Ser
                405                 410                 415

Phe Phe Leu Tyr Ser Lys Leu Thr Val Asp Lys Ser Arg Trp Gln Gln
                420                 425                 430

Gly Asn Val Phe Ser Cys Ser Val Met His Glu Ala Leu His Asn His
                435                 440                 445

Tyr Thr Gln Lys Ser Leu Ser Leu Ser Pro Gly Lys
            450                 455                 460

<210> SEQ ID NO 67
<211> LENGTH: 1404
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, human IgG2 hinge and
      constant region of human IgG2

<400> SEQUENCE: 67
gaattcgccg ccaccatgga atggagctgg gttttctcg taacactttt aaatggtatc    60
cagtgtgagg ttcagctggt ggagtctggc ggtggcctgg tgcagccagg ggctcactc   120 cgtttgtcct gtgcagcttc tggcttcacc ttcactgatt actacatgag ctgggtgcgt   180
caggccccgg gtaagggcct ggaatggttg gtttttatta gaaacaaagc taatggttac   240
acaacagagt acagtgcatc tgtgaagggt cgtttcacta agcagagaa taattccaaa   300 aacacactgt acctgcagat gaacagcctg cgtgctgagg acactgccgt ctattattgt   360
gctagagata actggtttgc ttactgggc aagggactc tggtcaccgt ctcctcggct   420
agcaccaagg gcccatcggt cttccccctg gcgccctgct ccaggagcac ctccgagagc   480
acagcggccc tgggctgcct ggtcaaggac tacttccccg aaccggtgac ggtgtcgtgg   540
aactcaggcg ctctgaccag cggcgtgcac accttcccag ctgtcctaca gtcctcagga   600
ctctactccc tcagcagcgt ggtgaccgtg ccctccagca acttcggcac ccagacctac   660
acctgcaacg tagatcacaa gcccagcaac accaaggtgg acaagacagt tgagcgcaaa   720
tgttgtgtcg agtgcccacc gtgcccagca ccacctgtgg caggaccgtc agtcttcctc   780
ttccccccaa aacccaagga caccctcatg atctcccgga cccctgaggt cacgtgcgtg   840
gtggtggacg tgagccacga agaccccgag gtccagttca actggtacgt ggacggcgtg   900
gaggtgcata atgccaagac aaagccacgg gaggagcagt tcaacagcac gttccgtgtg   960
gtcagcgtcc tcaccgttgt gcaccaggac tggctgaacg gcaaggagta caagtgcaag  1020
gtctccaaca aagccctccc agcccccatc gagaaaacca tctccaaaac caaagggcag  1080
ccccgagaac cacaggtgta caccctgccc ccatcccggg aggagatgac caagaaccag  1140
```

```
gtcagcctga cctgcctggt caaaggcttc tacccagcg acatcgccgt ggagtgggag      1200
agcaatgggc agccggagaa caactacaag accacgcctc ccatgctgga ctccgacggc      1260
tccttcttcc tctacagcaa gctcaccgtg gacaagagca ggtggcagca ggggaacgtc      1320
ttctcatgct ccgtgatgca tgaggctctg cacaaccact acacgcagaa gagcctctcc      1380
ctgtctccgg gtaaatgact cgag                                             1404
```

<210> SEQ ID NO 68
<211> LENGTH: 240
<212> TYPE: PRT
<213> ORGANISM: Artificial Sequence
<220> FEATURE:
<223> OTHER INFORMATION: Synthetic polypeptide consisting of light chain
      of huAbF46-H4-A1(H36Y) and human kappa constant region

<400> SEQUENCE: 68

```
Met Asp Ser Gln Ala Gln Val Leu Met Leu Leu Leu Leu Ser Val Ser
  1               5                  10                  15

Gly Thr Cys Gly Asp Ile Gln Met Thr Gln Ser Pro Ser Ser Leu Ser
             20                  25                  30

Ala Ser Val Gly Asp Arg Val Thr Ile Thr Cys Lys Ser Ser Gln Ser
         35                  40                  45

Leu Leu Ala Ser Gly Asn Gln Asn Asn Tyr Leu Ala Trp Tyr Gln Gln
     50                  55                  60

Lys Pro Gly Lys Ala Pro Lys Met Leu Ile Ile Trp Ala Ser Thr Arg
 65                  70                  75                  80

Val Ser Gly Val Pro Ser Arg Phe Ser Gly Ser Gly Ser Gly Thr Asp
                 85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 69
<211> LENGTH: 758
<212> TYPE: DNA
<213> ORGANISM: Artificial Sequence
<220> FEATURE:
<223> OTHER INFORMATION: Synthetic polynucleotide encoding polypeptide
      consisting of light chain of huAbF46-H4-A1(H36Y) and human kappa
      constant region

<400> SEQUENCE: 69

```
aattcactag tgattaattc gccgccacca tggattcaca ggcccaggtc ctcatgttgc        60
```

```
tgctgctatc ggtatctggt acctgtggag atatccagat gacccagtcc ccgagctccc      120
tgtccgcctc tgtgggcgat agggtcacca tcacctgcaa gtccagtcag agtcttttag      180
ctagtggcaa ccaaaataac tacttggcct ggtaccaaca gaaaccagga aaagctccga      240
aaatgctgat tatttgggca tccactaggg tatctggagt cccttctcgc ttctctggat      300
ccgggtctgg gacggatttc actctgacca tcagcagtct gcagccggaa gacttcgcaa      360
cttattactg tcagcagtcc tacagccgcc cgtacacgtt cggacagggt accaaggtgg      420
agatcaaacg tacggtggct gcaccatctg tcttcatctt cccgccatct gatgagcagt      480
tgaaatctgg aactgcctct gttgtgtgcc tgctgaataa cttctatccc agagaggcca      540 agtacagtg gaaggtggat aacgccctcc aatcgggtaa ctcccaggag agtgtcacag       600
agcaggacag caaggacagc acctacagcc tcagcagcac cctgacgctg agcaaagcag      660
actacgagaa acacaaagtc tacgcctgcg aagtcaccca tcagggcctg agctcgcccg      720
tcacaaagag cttcaacagg ggagagtgtt gactcgag                              758
```

<210> SEQ ID NO 70
<211> LENGTH: 240
<212> TYPE: PRT
<213> ORGANISM: Artificial Sequence
<220> FEATURE:
<223> OTHER INFORMATION: Synthetic polypeptide consisting of light chain
    of huAbF46-H4-A1 and human kappa constant region <400> SEQUENCE: 70

```
Met Asp Ser Gln Ala Gln Val Leu Met Leu Leu Leu Leu Ser Val Ser
  1               5                  10                  15

Gly Thr Cys Gly Asp Ile Gln Met Thr Gln Ser Pro Ser Ser Leu Ser
             20                  25                  30

Ala Ser Val Gly Asp Arg Val Thr Ile Thr Cys Lys Ser Ser Gln Ser
         35                  40                  45

Leu Leu Ala Ser Gly Asn Gln Asn Asn Tyr Leu Ala Trp His Gln Gln
     50                  55                  60

Lys Pro Gly Lys Ala Pro Lys Met Leu Ile Ile Trp Ala Ser Thr Arg
 65                  70                  75                  80

Val Ser Gly Val Pro Ser Arg Phe Ser Gly Ser Gly Ser Gly Thr Asp
                 85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
```

<210> SEQ ID NO 71
<211> LENGTH: 19
<212> TYPE: PRT
<213> ORGANISM: Artificial Sequence
<220> FEATURE:
<223> OTHER INFORMATION: Synthetic epitope in SEMA domain of c-Met

<400> SEQUENCE: 71

Phe Ser Pro Gln Ile Glu Glu Pro Ser Gln Cys Pro Asp Cys Val Val
1               5                   10                  15

Ser Ala Leu

<210> SEQ ID NO 72
<211> LENGTH: 10
<212> TYPE: PRT
<213> ORGANISM: Artificial Sequence
<220> FEATURE:
<223> OTHER INFORMATION: Synthetic epitope in SEMA domain of c-Met

<400> SEQUENCE: 72

Pro Gln Ile Glu Glu Pro Ser Gln Cys Pro
1               5                   10

<210> SEQ ID NO 73
<211> LENGTH: 5
<212> TYPE: PRT
<213> ORGANISM: Artificial Sequence
<220> FEATURE:
<223> OTHER INFORMATION: Synthetic epitope in SEMA domain of c-Met

<400> SEQUENCE: 73

Glu Glu Pro Ser Gln
1               5

<210> SEQ ID NO 74
<211> LENGTH: 117
<212> TYPE: PRT
<213> ORGANISM: Artificial Sequence
<220> FEATURE:
<223> OTHER INFORMATION: Synthetic heavy chain variable region of
    anti-c-Met antibody (AbF46 or huAbF46-H1)

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

```
<210> SEQ ID NO 75
<211> LENGTH: 114
<212> TYPE: PRT
<213> ORGANISM: Artificial Sequence
<220> FEATURE:
<223> OTHER INFORMATION: Synthetic light chain variable region of
      anti-c-Met antibody (AbF46 or huAbF46-H1)

<400> SEQUENCE: 75

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Ala Ser
             20                  25                  30

Gly Asn Gln Asn Asn Tyr Leu Ala Trp His Gln Gln Lys Pro Gly Gln
         35                  40                  45

Pro Pro Lys Met Leu Ile Ile Trp Ala Ser Thr Arg Val Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gly Gly Thr Lys Val Glu Ile
            100                 105                 110

Lys Arg

<210> SEQ ID NO 76
<211> LENGTH: 1416
<212> TYPE: DNA
<213> ORGANISM: Artificial Sequence
<220> FEATURE:
<223> OTHER INFORMATION: Synthetic nucleotide sequence of heavy chain of
      anti-c-Met antibody (AbF46 or huAbF46-H1)
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 76
gaattcgccg ccaccatgga atggagctgg gttttctcg taacactttt aaatggtatc      60
cagtgtgagg tgaagctggt ggagtctgga ggaggcttgg tacagcctgg gggttctctg    120
agactctcct gtgcaacttc tgggttcacc ttcactgatt actacatgag ctgggtccgc    180
cagcctccag gaaaggcact tgagtggttg ggttttatta gaaacaaagc taatggttac    240
```

```
acaacagagt acagtgcatc tgtgaagggt cggttcacca tctccagaga taattcccaa      300
agcatcctct atcttcaaat ggacaccctg agagctgagg acagtgccac ttattactgt      360
gcaagagata actggtttgc ttactggggc caagggactc tggtcactgt ctctgcagct      420
agcaccaagg gcccatcggt cttccccctg gcacctcct ccaagagcac ctctgggggc       480
acagcggccc tgggctgcct ggtcaaggac tacttccccg aaccggtgac ggtgtcgtgg      540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
tcttgtgaca aaactcacac atgcccaccg tgcccagcac ctgaactcct ggggggaccg     780
tcagtcttcc tcttcccccc aaaacccaag gacaccctca tgatctcccg gacccctgag     840
gtcacatgcg tggtggtgga cgtgagccac gaagaccctg aggtcaagtt caactggtac     900
gtggacggcg tggaggtgca taatgccaag acaaagccgc gggaggagca gtacaacagc     960
acgtaccgtg tggtcagcgt cctcaccgtc ctgcaccagg actggctgaa tggcaaggag    1020
tacaagtgca aggtctccaa caaagccctc ccagccccca tcgagaaaac catctccaaa    1080
gccaaagggc agccccgaga accacaggtg tacaccctgc ccccatcccg ggaggagatg    1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga ctcgag                              1416
```

<210> SEQ ID NO 77
<211> LENGTH: 759
<212> TYPE: DNA
<213> ORGANISM: Artificial Sequence
<220> FEATURE:
<223> OTHER INFORMATION: Synthetic nucleotide sequence of light chain of
      anti-c-Met antibody (AbF46 or huAbF46-H1)
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 77

```
gaattcacta gtgattaatt cgccgccacc atggattcac aggcccaggt cctcatgttg     60
ctgctgctat cggtatctgg tacctgtgga gacattttga tgacccagtc tccatcctcc    120
ctgactgtgt cagcaggaga gaaggtcact atgagctgca agtccagtca gagtctttta    180
gctagtggca accaaaataa ctacttggcc tggcaccagc agaaaccagg acgatctcct    240
aaaatgctga taatttgggc atccactagg gtatctggag tccctgatcg cttcataggc    300
agtggatctg ggacggattt cactctgacc atcaacagtg tgcaggctga agatctggct    360
gtttattact gtcagcagtc ctacagcgct ccgctcacgt tcggtgctgg gaccaagctg    420
gagctgaaac gtacggtggc tgcaccatct gtcttcatct tcccgccatc tgatgagcag    480
ttgaaatctg gaactgcctc tgttgtgtgc ctgctgaata acttctatcc cagagaggcc    540
aaagtacagt ggaaggtgga taacgccctc caatcgggta actcccagga gagtgtcaca    600
gagcaggaca gcaaggacag cacctacagc ctcagcagca ccctgacgct gagcaaagca    660
gactacgaga aacacaaagt ctacgcctgc gaagtcaccc atcagggcct gagctcgccc    720
gtcacaaaga gcttcaacag gggagagtgt tgactcgag                           759
```

<210> SEQ ID NO 78
<211> LENGTH: 4170
<212> TYPE: DNA
<213> ORGANISM: Artificial Sequence
<220> FEATURE:
<223> OTHER INFORMATION: Synthetic polynucleotide encoding c-Met protein

<400> SEQUENCE: 78

```
atgaaggccc ccgctgtgct tgcacctggc atcctcgtgc tcctgtttac cttggtgcag     60
aggagcaatg gggagtgtaa agaggcacta gcaaagtccg agatgaatgt gaatatgaag    120
tatcagcttc ccaacttcac cgcggaaaca cccatccaga atgtcattct acatgagcat    180
cacattttcc ttggtgccac taactacatt tatgttttaa atgaggaaga ccttcagaag    240
gttgctgagt acaagactgg gcctgtgctg gaacacccag attgtttccc atgtcaggac    300
tgcagcagca aagccaattt atcaggaggt gtttggaaag ataacatcaa catggctcta    360
gttgtcgaca cctactatga tgatcaactc attagctgtg gcagcgtcaa cagagggacc    420
tgccagcgac atgtctttcc ccacaatcat actgctgaca tacagtcgga ggttcactgc    480
atattctccc cacagataga agagcccagc cagtgtcctg actgtgtggt gagcgccctg    540
ggagccaaag tcctttcatc tgtaaaggac cggttcatca acttctttgt aggcaatacc    600
ataaattctt cttatttccc agatcatcca ttgcattcga tatcagtgag aaggctaaag    660
gaaacgaaag atggttttat gtttttgacg gaccagtcct acattgatgt tttacctgag    720
ttcagagatt cttaccccat taagtatgtc catgcctttg aaagcaacaa ttttatttac    780
ttcttgacgg tccaaaggga aactctagat gctcagactt ttcacacaag aataatcagg    840
ttctgttcca taaactctgg attgcattcc tacatggaaa tgcctctgga gtgtattctc    900
acagaaaaga gaaaaaagag atccacaaag aaggaagtgt ttaatatact tcaggctgcg    960
tatgtcagca agcctggggc ccagcttgct agacaaatag gagccagcct gaatgatgac   1020
attcttttcg ggtgttcgc acaaagcaag ccagattctg ccgaaccaat ggatcgatct    1080
gccatgtgtg cattccctat caaatatgtc aacgacttct tcaacaagat cgtcaacaaa   1140
aacaatgtga gatgtctcca gcatttttac ggacccaatc atgagcactg ctttaatagg   1200
acacttctga gaaattcatc aggctgtgaa gcgcgccgtg atgaatatcg aacagagttt   1260
```

```
accacagctt tgcagcgcgt tgacttattc atgggtcaat tcagcgaagt cctcttaaca    1320
tctatatcca ccttcattaa aggagacctc accatagcta atcttgggac atcagagggt    1380
cgcttcatgc aggttgtggt ttctcgatca ggaccatcaa cccctcatgt gaattttctc    1440
ctggactccc atccagtgtc tccagaagtg attgtggagc atacattaaa ccaaaatggc    1500
tacacactgg ttatcactgg gaagaagatc acgaagatcc cattgaatgg cttgggctgc    1560
agacatttcc agtcctgcag tcaatgcctc tctgccccac cctttgttca gtgtggctgg    1620
tgccacgaca aatgtgtgcg atcggaggaa tgcctgagcg ggacatggac tcaacagatc    1680
tgtctgcctg caatctacaa ggttttccca aatagtgcac cccttgaagg agggacaagg    1740
ctgaccatat gtggctggga ctttggattt cggaggaata taaatttga tttaaagaaa    1800 actagagttc tccttggaaa tgagagctgc accttgactt taagtgagag cacgatgaat    1860
acattgaaat gcacagttgg tcctgccatg aataagcatt tcaatatgtc cataattatt    1920
tcaaatggcc acgggacaac acaatacagt acattctcct atgtggatcc tgtaataaca    1980
agtatttcgc cgaaatacgg tcctatggct ggtggcactt tacttacttt aactggaaat    2040
tacctaaaca gtgggaattc tagacacatt tcaattggtg aaaaacatg tactttaaaa    2100 agtgtgtcaa acagtattct tgaatgttat accccagccc aaaccatttc aactgagttt    2160
gctgttaaat tgaaaattga cttagccaac cgagagacaa gcatcttcag ttaccgtgaa    2220
gatcccattg tctatgaaat tcatccaacc aaatctttta ttagtggtgg gagcacaata    2280
acaggtgttg ggaaaaacct gaattcagtt agtgtcccga gaatggtcat aaatgtgcat    2340
gaagcaggaa ggaactttac agtggcatgt caacatcgct ctaattcaga gataatctgt    2400
tgtaccactc cttccctgca acagctgaat ctgcaactcc ccctgaaaac caaagccttt    2460
ttcatgttag atgggatcct ttccaaatac tttgatctca tttatgtaca taatcctgtg    2520
tttaagcctt ttgaaaagcc agtgatgatc tcaatgggca atgaaaatgt actggaaatt    2580
aagggaaatg atattgaccc tgaagcagtt aaaggtgaag tgttaaaagt tggaaataag    2640
agctgtgaga atatacactt acattctgaa gccgttttat gcacggtccc caatgacctg    2700
ctgaaattga acagcgagct aaatatagag tggaagcaag caatttcttc aaccgtcctt    2760
ggaaaagtaa tagttcaacc agatcagaat ttcacaggat tgattgctgg tgttgtctca    2820
atatcaacag cactgttatt actacttggg ttttttcctgt ggctgaaaaa gagaaagcaa    2880
attaaagatc tgggcagtga attagttcgc tacgatgcaa gagtacacac tcctcatttg    2940
gataggcttg taagtgcccg aagtgtaagc ccaactacag aaatggtttc aaatgaatct    3000
gtagactacc gagctacttt tccagaagat cagtttccta attcatctca gaacggttca    3060
tgccgacaag tgcagtatcc tctgacagac atgtccccca tcctaactag tgggactct    3120 gatatatcca gtccattact gcaaaatact gtccacattg acctcagtgc tctaaatcca    3180
gagctggtcc aggcagtgca gcatgtagtg attgggccca gtagcctgat gtgcatttc    3240 aatgaagtca taggaagagg gcattttggt tgtgtatatc atgggacttt gttgacaat    3300 gatggcaaga aaattcactg tgctgtgaaa tccttgaaca gaatcactga cataggagaa    3360
gtttcccaat ttctgaccga gggaatcatc atgaaagatt ttagtcatcc caatgtcctc    3420
tcgctcctgg gaatctgcct gcgaagtgaa gggtctccgc tggtggtcct accatacatg    3480
aaacatggag atcttcgaaa tttcattcga aatgagactc ataatccaac tgtaaaagat    3540
cttattggct ttggtcttca gtagccaaa ggcatgaaat atcttgcaag caaaagtttt    3600
gtccacagag acttggctgc aagaaactgt atgctggatg aaaaattcac agtcaaggtt    3660
```

```
gctgattttg gtcttgccag agacatgtat gataaagaat actatagtgt acacaacaaa    3720
acaggtgcaa agctgccagt gaagtggatg gctttggaaa gtctgcaaac tcaaaagttt    3780
accaccaagt cagatgtgtg gtcctttggc gtgctcctct gggagctgat gacaagagga    3840
gccccacctt atcctgacgt aaacaccttt gatataactg tttacttgtt gcaagggaga    3900
agactcctac aacccgaata ctgcccagac cccttatatg aagtaatgct aaaatgctgg    3960
caccctaaag ccgaaatgcg cccatccttt tctgaactgg tgtcccggat atcagcgatc    4020
ttctctactt tcattgggga gcactatgtc catgtgaacg ctactatgt gaacgtaaaa    4080 tgtgtcgctc cgtatccttc tctgttgtca tcagaagata cgctgatga tgaggtggac    4140 acacgaccag cctccttctg ggagacatca                                    4170
```

<210> SEQ ID NO 79
<211> LENGTH: 444
<212> TYPE: PRT
<213> ORGANISM: Artificial Sequence
<220> FEATURE:
<223> OTHER INFORMATION: Synthetic SEMA domain of c-Met

<400> SEQUENCE: 79

```
Leu His Glu His His Ile Phe Leu Gly Ala Thr Asn Tyr Ile Tyr Val
 1               5                  10                  15

Leu Asn Glu Glu Asp Leu Gln Lys Val Ala Glu Tyr Lys Thr Gly Pro
            20                  25                  30

Val Leu Glu His Pro Asp Cys Phe Pro Cys Gln Asp Cys Ser Ser Lys
        35                  40                  45

Ala Asn Leu Ser Gly Gly Val Trp Lys Asp Asn Ile Asn Met Ala Leu
    50                  55                  60

Val Val Asp Thr Tyr Tyr Asp Asp Gln Leu Ile Ser Cys Gly Ser Val
65                  70                  75                  80

Asn Arg Gly Thr Cys Gln Arg His Val Phe Pro His Asn His Thr Ala
                85                  90                  95

Asp Ile Gln Ser Glu Val His Cys Ile Phe Ser Pro Gln Ile Glu Glu
            100                 105                 110

Pro Ser Gln Cys Pro Asp Cys Val Val Ser Ala Leu Gly Ala Lys Val
        115                 120                 125

Leu Ser Ser Val Lys Asp Arg Phe Ile Asn Phe Val Gly Asn Thr
    130                 135                 140

Ile Asn Ser Ser Tyr Phe Pro Asp His Pro Leu His Ser Ile Ser Val
145                 150                 155                 160

Arg Arg Leu Lys Glu Thr Lys Asp Gly Phe Met Phe Leu Thr Asp Gln
                165                 170                 175

Ser Tyr Ile Asp Val Leu Pro Glu Phe Arg Asp Ser Tyr Pro Ile Lys
            180                 185                 190

Tyr Val His Ala Phe Glu Ser Asn Asn Phe Ile Tyr Phe Leu Thr Val
        195                 200                 205

Gln Arg Glu Thr Leu Asp Ala Gln Thr Phe His Thr Arg Ile Ile Arg
    210                 215                 220

Phe Cys Ser Ile Asn Ser Gly Leu His Ser Tyr Met Glu Met Pro Leu
225                 230                 235                 240

Glu Cys Ile Leu Thr Glu Lys Arg Lys Lys Arg Ser Thr Lys Lys Glu
                245                 250                 255

Val Phe Asn Ile Leu Gln Ala Ala Tyr Val Ser Lys Pro Gly Ala Gln
            260                 265                 270
```

```
Leu Ala Arg Gln Ile Gly Ala Ser Leu Asn Asp Asp Ile Leu Phe Gly
            275                 280                 285

Val Phe Ala Gln Ser Lys Pro Asp Ser Ala Glu Pro Met Asp Arg Ser
    290                 295                 300

Ala Met Cys Ala Phe Pro Ile Lys Tyr Val Asn Asp Phe Phe Asn Lys
305                 310                 315                 320

Ile Val Asn Lys Asn Val Arg Cys Leu Gln His Phe Tyr Gly Pro
                325                 330                 335

Asn His Glu His Cys Phe Asn Arg Thr Leu Leu Arg Asn Ser Ser Gly
                340                 345                 350

Cys Glu Ala Arg Arg Asp Glu Tyr Arg Thr Glu Phe Thr Thr Ala Leu
            355                 360                 365

Gln Arg Val Asp Leu Phe Met Gly Gln Phe Ser Glu Val Leu Leu Thr
        370                 375                 380

Ser Ile Ser Thr Phe Ile Lys Gly Asp Leu Thr Ile Ala Asn Leu Gly
385                 390                 395                 400

Thr Ser Glu Gly Arg Phe Met Gln Val Val Ser Arg Ser Gly Pro
                405                 410                 415

Ser Thr Pro His Val Asn Phe Leu Leu Asp Ser His Pro Val Ser Pro
            420                 425                 430

Glu Val Ile Val Glu His Thr Leu Asn Gln Asn Gly
        435                 440

<210> SEQ ID NO 80
<211> LENGTH: 451
<212> TYPE: PRT
<213> ORGANISM: Artificial Sequence
<220> FEATURE:
<223> OTHER INFORMATION: Synthetic PSI-IPT domain of c-Met

<400> SEQUENCE: 80

Tyr Thr Leu Val Ile Thr Gly Lys Lys Ile Thr Lys Ile Pro Leu Asn
 1               5                  10                  15

Gly Leu Gly Cys Arg His Phe Gln Ser Cys Ser Gln Cys Leu Ser Ala
                20                  25                  30

Pro Pro Phe Val Gln Cys Gly Trp Cys His Asp Lys Cys Val Arg Ser
            35                  40                  45

Glu Glu Cys Leu Ser Gly Thr Trp Thr Gln Gln Ile Cys Leu Pro Ala
    50                  55                  60

Ile Tyr Lys Val Phe Pro Asn Ser Ala Pro Leu Glu Gly Gly Thr Arg
65                  70                  75                  80

Leu Thr Ile Cys Gly Trp Asp Phe Gly Phe Arg Arg Asn Asn Lys Phe
                85                  90                  95

Asp Leu Lys Lys Thr Arg Val Leu Leu Gly Asn Glu Ser Cys Thr Leu
            100                 105                 110

Thr Leu Ser Glu Ser Thr Met Asn Thr Leu Lys Cys Thr Val Gly Pro
        115                 120                 125

Ala Met Asn Lys His Phe Asn Met Ser Ile Ile Ser Asn Gly His
130                 135                 140

Gly Thr Thr Gln Tyr Ser Thr Phe Ser Tyr Val Asp Pro Val Ile Thr
145                 150                 155                 160

Ser Ile Ser Pro Lys Tyr Gly Pro Met Ala Gly Gly Thr Leu Leu Thr
                165                 170                 175

Leu Thr Gly Asn Tyr Leu Asn Ser Gly Asn Ser Arg His Ile Ser Ile
            180                 185                 190
```

```
Gly Gly Lys Thr Cys Thr Leu Lys Ser Val Ser Asn Ser Ile Leu Glu
            195                 200                 205

Cys Tyr Thr Pro Ala Gln Thr Ile Ser Thr Glu Phe Ala Val Lys Leu
    210                 215                 220

Lys Ile Asp Leu Ala Asn Arg Glu Thr Ser Ile Phe Ser Tyr Arg Glu
225                 230                 235                 240

Asp Pro Ile Val Tyr Glu Ile His Pro Thr Lys Ser Phe Ile Ser Thr
                245                 250                 255

Trp Trp Lys Glu Pro Leu Asn Ile Val Ser Phe Leu Phe Cys Phe Ala
            260                 265                 270

Ser Gly Gly Ser Thr Ile Thr Gly Val Gly Lys Asn Leu Asn Ser Val
            275                 280                 285

Ser Val Pro Arg Met Val Ile Asn Val His Glu Ala Gly Arg Asn Phe
    290                 295                 300

Thr Val Ala Cys Gln His Arg Ser Asn Ser Glu Ile Ile Cys Cys Thr
305                 310                 315                 320

Thr Pro Ser Leu Gln Gln Leu Asn Leu Gln Leu Pro Leu Lys Thr Lys
                325                 330                 335

Ala Phe Phe Met Leu Asp Gly Ile Leu Ser Lys Tyr Phe Asp Leu Ile
            340                 345                 350

Tyr Val His Asn Pro Val Phe Lys Pro Phe Glu Lys Pro Val Met Ile
    355                 360                 365

Ser Met Gly Asn Glu Asn Val Leu Glu Ile Lys Gly Asn Asp Ile Asp
370                 375                 380

Pro Glu Ala Val Lys Gly Glu Val Leu Lys Val Gly Asn Lys Ser Cys
385                 390                 395                 400

Glu Asn Ile His Leu His Ser Glu Ala Val Leu Cys Thr Val Pro Asn
                405                 410                 415

Asp Leu Leu Lys Leu Asn Ser Glu Leu Asn Ile Glu Trp Lys Gln Ala
            420                 425                 430

Ile Ser Ser Thr Val Leu Gly Lys Val Ile Val Gln Pro Asp Gln Asn
            435                 440                 445

Phe Thr Gly
    450

<210> SEQ ID NO 81
<211> LENGTH: 313
<212> TYPE: PRT
<213> ORGANISM: Artificial Sequence
<220> FEATURE:
<223> OTHER INFORMATION: Synthetic TyrKc domain of c-Met

<400> SEQUENCE: 81

Val His Phe Asn Glu Val Ile Gly Arg Gly His Phe Gly Cys Val Tyr
1               5                   10                  15

His Gly Thr Leu Leu Asp Asn Asp Gly Lys Lys Ile His Cys Ala Val
            20                  25                  30

Lys Ser Leu Asn Arg Ile Thr Asp Ile Gly Glu Val Ser Gln Phe Leu
        35                  40                  45

Thr Glu Gly Ile Ile Met Lys Asp Phe Ser His Pro Asn Val Leu Ser
    50                  55                  60

Leu Leu Gly Ile Cys Leu Arg Ser Glu Gly Ser Pro Leu Val Val Leu
65                  70                  75                  80

Pro Tyr Met Lys His Gly Asp Leu Arg Asn Phe Ile Arg Asn Glu Thr
                85                  90                  95
```

```
His Asn Pro Thr Val Lys Asp Leu Ile Gly Phe Gly Leu Gln Val Ala
            100                 105                 110
Lys Gly Met Lys Tyr Leu Ala Ser Lys Lys Phe Val His Arg Asp Leu
        115                 120                 125
Ala Ala Arg Asn Cys Met Leu Asp Glu Lys Phe Thr Val Lys Val Ala
    130                 135                 140
Asp Phe Gly Leu Ala Arg Asp Met Tyr Asp Lys Glu Tyr Tyr Ser Val
145                 150                 155                 160
His Asn Lys Thr Gly Ala Lys Leu Pro Val Lys Trp Met Ala Leu Glu
            165                 170                 175
Ser Leu Gln Thr Gln Lys Phe Thr Thr Lys Ser Asp Val Trp Ser Phe
        180                 185                 190
Gly Val Leu Leu Trp Glu Leu Met Thr Arg Gly Ala Pro Pro Tyr Pro
    195                 200                 205
Asp Val Asn Thr Phe Asp Ile Thr Val Tyr Leu Leu Gln Gly Arg Arg
210                 215                 220
Leu Leu Gln Pro Glu Tyr Cys Pro Asp Pro Leu Tyr Glu Val Met Leu
225                 230                 235                 240
Lys Cys Trp His Pro Lys Ala Glu Met Arg Pro Ser Phe Ser Glu Leu
            245                 250                 255
Val Ser Arg Ile Ser Ala Ile Phe Ser Thr Phe Ile Gly Glu His Tyr
        260                 265                 270
Val His Val Asn Ala Thr Tyr Val Asn Val Lys Cys Val Ala Pro Tyr
    275                 280                 285
Pro Ser Leu Leu Ser Ser Glu Asp Asn Ala Asp Glu Val Asp Thr
290                 295                 300
Arg Pro Ala Ser Phe Trp Glu Thr Ser
305                 310
```

<210> SEQ ID NO 82
<211> LENGTH: 1332
<212> TYPE: DNA
<213> ORGANISM: Artificial Sequence
<220> FEATURE:
<223> OTHER INFORMATION: Synthetic polynucleotide encoding SEMA domain of c-Met

<400> SEQUENCE: 82

| | | | | |
|---|---|---|---|---|
| ctacatgagc atcacatttt ccttggtgcc actaactaca tttatgtttt aaatgaggaa | 60 |
| gaccttcaga aggttgctga gtacaagact gggcctgtgc tggaacaccc agattgtttc | 120 |
| ccatgtcagg actgcagcag caaagccaat ttatcaggag gtgtttggaa agataacatc | 180 |
| aacatggctc tagttgtcga cacctactat gatgatcaac tcattagctg tggcagcgtc | 240 |
| aacagaggga cctgccagcg acatgtcttt ccccacaatc atactgctga catacagtcg | 300 |
| gaggttcact gcatattctc cccacagata gaagagccca gccagtgtcc tgactgtgtg | 360 |
| gtgagcgccc tgggagccaa agtcctttca tctgtaaagg accggttcat caacttcttt | 420 |
| gtaggcaata ccataaattc ttcttatttc ccagatcatc cattgcattc gatatcagtg | 480 |
| agaaggctaa aggaaacgaa agatggtttt atgtttttga cggaccagtc ctacattgat | 540 |
| gttttacctg agttcagaga ttcttacccc attaagtatg tccatgcctt tgaaagcaac | 600 |
| aatttttattt acttcttgac ggtccaaagg gaaactctag atgctcagac ttttcacaca | 660 |
| agaataatca ggttctgttc cataaactct ggattgcatt cctacatgga aatgcctctg | 720 |
| gagtgtattc tcacagaaaa gagaaaaaag agatccacaa agaaggaagt gtttaatata | 780 |

```
cttcaggctg cgtatgtcag caagcctggg gcccagcttg ctagacaaat aggagccagc    840
ctgaatgatg acattctttt cggggtgttc gcacaaagca agccagattc tgccgaacca    900
atggatcgat ctgccatgtg tgcattccct atcaaatatg tcaacgactt cttcaacaag    960
atcgtcaaca aaaacaatgt gagatgtctc cagcatttt acggacccaa tcatgagcac    1020
tgctttaata ggacacttct gagaaattca tcaggctgtg aagcgcgccg tgatgaatat    1080
cgaacagagt ttaccacagc tttgcagcgc gttgacttat tcatgggtca attcagcgaa    1140
gtcctcttaa catctatatc caccttcatt aaaggagacc tcaccatagc taatcttggg    1200
acatcagagt gtcgcttcat gcaggttgtg gtttctcgat caggaccatc aacccctcat    1260 gtgaatttc tcctggactc ccatccagtg tctccagaag tgattgtgga gcatacatta    1320
aaccaaaatg gc                                                       1332

<210> SEQ ID NO 83
<211> LENGTH: 1299
<212> TYPE: DNA
<213> ORGANISM: Artificial Sequence
<220> FEATURE:
<223> OTHER INFORMATION: Synthetic polynucleotide encoding PSI-IPT
      domain of c-Met

<400> SEQUENCE: 83
tacacactgg ttatcactgg gaagaagatc acgaagatcc cattgaatgg cttgggctgc    60
agacatttcc agtcctgcag tcaatgcctc tctgccccac cctttgttca gtgtggctgg    120
tgccacgaca aatgtgtgcg atcggaggaa tgcctgagcg ggacatggac tcaacagatc    180
tgtctgcctg caatctacaa ggttttccca aatagtgcac cccttgaagg agggacaagg    240
ctgaccatat gtggctggga ctttggattt cggaggaata taaatttga tttaaagaaa    300 actagagttc tccttggaaa tgagagctgc accttgactt aagtgagag cacgatgaat    360 acattgaaat gcacagttgg tcctgccatg aataagcatt tcaatatgtc cataattatt    420
tcaaatggcc acgggacaac acaatacagt acattctcct atgtggatcc tgtaataaca    480
agtatttcgc cgaaatacgg tcctatggct ggtggcactt tacttacttt aactggaaat    540
tacctaaaca gtgggaattc tagacacatt tcaattggtg gaaaaacatg tacttttaaaa   600 agtgtgtcaa acagtattct tgaatgttat accccagccc aaaccatttc aactgagttt    660
gctgttaaat tgaaaattga cttagccaac cgagagacaa gcatcttcag ttaccgtgaa    720
gatcccattg tctatgaaat tcatccaacc aaatctttta ttagtggtgg gagcacaata    780
acaggtgttg ggaaaaacct gaattcagtt agtgtcccga gaatggtcat aaatgtgcat    840
gaagcaggaa ggaactttac agtggcatgt caacatcgct ctaattcaga gataatctgt    900
tgtaccactc cttccctgca acagctgaat ctgcaactcc cctgaaaac caaagccttt    960 ttcatgttag atgggatcct ttccaaatac tttgatctca tttatgtaca taatcctgtg    1020
tttaagcctt ttgaaaagcc agtgatgatc tcaatgggca atgaaaatgt actgaaaatt    1080
aagggaaatg atattgaccc tgaagcagtt aaaggtgaag tgttaaaagt tggaaataag    1140
agctgtgaga atatacactt acattctgaa gccgttttat gcacggtccc caatgacctg    1200
ctgaaattga acagcgagct aaatatagag tggaagcaag caatttcttc aaccgtcctt    1260
ggaaaagtaa tagttcaacc agatcagaat ttcacagga                           1299

<210> SEQ ID NO 84
<211> LENGTH: 939
```

```
<212> TYPE: DNA
<213> ORGANISM: Artificial Sequence
<220> FEATURE:
<223> OTHER INFORMATION: Synthetic polynucleotide encoding TyrKc domain
      of c-Met

<400> SEQUENCE: 84
gtgcatttca atgaagtcat aggaagaggg catttggtt gtgtatatca tgggactttg      60
ttggacaatg atggcaagaa aattcactgt gctgtgaaat ccttgaacag aatcactgac    120
ataggagaag tttcccaatt tctgaccgag ggaatcatca tgaaagattt tagtcatccc    180
aatgtcctct cgctcctggg aatctgcctg cgaagtgaag ggtctccgct ggtggtccta    240
ccatacatga acatggaga tcttcgaaat tcattcgaa atgagactca taatccaact      300
gtaaaagatc ttattggctt tggtcttcaa gtagccaaag gcatgaaata tcttgcaagc    360
aaaaagtttg tccacagaga cttggctgca agaaactgta tgctggatga aaaattcaca    420
gtcaaggttg ctgattttgg tcttgccaga gacatgtatg ataaagaata ctatagtgta    480
cacaacaaaa caggtgcaaa gctgccagtg aagtggatgg ctttggaaag tctgcaaact    540
caaaagttta ccaccaagtc agatgtgtgg tcctttggcg tgctcctctg ggagctgatg    600
acaagaggag ccccacctta tcctgacgta acaccttg atataactgt ttacttgttg      660
caagggagaa gactcctaca acccgaatac tgcccagacc ccttatatga agtaatgcta    720
aaatgctggc accctaaagc cgaaatgcgc ccatccttt ctgaactggt gtcccggata     780
tcagcgatct tctctacttt cattggggag cactatgtcc atgtgaacgc tacttatgtg    840
aacgtaaaat gtgtcgctcc gtatccttct ctgttgtcat cagaagataa cgctgatgat    900
gaggtggaca cacgaccagc ctccttctgg gagacatca                           939

<210> SEQ ID NO 85
<211> LENGTH: 13
<212> TYPE: PRT
<213> ORGANISM: Artificial Sequence
<220> FEATURE:
<223> OTHER INFORMATION: Synthetic heavy chain CDR3 of anti-c-Met
      antibody

<400> SEQUENCE: 85

Asp Asn Trp Phe Ala Tyr Trp Gly Gln Gly Thr Leu Val
 1               5                  10

<210> SEQ ID NO 86
<211> LENGTH: 10
<212> TYPE: PRT
<213> ORGANISM: Artificial Sequence
<220> FEATURE:
<223> OTHER INFORMATION: Synthetic light chain CDR3 of anti-c-Met
      antibody

<400> SEQUENCE: 86

Leu Thr Phe Gly Ala Gly Thr Lys Leu Glu
 1               5                  10

<210> SEQ ID NO 87
<211> LENGTH: 117
<212> TYPE: PRT
<213> ORGANISM: Artificial Sequence
<220> FEATURE:
<223> OTHER INFORMATION: Synthetic heavy chain variable region of
      monoclonal antibody AbF46

<400> SEQUENCE: 87
```

-continued

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asp Thr Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ala
        115

<210> SEQ ID NO 88
<211> LENGTH: 114
<212> TYPE: PRT
<213> ORGANISM: Artificial Sequence
<220> FEATURE:
<223> OTHER INFORMATION: Synthetic light chain variable region of anti-c-Met antibody

<400> SEQUENCE: 88

Asp Ile Leu Met Thr Gln Ser Pro Ser Ser Leu Thr Val Ser Ala Gly
1               5                   10                  15

Glu Lys Val Thr Met Ser Cys Lys Ser Ser Gln Ser Leu Leu Ala Ser
            20                  25                  30

Gly Asn Gln Asn Asn Tyr Leu Ala Trp His Gln Lys Pro Gly Arg
        35                  40                  45

Ser Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Asn Ser Val Gln Ala Glu Asp Leu Ala Val Tyr Tyr Cys Gln Gln
                85                  90                  95

Ser Tyr Ser Ala Pro Leu Thr Phe Gly Ala Gly Thr Lys Leu Glu Leu
            100                 105                 110

Lys Arg

<210> SEQ ID NO 89
<211> LENGTH: 17
<212> TYPE: PRT
<213> ORGANISM: Artificial Sequence
<220> FEATURE:
<223> OTHER INFORMATION: Synthetic light chain CDR3 of anti-c-Met antibody

<400> SEQUENCE: 89

Gln Gln Ser Tyr Ser Ala Pro Leu Thr Phe Gly Ala Gly Thr Lys Leu
1               5                   10                  15

Glu

<210> SEQ ID NO 90
<211> LENGTH: 117
<212> TYPE: PRT
<213> ORGANISM: Artificial Sequence -continued

```
<220> FEATURE:
<223> OTHER INFORMATION: Synthetic heavy chain variable region of AT-VH1

<400> SEQUENCE: 90

Glu Val Lys Leu Val Glu Ser Gly Gly Gly Leu Val Gln Pro Gly Gly
 1               5                  10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 91
<211> LENGTH: 117
<212> TYPE: PRT
<213> ORGANISM: Artificial Sequence
<220> FEATURE:
<223> OTHER INFORMATION: Synthetic heavy chain variable region of AT-VH2

<400> SEQUENCE: 91

Glu Val Lys Leu Val Glu Ser Gly Gly Gly Leu Val Gln Pro Gly Gly
 1               5                  10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 92
<211> LENGTH: 117
<212> TYPE: PRT
<213> ORGANISM: Artificial Sequence
<220> FEATURE:
<223> OTHER INFORMATION: Synthetic heavy chain variable region of AT-VH3

<400> SEQUENCE: 92

Glu Val Gln Leu Val Glu Ser Gly Gly Gly Leu Val Gln Pro Gly Gly
 1               5                  10                  15

Ser Leu Arg Leu Ser Cys Ala Thr Ser Gly Phe Thr Phe Thr Asp Tyr
            20                  25                  30
```

Tyr Met Ser Trp Val Arg Gln Pro Pro Gly Lys Gly Leu Glu Trp Leu
            35                  40                  45

Gly Phe Ile Arg Asn Lys Ala Asn Gly Tyr Thr Thr Glu Tyr Ser Ala
        50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 93
<211> LENGTH: 117
<212> TYPE: PRT
<213> ORGANISM: Artificial Sequence
<220> FEATURE:
<223> OTHER INFORMATION: Synthetic heavy chain variable region of AT-VH4

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
            35                  40                  45

Gly Phe Ile Arg Asn Lys Ala Asn Gly Tyr Thr Thr Glu Tyr Ser Ala
        50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 94
<211> LENGTH: 117
<212> TYPE: PRT
<213> ORGANISM: Artificial Sequence
<220> FEATURE:
<223> OTHER INFORMATION: Synthetic heavy chain variable region of AT-VH5

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
            35                  40                  45

Gly Phe Ile Arg Asn Lys Ala Asn Gly Tyr Thr Thr Glu Tyr Ser Ala
        50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

```
Tyr Cys Ala Arg Asp Asn Trp Phe Ala Tyr Trp Gly Gln Gly Thr Leu
                100                 105                 110

Val Thr Val Ser Ser
        115

<210> SEQ ID NO 95
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 95

Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
             20                  25                  30

Gly Asn Gln Asn Asn Tyr Leu Ala Trp His Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Ala Pro Leu Thr Phe Gly Gln Gly Thr Lys Val Glu Ile
             100                 105                 110

Lys Arg

<210> SEQ ID NO 96
<211> LENGTH: 113
<212> TYPE: PRT
<213> ORGANISM: Artificial Sequence
<220> FEATURE:
<223> OTHER INFORMATION: Synthetic light chain variable region of AT-Vk1

<400> SEQUENCE: 96

Asp Ile Leu Met Thr Gln Ser Pro Ser Ser Leu Thr Ala Ser Val Gly
  1               5                  10                  15

Asp Arg Val Thr Met Thr Cys Lys Ser Ser Gln Ser Leu Leu Ala Ser
             20                  25                  30

Gly Asn Gln Asn Asn Tyr Leu Ala Trp His Gln Lys Pro Gly Lys
         35                  40                  45

Ala Pro Lys Met Leu Ile Ile Trp Ala Ser Thr Arg Val Ser Gly Val
     50                  55                  60

Pro Asp Arg Phe Ile Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gln Gly Thr Lys Leu Glu Ile
             100                 105                 110

Lys

<210> SEQ ID NO 97
<211> LENGTH: 113
<212> TYPE: PRT
<213> ORGANISM: Artificial Sequence
```

```
<220> FEATURE:
<223> OTHER INFORMATION: Synthetic light chain variable region of AT-Vk2

<400> SEQUENCE: 97

Asp Ile Leu Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
        50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 98
<211> LENGTH: 113
<212> TYPE: PRT
<213> ORGANISM: Artificial Sequence
<220> FEATURE:
<223> OTHER INFORMATION: Synthetic light chain variable region of AT-Vk3

<400> SEQUENCE: 98

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
        50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 99
<211> LENGTH: 113
<212> TYPE: PRT
<213> ORGANISM: Artificial Sequence
<220> FEATURE:
<223> OTHER INFORMATION: Synthetic light chain variable region of AT-Vk4

<400> SEQUENCE: 99

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45
```

```
Ala Pro Lys Met Leu Ile Ile Trp Ala Ser Thr Arg Val Ser Gly Val
        50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 100
<211> LENGTH: 13
<212> TYPE: PRT
<213> ORGANISM: Artificial Sequence
<220> FEATURE:
<223> OTHER INFORMATION: Synthetic modified hinge region(U7-HC6)

<400> SEQUENCE: 100

Glu Pro Ser Cys Asp Lys His Cys Cys Pro Pro Cys Pro
 1               5                  10

<210> SEQ ID NO 101
<211> LENGTH: 13
<212> TYPE: PRT
<213> ORGANISM: Artificial Sequence
<220> FEATURE:
<223> OTHER INFORMATION: Synthetic modified hinge region(U6-HC7)

<400> SEQUENCE: 101

Glu Pro Lys Ser Cys Asp Cys His Cys Pro Pro Cys Pro
 1               5                  10

<210> SEQ ID NO 102
<211> LENGTH: 12
<212> TYPE: PRT
<213> ORGANISM: Artificial Sequence
<220> FEATURE:
<223> OTHER INFORMATION: Synthetic modified hinge region(U3-HC9)

<400> SEQUENCE: 102

Glu Arg Lys Cys Cys Val Glu Cys Pro Pro Cys Pro
 1               5                  10

<210> SEQ ID NO 103
<211> LENGTH: 14
<212> TYPE: PRT
<213> ORGANISM: Artificial Sequence
<220> FEATURE:
<223> OTHER INFORMATION: Synthetic modified hinge region(U6-HC8)

<400> SEQUENCE: 103

Glu Pro Arg Asp Cys Gly Cys Lys Pro Cys Pro Pro Cys Pro
 1               5                  10

<210> SEQ ID NO 104
<211> LENGTH: 13
<212> TYPE: PRT
<213> ORGANISM: Artificial Sequence
<220> FEATURE:
<223> OTHER INFORMATION: Synthetic modified hinge region(U8-HC5)

<400> SEQUENCE: 104

Glu Lys Cys Asp Lys Thr His Thr Cys Pro Pro Cys Pro
 1               5                  10
```

<210> SEQ ID NO 105
<211> LENGTH: 15
<212> TYPE: PRT
<213> ORGANISM: Artificial Sequence
<220> FEATURE:
<223> OTHER INFORMATION: Synthetic human hinge region

<400> SEQUENCE: 105

Glu Pro Lys Ser Cys Asp Lys Thr His Thr Cys Pro Pro Cys Pro
 1               5                  10                  15

<210> SEQ ID NO 106
<211> LENGTH: 17
<212> TYPE: PRT
<213> ORGANISM: Artificial Sequence
<220> FEATURE:
<223> OTHER INFORMATION: Synthetic CDR-L1 of antibody L3-11Y

<400> SEQUENCE: 106

Lys Ser Ser Gln Ser Leu Leu Ala Trp Gly Asn Gln Asn Asn Tyr Leu
 1               5                  10                  15

Ala

<210> SEQ ID NO 107
<211> LENGTH: 114
<212> TYPE: PRT
<213> ORGANISM: Artificial Sequence
<220> FEATURE:
<223> OTHER INFORMATION: Synthetic amino acid sequence of light chain
      variable region of antibody L3-11Y

<400> SEQUENCE: 107

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Trp
                20                  25                  30

Gly Asn Gln Asn Asn Tyr Leu Ala Trp Tyr Gln Gln Lys Pro Gly Lys
            35                  40                  45

Ala Pro Lys Met Leu Ile Ile Trp Ala Ser Thr Arg Val Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg

<210> SEQ ID NO 108
<211> LENGTH: 220
<212> TYPE: PRT
<213> ORGANISM: Artificial Sequence
<220> FEATURE:
<223> OTHER INFORMATION: Synthetic amino acid sequence of light chain of
      antibody L3-11Y

<400> SEQUENCE: 108

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Trp
                20                  25                  30

```
Gly Asn Gln Asn Asn Tyr Leu Ala Trp Tyr Gln Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 109
<211> LENGTH: 21
<212> TYPE: DNA
<213> ORGANISM: Artificial Sequence
<220> FEATURE:
<223> OTHER INFORMATION: Synthetic Probe Sequence for THSD7A

<400> SEQUENCE: 109
cctcttgaac ttgcgtgcct g                                              21

<210> SEQ ID NO 110
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 110
tttttaagac ttcttgtctc tctcc                                          25

<210> SEQ ID NO 111
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 111
aacgagtcct caagttcagt atttt                                          25

<210> SEQ ID NO 112
<211> LENGTH: 25
<212> TYPE: DNA
<213> ORGANISM: Artificial Sequence
<220> FEATURE:
```

<223> OTHER INFORMATION: Synthetic Probe Sequence for THSD7A

<400> SEQUENCE: 112
tacaatacgt ttctactttc cctga                                                25

<210> SEQ ID NO 113
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 113
tgattttcaa actggttgcc tgcat                                                25

<210> SEQ ID NO 114
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 114
ggaaggcaca tttttgcact atatt                                                25

<210> SEQ ID NO 115
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 115
agtgcagcac gataggcgct taacc                                                25

<210> SEQ ID NO 116
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 116
taggcgctta accagtattg ccata                                                25

<210> SEQ ID NO 117
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 117
gtattgccat agaaactgcc tcttt                                                25

<210> SEQ ID NO 118
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 118
aactgcctct tttcatgtgg gatga                                                25

```
<210> SEQ ID NO 119
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 119
gacatttgca agttcttgta tcctg                                          25

<210> SEQ ID NO 120
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 120
gctattacac ctgctgtaca cacac                                          25

<210> SEQ ID NO 121
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 121
acttctctat tgacactttt acctc                                          25

<210> SEQ ID NO 122
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 122
tgacactttt acctcaccga ggggg                                          25

<210> SEQ ID NO 123
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 123
gaactgctgt tccctagaat gaagg                                          25

<210> SEQ ID NO 124
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 124
agaatgaagg tctgttgttt ggttt                                          25

<210> SEQ ID NO 125
<211> LENGTH: 25
<212> TYPE: DNA
<213> ORGANISM: Artificial Sequence
<220> FEATURE:
<223> OTHER INFORMATION: Synthetic Probe Sequence for THSD7A
```

```
<400> SEQUENCE: 125
ttatatgatt tgctggact atttc                                          25

<210> SEQ ID NO 126
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 126
ggactatttc actagaaacc acgta                                         25

<210> SEQ ID NO 127
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 127
gaataggact aactgatctc ttttg                                         25

<210> SEQ ID NO 128
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 128 aaagggctg atttgcttat tcatc                                          25

<210> SEQ ID NO 129
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 129
atgtggacag taatcttaat ttcaa                                         25

<210> SEQ ID NO 130
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 130
gaggatacta cggtgtagct taagt                                         25

<210> SEQ ID NO 131
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 131
agcacaaatt acttctaaca aggca                                         25

<210> SEQ ID NO 132
<211> LENGTH: 25
```

```
<212> TYPE: DNA
<213> ORGANISM: Artificial Sequence
<220> FEATURE:
<223> OTHER INFORMATION: Synthetic Probe Sequence for THSD7A

<400> SEQUENCE: 132
gtattttccc ctacgtaatg tacat                                           25

<210> SEQ ID NO 133
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 133
gtacatgtct ttaggccaca gtatt                                           25

<210> SEQ ID NO 134
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 134
aggtggcagt ggtcattgta gctta                                           25

<210> SEQ ID NO 135
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 135
taatcagacc cctgttaagt tcctg                                           25

<210> SEQ ID NO 136
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 136
caaggtaaat tcacgtcttc cttct                                           25

<210> SEQ ID NO 137
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 137
aatagacctc tcacacactt attta                                           25

<210> SEQ ID NO 138
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 138
```
gtctctttct actcttgaca gctat                                         25

<210> SEQ ID NO 139
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 139
cttgacagct attcttacct acttc                                         25

<210> SEQ ID NO 140
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 140
ttcccactaa acatgcccaa ttttt                                         25

<210> SEQ ID NO 141
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 141
tcctatattt ccttccctat tagaa                                         25

<210> SEQ ID NO 142
<211> LENGTH: 25
<212> TYPE: DNA
<213> ORGANISM: Artificial Sequence
<220> FEATURE:
<223> OTHER INFORMATION: Synthetic Probe Sequence for THSD7A

<400> SEQUENCE: 142
gaatcaaagt gtcactcact cagag                                         25

<210> SEQ ID NO 143
<211> LENGTH: 22
<212> TYPE: DNA
<213> ORGANISM: Artificial Sequence
<220> FEATURE:
<223> OTHER INFORMATION: Synthetic Probe Sequence for MET

<400> SEQUENCE: 143
cttcacttcg caggcagatt cc                                            22

<210> SEQ ID NO 144
<211> LENGTH: 25
<212> TYPE: DNA
<213> ORGANISM: Artificial Sequence
<220> FEATURE:
<223> OTHER INFORMATION: Synthetic Probe Sequence for MET

<400> SEQUENCE: 144
gttgtcgaca cctactatga tgatc                                         25

<210> SEQ ID NO 145
<211> LENGTH: 25
<212> TYPE: DNA
<213> ORGANISM: Artificial Sequence

```
<220> FEATURE:
<223> OTHER INFORMATION: Synthetic Probe Sequence for MET

<400> SEQUENCE: 145
cagcgtcaac agagggacct gccag                                              25

<210> SEQ ID NO 146
<211> LENGTH: 25
<212> TYPE: DNA
<213> ORGANISM: Artificial Sequence
<220> FEATURE:
<223> OTHER INFORMATION: Synthetic Probe Sequence for MET

<400> SEQUENCE: 146
tttccccaca atcatactgc tgaca                                              25

<210> SEQ ID NO 147
<211> LENGTH: 25
<212> TYPE: DNA
<213> ORGANISM: Artificial Sequence
<220> FEATURE:
<223> OTHER INFORMATION: Synthetic Probe Sequence for MET

<400> SEQUENCE: 147
agatagaaga gcccagccag tgtcc                                              25

<210> SEQ ID NO 148
<211> LENGTH: 25
<212> TYPE: DNA
<213> ORGANISM: Artificial Sequence
<220> FEATURE:
<223> OTHER INFORMATION: Synthetic Probe Sequence for MET

<400> SEQUENCE: 148
ggagccaaag tcctttcatc tgtaa                                              25

<210> SEQ ID NO 149
<211> LENGTH: 25
<212> TYPE: DNA
<213> ORGANISM: Artificial Sequence
<220> FEATURE:
<223> OTHER INFORMATION: Synthetic Probe Sequence for MET

<400> SEQUENCE: 149
taaaggaccg gttcatcaac ttctt                                              25

<210> SEQ ID NO 150
<211> LENGTH: 25
<212> TYPE: DNA
<213> ORGANISM: Artificial Sequence
<220> FEATURE:
<223> OTHER INFORMATION: Synthetic Probe Sequence for MET

<400> SEQUENCE: 150
atttcccaga tcatccattg cattc                                              25

<210> SEQ ID NO 151
<211> LENGTH: 25
<212> TYPE: DNA
<213> ORGANISM: Artificial Sequence
<220> FEATURE:
<223> OTHER INFORMATION: Synthetic Probe Sequence for MET

<400> SEQUENCE: 151
acggaccagt cctacattga tgttt                                              25
```

```
<210> SEQ ID NO 152
<211> LENGTH: 25
<212> TYPE: DNA
<213> ORGANISM: Artificial Sequence
<220> FEATURE:
<223> OTHER INFORMATION: Synthetic Probe Sequence for MET

<400> SEQUENCE: 152
gagttcagag attcttaccc catta                                              25

<210> SEQ ID NO 153
<211> LENGTH: 25
<212> TYPE: DNA
<213> ORGANISM: Artificial Sequence
<220> FEATURE:
<223> OTHER INFORMATION: Synthetic Probe Sequence for MET

<400> SEQUENCE: 153
ctagatgctc agactttca cacaa                                               25

<210> SEQ ID NO 154
<211> LENGTH: 25
<212> TYPE: DNA
<213> ORGANISM: Artificial Sequence
<220> FEATURE:
<223> OTHER INFORMATION: Synthetic Probe Sequence for MET

<400> SEQUENCE: 154
atcaggttct gttccataaa ctctg                                              25

<210> SEQ ID NO 155
<211> LENGTH: 23
<212> TYPE: DNA
<213> ORGANISM: Artificial Sequence
<220> FEATURE:
<223> OTHER INFORMATION: Synthetic Probe Sequence for RAB31

<400> SEQUENCE: 155
atacgctgaa tccataggtg cca                                                23

<210> SEQ ID NO 156
<211> LENGTH: 25
<212> TYPE: DNA
<213> ORGANISM: Artificial Sequence
<220> FEATURE:
<223> OTHER INFORMATION: Synthetic Probe Sequence for RAB31

<400> SEQUENCE: 156
aacattgtaa tggccatcgc tggaa                                              25

<210> SEQ ID NO 157
<211> LENGTH: 25
<212> TYPE: DNA
<213> ORGANISM: Artificial Sequence
<220> FEATURE:
<223> OTHER INFORMATION: Synthetic Probe Sequence for RAB31

<400> SEQUENCE: 157
gaaacaagtg cgacctctca gatat                                              25

<210> SEQ ID NO 158
<211> LENGTH: 25
<212> TYPE: DNA
<213> ORGANISM: Artificial Sequence
<220> FEATURE:
<223> OTHER INFORMATION: Synthetic Probe Sequence for RAB31
```

-continued

```
<400> SEQUENCE: 158
ggaggttccc ctgaaggatg ctaag                                              25

<210> SEQ ID NO 159
<211> LENGTH: 25
<212> TYPE: DNA
<213> ORGANISM: Artificial Sequence
<220> FEATURE:
<223> OTHER INFORMATION: Synthetic Probe Sequence for RAB31

<400> SEQUENCE: 159
tacgctgaat ccataggtgc catcg                                              25

<210> SEQ ID NO 160
<211> LENGTH: 25
<212> TYPE: DNA
<213> ORGANISM: Artificial Sequence
<220> FEATURE:
<223> OTHER INFORMATION: Synthetic Probe Sequence for RAB31

<400> SEQUENCE: 160
gtgccatcgt ggttgagaca agtgc                                              25

<210> SEQ ID NO 161
<211> LENGTH: 25
<212> TYPE: DNA
<213> ORGANISM: Artificial Sequence
<220> FEATURE:
<223> OTHER INFORMATION: Synthetic Probe Sequence for RAB31

<400> SEQUENCE: 161
ttcaaggaat cagccgccag atccc                                              25

<210> SEQ ID NO 162
<211> LENGTH: 25
<212> TYPE: DNA
<213> ORGANISM: Artificial Sequence
<220> FEATURE:
<223> OTHER INFORMATION: Synthetic Probe Sequence for RAB31

<400> SEQUENCE: 162
tgagaagcca accatgcaag ccagc                                              25

<210> SEQ ID NO 163
<211> LENGTH: 25
<212> TYPE: DNA
<213> ORGANISM: Artificial Sequence
<220> FEATURE:
<223> OTHER INFORMATION: Synthetic Probe Sequence for RAB31

<400> SEQUENCE: 163
cgtggtccac ggtacttgaa gaagc                                              25

<210> SEQ ID NO 164
<211> LENGTH: 25
<212> TYPE: DNA
<213> ORGANISM: Artificial Sequence
<220> FEATURE:
<223> OTHER INFORMATION: Synthetic Probe Sequence for RAB31

<400> SEQUENCE: 164
atcctgtgca ctgctgaagg accct                                              25

<210> SEQ ID NO 165
```

```
<210> SEQ ID NO 165
<211> LENGTH: 25
<212> TYPE: DNA
<213> ORGANISM: Artificial Sequence
<220> FEATURE:
<223> OTHER INFORMATION: Synthetic Probe Sequence for RAB31

<400> SEQUENCE: 165
gagtgagcac actggctttg catcc                                          25

<210> SEQ ID NO 166
<211> LENGTH: 25
<212> TYPE: DNA
<213> ORGANISM: Artificial Sequence
<220> FEATURE:
<223> OTHER INFORMATION: Synthetic Probe Sequence for RAB31

<400> SEQUENCE: 166
accaccacaa aatggccttt agtgt                                          25

<210> SEQ ID NO 167
<211> LENGTH: 25
<212> TYPE: DNA
<213> ORGANISM: Artificial Sequence
<220> FEATURE:
<223> OTHER INFORMATION: Synthetic Probe Sequence for RAB31

<400> SEQUENCE: 167
gaatatgacg ttaccttgca gacta                                          25

<210> SEQ ID NO 168
<211> LENGTH: 25
<212> TYPE: DNA
<213> ORGANISM: Artificial Sequence
<220> FEATURE:
<223> OTHER INFORMATION: Synthetic Probe Sequence for RAB31

<400> SEQUENCE: 168 tttttttgtgt gggctccagt tctca                                         25

<210> SEQ ID NO 169
<211> LENGTH: 25
<212> TYPE: DNA
<213> ORGANISM: Artificial Sequence
<220> FEATURE:
<223> OTHER INFORMATION: Synthetic Probe Sequence for RAB31

<400> SEQUENCE: 169
gttctgcaat gctcatggca agttg                                          25

<210> SEQ ID NO 170
<211> LENGTH: 25
<212> TYPE: DNA
<213> ORGANISM: Artificial Sequence
<220> FEATURE:
<223> OTHER INFORMATION: Synthetic Probe Sequence for RAB31

<400> SEQUENCE: 170
accgactggg tatctagctt actgt                                          25

<210> SEQ ID NO 171
<211> LENGTH: 25
<212> TYPE: DNA
<213> ORGANISM: Artificial Sequence
<220> FEATURE:
<223> OTHER INFORMATION: Synthetic Probe Sequence for RAB31

<400> SEQUENCE: 171
```
atcattgttg aaaccagacc ctgta                                                 25

<210> SEQ ID NO 172
<211> LENGTH: 25
<212> TYPE: DNA
<213> ORGANISM: Artificial Sequence
<220> FEATURE:
<223> OTHER INFORMATION: Synthetic Probe Sequence for RAB31

<400> SEQUENCE: 172
agaccctgta gtccagtggt gctgc                                                 25

<210> SEQ ID NO 173
<211> LENGTH: 25
<212> TYPE: DNA
<213> ORGANISM: Artificial Sequence
<220> FEATURE:
<223> OTHER INFORMATION: Synthetic Probe Sequence for RAB31

<400> SEQUENCE: 173
taaagagctt ccatctgggc tggac                                                 25

<210> SEQ ID NO 174
<211> LENGTH: 25
<212> TYPE: DNA
<213> ORGANISM: Artificial Sequence
<220> FEATURE:
<223> OTHER INFORMATION: Synthetic Probe Sequence for RAB31

<400> SEQUENCE: 174
tggacccagt tcttgcacat acaag                                                 25

<210> SEQ ID NO 175
<211> LENGTH: 25
<212> TYPE: DNA
<213> ORGANISM: Artificial Sequence
<220> FEATURE:
<223> OTHER INFORMATION: Synthetic Probe Sequence for RAB31

<400> SEQUENCE: 175
gcacatacaa gacaccgctg cagtc                                                 25

<210> SEQ ID NO 176
<211> LENGTH: 25
<212> TYPE: DNA
<213> ORGANISM: Artificial Sequence
<220> FEATURE:
<223> OTHER INFORMATION: Synthetic Probe Sequence for RAB31

<400> SEQUENCE: 176
accgctgcag tcagctagga ccttt                                                 25

<210> SEQ ID NO 177
<211> LENGTH: 25
<212> TYPE: DNA
<213> ORGANISM: Artificial Sequence
<220> FEATURE:
<223> OTHER INFORMATION: Synthetic Probe Sequence for RAB31

<400> SEQUENCE: 177
ggtttaacac acactgattc atact                                                 25

<210> SEQ ID NO 178
<211> LENGTH: 23
<212> TYPE: DNA

```
<213> ORGANISM: Artificial Sequence
<220> FEATURE:
<223> OTHER INFORMATION: Synthetic Probe Sequence for FAM126A

<400> SEQUENCE: 178
tctctgctga cctgattgat gct                                           23

<210> SEQ ID NO 179
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 179
gacttacttt aacaaccagc caatc                                         25

<210> SEQ ID NO 180
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 180
aatccctacc taagcctagt agcca                                         25

<210> SEQ ID NO 181
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 181
gccatggttt ggctaagacc gcagc                                         25

<210> SEQ ID NO 182
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 182
gtcagtggtg tcacagtccc acata                                         25

<210> SEQ ID NO 183
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 183
acataacccg tcatctgctg ttggt                                         25

<210> SEQ ID NO 184
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 184
gccaataggt tttccgcttg tagtc                                         25
```

<210> SEQ ID NO 185
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 185
gcagagacct cctagtatta gcatt                                         25

<210> SEQ ID NO 186
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 186
ttttctccca taacctagtg aacct                                         25

<210> SEQ ID NO 187
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 187
gaaagtaccc tgggtctttc atccg                                         25

<210> SEQ ID NO 188
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 188
ctttcatccg tattcctgac aggag                                         25

<210> SEQ ID NO 189
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 189
ggagccctga tgtcttaaat tctga                                         25

<210> SEQ ID NO 190
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 190
ccgcggctcg gagcaagcgg tgcag                                         25

<210> SEQ ID NO 191
<211> LENGTH: 25
<212> TYPE: DNA
<213> ORGANISM: Artificial Sequence
<220> FEATURE:

<223> OTHER INFORMATION: Synthetic Probe Sequence for FAM126A

<400> SEQUENCE: 191
ggagcgattc ccattcgagg agttt                                    25

<210> SEQ ID NO 192
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 192
tctcatttta atacaacacc cgcct                                    25

<210> SEQ ID NO 193
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 193
aacacccgcc tcttagaggc agcag                                    25

<210> SEQ ID NO 194
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 194
cagaccagtc cagccaggtc aaggt                                    25

<210> SEQ ID NO 195
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 195
tgtggaccgc acaacggggt gcaca                                    25

<210> SEQ ID NO 196
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 196
taaacgagcc ctggatctgc aaagc                                    25

<210> SEQ ID NO 197
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 197
gtgatcccaa ccttagcaac ataat                                    25

```
<210> SEQ ID NO 198
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 198
tatatgtcag gtgccagtgc tatgg                                    25

<210> SEQ ID NO 199
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 199
ataccattta ttaccacttc tcagt                                    25

<210> SEQ ID NO 200
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 200
gaggctgtaa ctctggttgt cgaaa                                    25

<210> SEQ ID NO 201
<211> LENGTH: 21
<212> TYPE: DNA
<213> ORGANISM: Artificial Sequence
<220> FEATURE:
<223> OTHER INFORMATION: Synthetic Probe Sequence for PHC1

<400> SEQUENCE: 201
acctcctcac ctgttgtagc c                                        21

<210> SEQ ID NO 202
<211> LENGTH: 25
<212> TYPE: DNA
<213> ORGANISM: Artificial Sequence
<220> FEATURE:
<223> OTHER INFORMATION: Synthetic Probe Sequence for PHC1

<400> SEQUENCE: 202
tttcacgtac cttaatccaa tcttt                                    25

<210> SEQ ID NO 203
<211> LENGTH: 25
<212> TYPE: DNA
<213> ORGANISM: Artificial Sequence
<220> FEATURE:
<223> OTHER INFORMATION: Synthetic Probe Sequence for PHC1

<400> SEQUENCE: 203
agaactagga ctgctcagcc ttatc                                    25

<210> SEQ ID NO 204
<211> LENGTH: 25
<212> TYPE: DNA
<213> ORGANISM: Artificial Sequence
<220> FEATURE:
<223> OTHER INFORMATION: Synthetic Probe Sequence for PHC1
```

<400> SEQUENCE: 204
gcccaggtct taattctcca agagg                                     25

<210> SEQ ID NO 205
<211> LENGTH: 25
<212> TYPE: DNA
<213> ORGANISM: Artificial Sequence
<220> FEATURE:
<223> OTHER INFORMATION: Synthetic Probe Sequence for PHC1

<400> SEQUENCE: 205
ggtggaatgt caggttgcct gccca                                     25

<210> SEQ ID NO 206
<211> LENGTH: 25
<212> TYPE: DNA
<213> ORGANISM: Artificial Sequence
<220> FEATURE:
<223> OTHER INFORMATION: Synthetic Probe Sequence for PHC1

<400> SEQUENCE: 206
agggtttttc tagcttgtgt gacag                                     25

<210> SEQ ID NO 207
<211> LENGTH: 25
<212> TYPE: DNA
<213> ORGANISM: Artificial Sequence
<220> FEATURE:
<223> OTHER INFORMATION: Synthetic Probe Sequence for PHC1

<400> SEQUENCE: 207
ttgtcactta ctcccttgtg attga                                     25

<210> SEQ ID NO 208
<211> LENGTH: 25
<212> TYPE: DNA
<213> ORGANISM: Artificial Sequence
<220> FEATURE:
<223> OTHER INFORMATION: Synthetic Probe Sequence for PHC1

<400> SEQUENCE: 208
tgattgaatt ttttctcctg catcc                                     25

<210> SEQ ID NO 209
<211> LENGTH: 25
<212> TYPE: DNA
<213> ORGANISM: Artificial Sequence
<220> FEATURE:
<223> OTHER INFORMATION: Synthetic Probe Sequence for PHC1

<400> SEQUENCE: 209
agagacttgg ttggcatctt ctgct                                     25

<210> SEQ ID NO 210
<211> LENGTH: 25
<212> TYPE: DNA
<213> ORGANISM: Artificial Sequence
<220> FEATURE:
<223> OTHER INFORMATION: Synthetic Probe Sequence for PHC1

<400> SEQUENCE: 210
ggcacatgtg gctgttgtca ttctt                                     25

<210> SEQ ID NO 211
<211> LENGTH: 25

```
<212> TYPE: DNA
<213> ORGANISM: Artificial Sequence
<220> FEATURE:
<223> OTHER INFORMATION: Synthetic Probe Sequence for PHC1

<400> SEQUENCE: 211
tgttcccctc caatttatgt tattt                                              25

<210> SEQ ID NO 212
<211> LENGTH: 25
<212> TYPE: DNA
<213> ORGANISM: Artificial Sequence
<220> FEATURE:
<223> OTHER INFORMATION: Synthetic Probe Sequence for PHC1

<400> SEQUENCE: 212
gtacctgcct taggcactat tcctt                                              25

<210> SEQ ID NO 213
<211> LENGTH: 22
<212> TYPE: DNA
<213> ORGANISM: Artificial Sequence
<220> FEATURE:
<223> OTHER INFORMATION: Synthetic Probe Sequence for CHML

<400> SEQUENCE: 213
cctctggctg cttatcatca cc                                                 22

<210> SEQ ID NO 214
<211> LENGTH: 25
<212> TYPE: DNA
<213> ORGANISM: Artificial Sequence
<220> FEATURE:
<223> OTHER INFORMATION: Synthetic Probe Sequence for CHML

<400> SEQUENCE: 214
gcaactttga cttagttcat gctat                                              25

<210> SEQ ID NO 215
<211> LENGTH: 25
<212> TYPE: DNA
<213> ORGANISM: Artificial Sequence
<220> FEATURE:
<223> OTHER INFORMATION: Synthetic Probe Sequence for CHML

<400> SEQUENCE: 215
ctgttttaat tgcatgtgtc cttat                                              25

<210> SEQ ID NO 216
<211> LENGTH: 25
<212> TYPE: DNA
<213> ORGANISM: Artificial Sequence
<220> FEATURE:
<223> OTHER INFORMATION: Synthetic Probe Sequence for CHML

<400> SEQUENCE: 216
gtgtccttat agcagcagca ttgtg                                              25

<210> SEQ ID NO 217
<211> LENGTH: 25
<212> TYPE: DNA
<213> ORGANISM: Artificial Sequence
<220> FEATURE:
<223> OTHER INFORMATION: Synthetic Probe Sequence for CHML

<400> SEQUENCE: 217
```
gcagcattgt gtattagtag ccttt                                              25

<210> SEQ ID NO 218
<211> LENGTH: 25
<212> TYPE: DNA
<213> ORGANISM: Artificial Sequence
<220> FEATURE:
<223> OTHER INFORMATION: Synthetic Probe Sequence for CHML

<400> SEQUENCE: 218
agggctttat aactgatctt ttgac                                              25

<210> SEQ ID NO 219
<211> LENGTH: 25
<212> TYPE: DNA
<213> ORGANISM: Artificial Sequence
<220> FEATURE:
<223> OTHER INFORMATION: Synthetic Probe Sequence for CHML

<400> SEQUENCE: 219
gatcttttga catactcact ttgag                                              25

<210> SEQ ID NO 220
<211> LENGTH: 25
<212> TYPE: DNA
<213> ORGANISM: Artificial Sequence
<220> FEATURE:
<223> OTHER INFORMATION: Synthetic Probe Sequence for CHML

<400> SEQUENCE: 220
cactttgagt ggcatatgcc cagga                                              25

<210> SEQ ID NO 221
<211> LENGTH: 25
<212> TYPE: DNA
<213> ORGANISM: Artificial Sequence
<220> FEATURE:
<223> OTHER INFORMATION: Synthetic Probe Sequence for CHML

<400> SEQUENCE: 221
aagttttcta gcagttccac tcaga                                              25

<210> SEQ ID NO 222
<211> LENGTH: 25
<212> TYPE: DNA
<213> ORGANISM: Artificial Sequence
<220> FEATURE:
<223> OTHER INFORMATION: Synthetic Probe Sequence for CHML

<400> SEQUENCE: 222
gttccactca gataacttta agggg                                              25

<210> SEQ ID NO 223
<211> LENGTH: 25
<212> TYPE: DNA
<213> ORGANISM: Artificial Sequence
<220> FEATURE:
<223> OTHER INFORMATION: Synthetic Probe Sequence for CHML

<400> SEQUENCE: 223
tggtgtattg ctagtgctat cacag                                              25

<210> SEQ ID NO 224
<211> LENGTH: 25
<212> TYPE: DNA
<213> ORGANISM: Artificial Sequence

```
<220> FEATURE:
<223> OTHER INFORMATION: Synthetic Probe Sequence for CHML

<400> SEQUENCE: 224
attgtgttta ctgatacatg tgaaa                                              25

<210> SEQ ID NO 225
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 225
tctagtcctt taatgagcat gaatt                                              25

<210> SEQ ID NO 226
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 226
tatacttcta catttgttgc ttagt                                              25

<210> SEQ ID NO 227
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 227
atattgtctt ctatactttg taact                                              25

<210> SEQ ID NO 228
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 228
atttcacgta ttgttgcttt ctctt                                              25

<210> SEQ ID NO 229
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 229
gttgctttct cttatatgga actta                                              25

<210> SEQ ID NO 230
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 230
ggaacttatt gtgtacctct tacct                                              25
```

```
<210> SEQ ID NO 231
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 231
gtattcctag agtttacatt cctaa                                            25

<210> SEQ ID NO 232
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 232
acgacgactt tggctatttt tgtgt                                            25

<210> SEQ ID NO 233
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 233
gttccctacc ttcttaaggc tatgg                                            25

<210> SEQ ID NO 234
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 234
atttgtgtaa atgttctcca tatgt                                            25

<210> SEQ ID NO 235
<211> LENGTH: 25
<212> TYPE: DNA
<213> ORGANISM: Artificial Sequence
<220> FEATURE:
<223> OTHER INFORMATION: Synthetic Probe Sequence for FAM126A

<400> SEQUENCE: 235
caagtgttgc ctcttgtttt attga                                            25

<210> SEQ ID NO 236
<211> LENGTH: 22
<212> TYPE: DNA
<213> ORGANISM: Artificial Sequence
<220> FEATURE:
<223> OTHER INFORMATION: Synthetic Probe Sequence for ST8SIA4

<400> SEQUENCE: 236
actgctcttg accactgaca ca                                               22

<210> SEQ ID NO 237
<211> LENGTH: 25
<212> TYPE: DNA
<213> ORGANISM: Artificial Sequence
<220> FEATURE:
<223> OTHER INFORMATION: Synthetic Probe Sequence for ST8SIA4
```

```
<400> SEQUENCE: 237
tttattttgc acggctctaa acctc                                          25

<210> SEQ ID NO 238
<211> LENGTH: 25
<212> TYPE: DNA
<213> ORGANISM: Artificial Sequence
<220> FEATURE:
<223> OTHER INFORMATION: Synthetic Probe Sequence for ST8SIA4

<400> SEQUENCE: 238
taaacctcca tgttattttc cagtg                                          25

<210> SEQ ID NO 239
<211> LENGTH: 25
<212> TYPE: DNA
<213> ORGANISM: Artificial Sequence
<220> FEATURE:
<223> OTHER INFORMATION: Synthetic Probe Sequence for ST8SIA4

<400> SEQUENCE: 239
ggtgtagaag gtaccagcta aagtg                                          25

<210> SEQ ID NO 240
<211> LENGTH: 25
<212> TYPE: DNA
<213> ORGANISM: Artificial Sequence
<220> FEATURE:
<223> OTHER INFORMATION: Synthetic Probe Sequence for ST8SIA4

<400> SEQUENCE: 240
agatgttcca tgtcatcaga gatgg                                          25

<210> SEQ ID NO 241
<211> LENGTH: 25
<212> TYPE: DNA
<213> ORGANISM: Artificial Sequence
<220> FEATURE:
<223> OTHER INFORMATION: Synthetic Probe Sequence for ST8SIA4

<400> SEQUENCE: 241
ggtaccaaag attacacttg tgttt                                          25

<210> SEQ ID NO 242
<211> LENGTH: 25
<212> TYPE: DNA
<213> ORGANISM: Artificial Sequence
<220> FEATURE:
<223> OTHER INFORMATION: Synthetic Probe Sequence for ST8SIA4

<400> SEQUENCE: 242
acttgtgttt ctacacagca aacca                                          25

<210> SEQ ID NO 243
<211> LENGTH: 25
<212> TYPE: DNA
<213> ORGANISM: Artificial Sequence
<220> FEATURE:
<223> OTHER INFORMATION: Synthetic Probe Sequence for ST8SIA4

<400> SEQUENCE: 243
gctattaatg tgaaagttgt ctcta                                          25

<210> SEQ ID NO 244
```

```
<211> LENGTH: 25
<212> TYPE: DNA
<213> ORGANISM: Artificial Sequence
<220> FEATURE:
<223> OTHER INFORMATION: Synthetic Probe Sequence for ST8SIA4

<400> SEQUENCE: 244
atgtttttca cacctttttgc attac                                            25

<210> SEQ ID NO 245
<211> LENGTH: 25
<212> TYPE: DNA
<213> ORGANISM: Artificial Sequence
<220> FEATURE:
<223> OTHER INFORMATION: Synthetic Probe Sequence for ST8SIA4

<400> SEQUENCE: 245
ttttcacacc ttttgcatta cataa                                             25

<210> SEQ ID NO 246
<211> LENGTH: 25
<212> TYPE: DNA
<213> ORGANISM: Artificial Sequence
<220> FEATURE:
<223> OTHER INFORMATION: Synthetic Probe Sequence for ST8SIA4

<400> SEQUENCE: 246
aattttgtgg aagcattttg ccctt                                             25

<210> SEQ ID NO 247
<211> LENGTH: 25
<212> TYPE: DNA
<213> ORGANISM: Artificial Sequence
<220> FEATURE:
<223> OTHER INFORMATION: Synthetic Probe Sequence for ST8SIA4

<400> SEQUENCE: 247
ggaagcattt tgcccttag aataa                                              25

<210> SEQ ID NO 248
<211> LENGTH: 26
<212> TYPE: DNA
<213> ORGANISM: Artificial Sequence
<220> FEATURE:
<223> OTHER INFORMATION: Synthetic Probe Sequence for CAV1

<400> SEQUENCE: 248
tagataacaa gacctcagtg ccttcc                                            26

<210> SEQ ID NO 249
<211> LENGTH: 25
<212> TYPE: DNA
<213> ORGANISM: Artificial Sequence
<220> FEATURE:
<223> OTHER INFORMATION: Synthetic Probe Sequence for CAV1

<400> SEQUENCE: 249
gaatttcacc tgtaaacctg agtcg                                             25

<210> SEQ ID NO 250
<211> LENGTH: 25
<212> TYPE: DNA
<213> ORGANISM: Artificial Sequence
<220> FEATURE:
<223> OTHER INFORMATION: Synthetic Probe Sequence for CAV1

<400> SEQUENCE: 250
```
cagaaagctg cctggtatat ccaaa                                                 25

<210> SEQ ID NO 251
<211> LENGTH: 25
<212> TYPE: DNA
<213> ORGANISM: Artificial Sequence
<220> FEATURE:
<223> OTHER INFORMATION: Synthetic Probe Sequence for CAV1

<400> SEQUENCE: 251
tattcctcct gctcatattg tgatt                                                 25

<210> SEQ ID NO 252
<211> LENGTH: 25
<212> TYPE: DNA
<213> ORGANISM: Artificial Sequence
<220> FEATURE:
<223> OTHER INFORMATION: Synthetic Probe Sequence for CAV1

<400> SEQUENCE: 252
gtcttcctga cactttaatt accaa                                                 25

<210> SEQ ID NO 253
<211> LENGTH: 25
<212> TYPE: DNA
<213> ORGANISM: Artificial Sequence
<220> FEATURE:
<223> OTHER INFORMATION: Synthetic Probe Sequence for CAV1

<400> SEQUENCE: 253
taccaacctg ttacctactt tgact                                                 25

<210> SEQ ID NO 254
<211> LENGTH: 25
<212> TYPE: DNA
<213> ORGANISM: Artificial Sequence
<220> FEATURE:
<223> OTHER INFORMATION: Synthetic Probe Sequence for CAV1

<400> SEQUENCE: 254
gttacctact ttgactttt gcatt                                                  25

<210> SEQ ID NO 255
<211> LENGTH: 25
<212> TYPE: DNA
<213> ORGANISM: Artificial Sequence
<220> FEATURE:
<223> OTHER INFORMATION: Synthetic Probe Sequence for CAV1

<400> SEQUENCE: 255
atgtgctata ctgcatactt tttaa                                                 25

<210> SEQ ID NO 256
<211> LENGTH: 25
<212> TYPE: DNA
<213> ORGANISM: Artificial Sequence
<220> FEATURE:
<223> OTHER INFORMATION: Synthetic Probe Sequence for CAV1

<400> SEQUENCE: 256
aactgtgtat tccaagacat gtctg                                                 25

<210> SEQ ID NO 257
<211> LENGTH: 25
<212> TYPE: DNA

```
<213> ORGANISM: Artificial Sequence
<220> FEATURE:
<223> OTHER INFORMATION: Synthetic Probe Sequence for CAV1

<400> SEQUENCE: 257
catagatgct tagtccctca tgcaa                                      25

<210> SEQ ID NO 258
<211> LENGTH: 25
<212> TYPE: DNA
<213> ORGANISM: Artificial Sequence
<220> FEATURE:
<223> OTHER INFORMATION: Synthetic Probe Sequence for CAV1

<400> SEQUENCE: 258 aatttttat catgcatgtc ctgta                                       25

<210> SEQ ID NO 259
<211> LENGTH: 25
<212> TYPE: DNA
<213> ORGANISM: Artificial Sequence
<220> FEATURE:
<223> OTHER INFORMATION: Synthetic Probe Sequence for CAV1

<400> SEQUENCE: 259
taaaggttac aagcctgcac aataa                                      25

<210> SEQ ID NO 260
<211> LENGTH: 23
<212> TYPE: DNA
<213> ORGANISM: Artificial Sequence
<220> FEATURE:
<223> OTHER INFORMATION: Synthetic Probe Sequence for RPL23A

<400> SEQUENCE: 260
actggctcct gattacgatg ctt                                        23

<210> SEQ ID NO 261
<211> LENGTH: 25
<212> TYPE: DNA
<213> ORGANISM: Artificial Sequence
<220> FEATURE:
<223> OTHER INFORMATION: Synthetic Probe Sequence for TPT1

<400> SEQUENCE: 261
cataactggc ttctgcttgt catcc                                      25

<210> SEQ ID NO 262
<211> LENGTH: 22
<212> TYPE: DNA
<213> ORGANISM: Artificial Sequence
<220> FEATURE:
<223> OTHER INFORMATION: Synthetic Probe Sequence for EEF1A1

<400> SEQUENCE: 262
ccagcagcaa caatcaggac ag                                         22

<210> SEQ ID NO 263
<211> LENGTH: 20
<212> TYPE: DNA
<213> ORGANISM: Artificial Sequence
<220> FEATURE:
<223> OTHER INFORMATION: Synthetic Probe Sequence for SRSF3

<400> SEQUENCE: 263
ttccactctt acacggcagc                                            20
```

<210> SEQ ID NO 264
<211> LENGTH: 23
<212> TYPE: DNA
<213> ORGANISM: Artificial Sequence
<220> FEATURE:
<223> OTHER INFORMATION: Synthetic Probe Sequence for TUT1

<400> SEQUENCE: 264
cctgtggtca agttctgtca tcg    23

<210> SEQ ID NO 265
<211> LENGTH: 21
<212> TYPE: DNA
<213> ORGANISM: Artificial Sequence
<220> FEATURE:
<223> OTHER INFORMATION: Synthetic Probe Sequence for HNRNPC

<400> SEQUENCE: 265
ctgctgctct gctcctcttc t    21

<210> SEQ ID NO 266
<211> LENGTH: 23
<212> TYPE: DNA
<213> ORGANISM: Artificial Sequence
<220> FEATURE:
<223> OTHER INFORMATION: Synthetic Probe Sequence for HUWE1

<400> SEQUENCE: 266
tcctcttcct cctcatcctc act    23

<210> SEQ ID NO 267
<211> LENGTH: 20
<212> TYPE: DNA
<213> ORGANISM: Artificial Sequence
<220> FEATURE:
<223> OTHER INFORMATION: Synthetic Probe Sequence for WDR90

<400> SEQUENCE: 267
tggtcactca gcacacggaa    20

<210> SEQ ID NO 268
<211> LENGTH: 21
<212> TYPE: DNA
<213> ORGANISM: Artificial Sequence
<220> FEATURE:
<223> OTHER INFORMATION: Synthetic Probe Sequence for MATR3

<400> SEQUENCE: 268
tgaccagaca gagcaggaac c    21

<210> SEQ ID NO 269
<211> LENGTH: 22
<212> TYPE: DNA
<213> ORGANISM: Artificial Sequence
<220> FEATURE:
<223> OTHER INFORMATION: Synthetic Probe Sequence for SMARCA4

<400> SEQUENCE: 269
ccttcctcat catcgtgcct ct    22

<210> SEQ ID NO 270
<211> LENGTH: 18
<212> TYPE: DNA
<213> ORGANISM: Artificial Sequence
<220> FEATURE:

<223> OTHER INFORMATION: Synthetic Sense Primer for THSD7A

<400> SEQUENCE: 270
gcctgttatg actggaaa                                                    18

<210> SEQ ID NO 271
<211> LENGTH: 18
<212> TYPE: DNA
<213> ORGANISM: Artificial Sequence
<220> FEATURE:
<223> OTHER INFORMATION: Synthetic Anti-sense Primer for THSD7A

<400> SEQUENCE: 271
ctgtcaactt cttctcca                                                    18

<210> SEQ ID NO 272
<211> LENGTH: 18
<212> TYPE: DNA
<213> ORGANISM: Artificial Sequence
<220> FEATURE:
<223> OTHER INFORMATION: Synthetic Sense Primer for MET

<400> SEQUENCE: 272
ccttgaacag aatcactg                                                    18

<210> SEQ ID NO 273
<211> LENGTH: 19
<212> TYPE: DNA
<213> ORGANISM: Artificial Sequence
<220> FEATURE:
<223> OTHER INFORMATION: Synthetic Anti-sense Primer for MET

<400> SEQUENCE: 273
ccatgtttca tgtatggta                                                   19

<210> SEQ ID NO 274
<211> LENGTH: 18
<212> TYPE: DNA
<213> ORGANISM: Artificial Sequence
<220> FEATURE:
<223> OTHER INFORMATION: Synthetic Sense Primer for FAM126A

<400> SEQUENCE: 274
gcttgtagtc tccaagaa                                                    18

<210> SEQ ID NO 275
<211> LENGTH: 20
<212> TYPE: DNA
<213> ORGANISM: Artificial Sequence
<220> FEATURE:
<223> OTHER INFORMATION: Synthetic Anti-sense Primer for FAM126A

<400> SEQUENCE: 275
ggacagagta atgctaatac                                                  20

<210> SEQ ID NO 276
<211> LENGTH: 18
<212> TYPE: DNA
<213> ORGANISM: Artificial Sequence
<220> FEATURE:
<223> OTHER INFORMATION: Synthetic Sense Primer for PHC1

<400> SEQUENCE: 276
gacagcacat gtggtaaa                                                    18

```
<210> SEQ ID NO 277
<211> LENGTH: 20
<212> TYPE: DNA
<213> ORGANISM: Artificial Sequence
<220> FEATURE:
<223> OTHER INFORMATION: Synthetic Anti-sense Primer for PHC1

<400> SEQUENCE: 277
cacagactgc atatagaagg                                          20

<210> SEQ ID NO 278
<211> LENGTH: 20
<212> TYPE: DNA
<213> ORGANISM: Artificial Sequence
<220> FEATURE:
<223> OTHER INFORMATION: Synthetic Sense Primer for RAB31

<400> SEQUENCE: 278
ctcagatatt agggaggttc                                          20

<210> SEQ ID NO 279
<211> LENGTH: 18
<212> TYPE: DNA
<213> ORGANISM: Artificial Sequence
<220> FEATURE:
<223> OTHER INFORMATION: Synthetic Anti-sense Primer for RAB31

<400> SEQUENCE: 279
gctgattcct tgaaagag                                            18

<210> SEQ ID NO 280
<211> LENGTH: 18
<212> TYPE: DNA
<213> ORGANISM: Artificial Sequence
<220> FEATURE:
<223> OTHER INFORMATION: Synthetic Sense Primer for ST8SIA4

<400> SEQUENCE: 280
gcacaatgta gaaggttg                                            18

<210> SEQ ID NO 281
<211> LENGTH: 19
<212> TYPE: DNA
<213> ORGANISM: Artificial Sequence
<220> FEATURE:
<223> OTHER INFORMATION: Synthetic Anti-sense Primer for ST8SIA4

<400> SEQUENCE: 281
caagcacata gtgtatgac                                           19

<210> SEQ ID NO 282
<211> LENGTH: 18
<212> TYPE: DNA
<213> ORGANISM: Artificial Sequence
<220> FEATURE:
<223> OTHER INFORMATION: Synthetic Sense Primer for CHML

<400> SEQUENCE: 282
ctccaaatcc agaagaca                                            18

<210> SEQ ID NO 283
<211> LENGTH: 20
<212> TYPE: DNA
<213> ORGANISM: Artificial Sequence
<220> FEATURE:
<223> OTHER INFORMATION: Synthetic Anti-sense Primer for CHML
```

```
<400> SEQUENCE: 283
ggccattact acattattgg                                              20

<210> SEQ ID NO 284
<211> LENGTH: 20
<212> TYPE: DNA
<213> ORGANISM: Artificial Sequence
<220> FEATURE:
<223> OTHER INFORMATION: Synthetic Sense Primer for CAV1

<400> SEQUENCE: 284
ctgtgcctga atatttgtta                                              20

<210> SEQ ID NO 285
<211> LENGTH: 20
<212> TYPE: DNA
<213> ORGANISM: Artificial Sequence
<220> FEATURE:
<223> OTHER INFORMATION: Synthetic Anti-sense Primer for CAV1

<400> SEQUENCE: 285
ctgagttaga ccctatttga                                              20

<210> SEQ ID NO 286
<211> LENGTH: 18
<212> TYPE: DNA
<213> ORGANISM: Artificial Sequence
<220> FEATURE:
<223> OTHER INFORMATION: Synthetic Sense Primer for RPL23A

<400> SEQUENCE: 286
gagagaagaa ggcatatg                                                18

<210> SEQ ID NO 287
<211> LENGTH: 18
<212> TYPE: DNA
<213> ORGANISM: Artificial Sequence
<220> FEATURE:
<223> OTHER INFORMATION: Synthetic Anti-sense Primer for RPL23A

<400> SEQUENCE: 287
tggactcagt ttagatga                                                18

<210> SEQ ID NO 288
<211> LENGTH: 21
<212> TYPE: DNA
<213> ORGANISM: Artificial Sequence
<220> FEATURE:
<223> OTHER INFORMATION: Synthetic Sense Primer for TPT1

<400> SEQUENCE: 288
ggcaattatt ttggatctat c                                            21

<210> SEQ ID NO 289
<211> LENGTH: 18
<212> TYPE: DNA
<213> ORGANISM: Artificial Sequence
<220> FEATURE:
<223> OTHER INFORMATION: Synthetic Anti-sense Primer for TPT1

<400> SEQUENCE: 289
cagtcccatt tgtcttaa                                                18

<210> SEQ ID NO 290
<211> LENGTH: 18
```

```
<212> TYPE: DNA
<213> ORGANISM: Artificial Sequence
<220> FEATURE:
<223> OTHER INFORMATION: Synthetic Sense Primer for EEF1A1

<400> SEQUENCE: 290
caggacacag agacttta                                                18

<210> SEQ ID NO 291
<211> LENGTH: 18
<212> TYPE: DNA
<213> ORGANISM: Artificial Sequence
<220> FEATURE:
<223> OTHER INFORMATION: Synthetic Anti-sense Primer for EEF1A1

<400> SEQUENCE: 291
cagcttcaaa ttcaccaa                                                18

<210> SEQ ID NO 292
<211> LENGTH: 18
<212> TYPE: DNA
<213> ORGANISM: Artificial Sequence
<220> FEATURE:
<223> OTHER INFORMATION: Synthetic Sense Primer for SRSF3

<400> SEQUENCE: 292
cgagagctag atggaaga                                                18

<210> SEQ ID NO 293
<211> LENGTH: 18
<212> TYPE: DNA
<213> ORGANISM: Artificial Sequence
<220> FEATURE:
<223> OTHER INFORMATION: Synthetic Anti-sense Primer for SRSF3

<400> SEQUENCE: 293
ggccacgatt tctacttc                                                18

<210> SEQ ID NO 294
<211> LENGTH: 18
<212> TYPE: DNA
<213> ORGANISM: Artificial Sequence
<220> FEATURE:
<223> OTHER INFORMATION: Synthetic Sense Primer for TUT1

<400> SEQUENCE: 294
ggtgtatcga gtccaaac                                                18

<210> SEQ ID NO 295
<211> LENGTH: 18
<212> TYPE: DNA
<213> ORGANISM: Artificial Sequence
<220> FEATURE:
<223> OTHER INFORMATION: Synthetic Anti-sense Primer for TUT1

<400> SEQUENCE: 295
caggaaacgg gagttatg                                                18

<210> SEQ ID NO 296
<211> LENGTH: 18
<212> TYPE: DNA
<213> ORGANISM: Artificial Sequence
<220> FEATURE:
<223> OTHER INFORMATION: Synthetic Sense Primer for HNRNPC

<400> SEQUENCE: 296
```
caagcagtag agatgaag                                                18

<210> SEQ ID NO 297
<211> LENGTH: 19
<212> TYPE: DNA
<213> ORGANISM: Artificial Sequence
<220> FEATURE:
<223> OTHER INFORMATION: Synthetic Anti-sense Primer for HNRNPC

<400> SEQUENCE: 297
ctccatcttc acattagtc                                               19

<210> SEQ ID NO 298
<211> LENGTH: 18
<212> TYPE: DNA
<213> ORGANISM: Artificial Sequence
<220> FEATURE:
<223> OTHER INFORMATION: Synthetic Sense Primer for HUWE1

<400> SEQUENCE: 298
caaggtctaa tcatgctg                                                18

<210> SEQ ID NO 299
<211> LENGTH: 19
<212> TYPE: DNA
<213> ORGANISM: Artificial Sequence
<220> FEATURE:
<223> OTHER INFORMATION: Synthetic Anti-sense Primer for HUWE1

<400> SEQUENCE: 299
ctgctgggta gaattaaag                                               19

<210> SEQ ID NO 300
<211> LENGTH: 18
<212> TYPE: DNA
<213> ORGANISM: Artificial Sequence
<220> FEATURE:
<223> OTHER INFORMATION: Synthetic Sense Primer for WDR90

<400> SEQUENCE: 300
ctctggagac aaggatgg                                                18

<210> SEQ ID NO 301
<211> LENGTH: 20
<212> TYPE: DNA
<213> ORGANISM: Artificial Sequence
<220> FEATURE:
<223> OTHER INFORMATION: Synthetic Anti-sense Primer for WDR90

<400> SEQUENCE: 301
gacacagatg gtagagattg                                              20

<210> SEQ ID NO 302
<211> LENGTH: 18
<212> TYPE: DNA
<213> ORGANISM: Artificial Sequence
<220> FEATURE:
<223> OTHER INFORMATION: Synthetic Sense Primer for MATR3

<400> SEQUENCE: 302
ggtgagaaag acacaaag                                                18

<210> SEQ ID NO 303
<211> LENGTH: 19
<212> TYPE: DNA
<213> ORGANISM: Artificial Sequence

```
<220> FEATURE:
<223> OTHER INFORMATION: Synthetic Anti-sense Primer for MATR3

<400> SEQUENCE: 303
ctgcttcttc ttcatctac                                                    19

<210> SEQ ID NO 304
<211> LENGTH: 18
<212> TYPE: DNA
<213> ORGANISM: Artificial Sequence
<220> FEATURE:
<223> OTHER INFORMATION: Synthetic Sense Primer for SMARCA4

<400> SEQUENCE: 304
gtacctcatg gagcacaa                                                     18

<210> SEQ ID NO 305
<211> LENGTH: 19
<212> TYPE: DNA
<213> ORGANISM: Artificial Sequence
<220> FEATURE:
<223> OTHER INFORMATION: Synthetic Anti-sense Primer for SMARCA4

<400> SEQUENCE: 305
ccttgtaaga caccttcac                                                    19

<210> SEQ ID NO 306
<211> LENGTH: 114
<212> TYPE: PRT
<213> ORGANISM: Artificial Sequence
<220> FEATURE:
<223> OTHER INFORMATION: Synthetic light chain variable region of anti
      c-Met antibody

<400> SEQUENCE: 306

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg
```

BIOMARKER FOR PREDICTING EFFECT OF AN ANTI-C-MET ANTIBODY

CROSS-REFERENCE TO RELATED APPLICATIONS

This application claims the benefit of Korean Patent Application No. 10-2014-0040146 filed on Apr. 3, 2014, and Korean Patent Application No. 10-2015-0046413, filed on Apr. 1, 2015, in the Korean Intellectual Property Office, the entire disclosures of which are hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: One 176,832 byte ASCII (Text) file named "719557_ST25.TXT" created Apr. 1, 2015.

BACKGROUND OF THE INVENTION

1. Field

A biomarker for predicting an effect of an anti-c-Met antibody and/or selecting a subject for application of an anti-c-Met antibody, a reference (or control) marker for comparison of gene expression level, a method of predicting an effect of an anti-c-Met antibody and/or selecting a subject for application of an anti-c-Met antibody including measuring a level of the biomarker in a biological sample, and a method of preventing and/or treating a cancer including administering an anti-c-Met antibody to the selected subject, are provided.

2. Description of the Related Art

After the U.S. Food & Drug Association (FDA) approved Herceptin, a targeting drug produced by Genentech Inc., various individual therapies and markers for selecting an applicable subject have been developed. In the case of Herceptin, a subject suitable for application can be selected through the expression amount of HER2 growth factor receptor expressed on cell membrane of cancer cells. After development of the IHC (immunohistochemistry) assay, various assays, such as FISH (fluorescence in situ hybridization), CISH (chromogenic in situ hybridization), and the like, have been employed for selecting a suitable subject. Thereafter, EGFR mutation as an selection marker of a subject (lung & pancreatic cancer patient) for application of Erlotinib, KRAS mutation as an selection marker of a subject (colorectal cancer) for application of Vectibix and Erbitux, and the like, have been approved by FDA.

For an anticancer agent targeting c-Met protein, markers for a subject on which the c-Met targeting agent can exhibit its effect well have been studied. Currently, a c-Met targeting agent, MetMab, is a subject of a phase III clinical trial, wherein ventana IHC assay (sp44: c-met primary antibody, rabbit monoclonal) has been used as a co-diagnosing method for selecting a suitable subject. However, such diagnosing method is limited in its use as a general diagnostic due to a low accuracy. In addition, such IHC assay has a weak point that the results depend on individual properties, lesion, propensity of pathologist, and the like.

In order to increase the effect of c-Met targeting anticancer agent, development of biomarkers for predicting the effect of the targeting anticancer agent or selecting a subject suitable for application of the targeting anticancer agent is needed.

BRIEF SUMMARY OF THE INVENTION

An embodiment provides a biomarker for predicting an effect of an anti-c-Met antibody on a subject or selecting a subject for application of the anti-c-Met antibody (e.g., administration of or treatment with an anti-c-Met antibody).

Another embodiment provides a composition and a kit for predicting an effect of an anti-c-Met antibody on a subject or selecting a subject for application of the anti-c-Met antibody including a molecule or composition for detecting the biomarker.

Another embodiment provides a reference (or control) marker for comparison of a level of the biomarker for predicting an effect of an anti-c-Met antibody on a subject or selecting a subject for application of the anti-c-Met antibody.

Another embodiment provides a method of predicting an effect of an anti-c-Met antibody on a subject or selecting a subject for application of the anti-c-Met antibody (e.g., administration of or treatment with an anti-c-Met antibody), including determining the presence and/or the level of the biomarker (e.g., presence and/or amount of the biomarker) in a biological sample from a subject. The method comprises, in an embodiment, determining the expression level of a biomarker in a biological sample from a subject and comparing the level of the biomarker to that of a reference marker, wherein the biomarker is at least one selected from the group consisting of THSD7A, MET, RAB31, FAM126A, PHC1, CHML, ST8SIA4, and CAV1 and the reference marker is at least one selected from the group consisting of EEF1A1, RPL23A, TPT1, HUWE1, MATR3, SRSF3, HNRNPC, SMARCA4, WDR90, and TUT1; and determining that administration of the anti-c-Met antibody or antigen thereof will have an effect or is appropriate for a subject when, in the case of CAV1, FAM126A, MET, RAB31, ST8SIA4, and/or THSD7A, the level of the biomarker is higher than that of the reference marker or reference sample; and in the case of CMHL and/or PHC1, the level of the biomarker is lower than that of the reference marker or reference sample.

Another embodiment provides a use of the biomarker for predicting an effect of an anti-c-Met antibody on a subject or selecting a subject for application of the anti-c-Met antibody (e.g., administration of or treatment with an anti-c-Met antibody).

Another embodiment provides a method of preventing and/or treating a cancer including administering an anti-c-Met antibody to the selected subject.

Still another embodiment provides a method of c-Met inhibition, including administering an anti-c-Met antibody to the selected subject.

DETAILED DESCRIPTION OF THE INVENTION

Figure 1A:
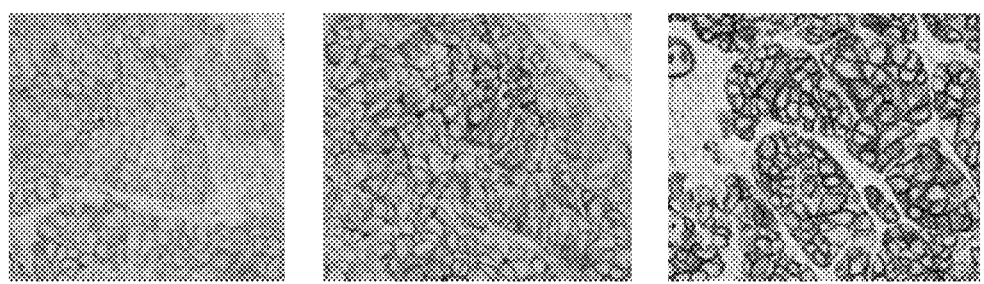
FIG. 1A includes images obtained by Ventana MET IHC assay for mouse xenograft models.
Figure 1A:
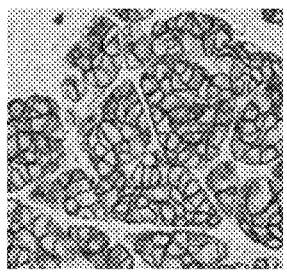
Figure 1A:
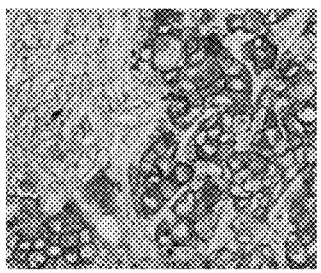
Figure 1A:
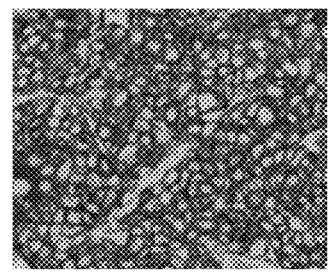

Expression levels of genes in a group on which an anti-c-Met antibody has effects (hereinafter, a responding or efficacy group) or a group on which an anti-c-Met antibody has no effect (hereinafter, a non-responding or non-efficacy group) are compared, and genes showing a great difference in expression level between a responding group and a non-responding group are selected. The selected genes or proteins encoded by the genes are suggested as biomarkers for predicting an effect of an anti-c-Met antibody. In addition, genes showing a small or no difference in expression level between different cells or individual cells of a same cell line are selected, and the selected genes or proteins encoded by the genes are suggested as reference or control markers for comparison of expression level of a target gene and/or a target protein.

An embodiment provides a use of at least one gene showing a difference in expression level between a responding group and a non-responding group for an anti-c-Met antibody as a biomarker for predicting an effect of an anti-c-Met antibody on a subject or selecting a selecting a subject for application of the anti-c-Met antibody.

In one embodiment, the biomarker may be at least one selected from the group consisting of THSD7A, MET, RAB31, FAM126A, PHC1, CHML, ST8SIA4, and CAV1. The biomarker may be at least one selected from the group consisting of full-length (entire) DNAs, cDNAs, and mRNAs of the above described genes and proteins encoded by the genes. The information of the genes usable as a biomarker is summarized following Table 1:

TABLE 1

| Gene | Entrez Gene Name | NCBI Accession No. (mRNA) |
|---|---|---|
| THSD7A | thrombospondin, type I, domain containing 7A | NM_015204 |
| MET | met proto-oncogene (hepatocyte growth factor receptor) | NM_001127500.1, NM_000245.2 |
| RAB31 | RAB31, member RAS oncogene family | NM_006868.3 |
| FAM126A | family with sequence similarity 126, member A | NM_032581.3 |
| PHC1 | polyhomeotic homolog 1 (*Drosophila*) | NM_004426.2 |
| CHML | choroideremia-like (Rab escort protein 2) | NM_001821.3 |
| ST8SIA4 | ST8 alpha-N-acetyl-neuraminide alpha-2,8-sialyltransferase 4 | NM_005668.5 |
| CAV1 | caveolin 1, caveolae protein, 22 kDa | NM_001753.4, NM_001172895.1, NM_001172896.1, NM_001172897.1 |

The biomarkers can be ranked in descending order from a gene showing a greater difference to a gene showing a less great difference in expression level, as follows: THSD7A>MET>RAB31>FAM126A>PHC1>CHML> ST8SIA4>CAV1. In order to carry out more accurate prediction of the effect or selection of the applicable subject, among the genes, a gene which shows greater difference in expression level can be more preferentially selected for use as a biomarker. Therefore, in an embodiment, the biomarker may comprise a gene preferentially selected as above or in addition to the preferentially selected gene, further comprise at least one selected from the group consisting of the rest of the genes.

In one embodiment, the biomarker may comprise:
1) THSD7A;
2) a combination of THSD7A and at least one selected from the group consisting of MET, RAB31, FAM126A, PHC1, CHML, ST8SIA4, and CAV1;
3) MET;
4) a combination of MET and at least one selected from the group consisting of THSD7A, RAB31, FAM126A, PHC1, CHML, ST8SIA4, and CAV1;
5) a combination of THSD7A and MET;
6) a combination of i) a combination of THSD7A and MET (THSD7A+MET) and ii) at least one selected from the group consisting of RAB31, FAM126A, PHC1, CHML, ST8SIA4, and CAV1;
7) RAB31;
8) a combination of RAB31 and at least one selected from the group consisting of THSD7A, MET, FAM126A, PHC1, CHML, ST8SIA4, and CAV1;
9) at least two selected from the group consisting of THSD7A, MET, and RAB31 (wherein, a combination of THSD7A and MET may be excluded);
10) a combination of i) at least two selected from the group consisting of THSD7A, MET, and RAB31 and ii) at least one selected from the group consisting of FAM126A, PHC1, CHML, ST8SIA4, and CAV1;
11) FAM126A;
12) a combination of FAM126A and at least one selected from the group consisting of THSD7A, MET, RAB31, PHC1, CHML, ST8SIA4, and CAV1;
13) at least two selected from the group consisting of THSD7A, MET, RAB31 and FAM126A (wherein, at least two selected from the group consisting of THSD7A, MET, and RAB31 may be excluded); or
14) a combination of i) at least two selected from the group consisting of THSD7A, MET, RAB31 and FAM126A and ii) at least one selected from the group consisting of PHC1, CHML, ST8SIA4, and CAV1.

In another embodiment, a gene showing a slight or no difference in expression level between different type kinds of cells or individual cells of a same kind of cells is found. The gene may be used as a reference (or control) marker for the use in comparing the expression level of a target gene with a reference (or control). The target gene may be any gene whose expression level is measured. For example, the target gene may be the biomarker selected for predicting an effect of an anti-c-Met antibody on a subject or selecting a selecting a subject for application of the anti-c-Met antibody. In this case, the reference marker may be used as a reference for comparison of expression level of the target gene in predicting an effect of an anti-c-Met antibody on a subject or selecting a selecting a subject for application of the anti-c-Met antibody.

In measuring expression level of a target gene, if the expression level of a gene used as a reference for comparison is altered depending on the kinds of cell or individual cells of the same kind of cell, an accurate measurement of expression level of the target gene cannot be achieved; therefore, the selection of an suitable reference marker is very important for exactly measuring expression level of the target gene.

In one embodiment, the reference marker may be selected from endogenous genes which are essential to cell survival. For example, the reference marker may comprise at least one selected from the group consisting of EEF1A1, RPL23A, TPT1, HUWE1, MATR3, SRSF3, HNRNPC, SMARCA4, WDR90, and TUT1. In one embodiment, since the expression amounts of RPL23A, TPT1, MATR3, SRSF3, and HNRNPC are maintained at a very constant level (see Example 1), the reference marker may essentially comprise at least one selected from the group consisting of RPL23A, TPT1, MATR3, SRSF3, and HNRNPC, and optionally further comprise at least one selected from the group consisting of EEF1A1, HUWE1, SMARCA4, WDR90, and TUT1, but not be limited thereto. In one embodiment, the reference marker may comprise RPL23A, TPT1, MATR3, SRSF3, and HNRNPC. Alternatively, the reference marker may comprise TPT1, EEF1M, TUT1, MATR3, and SMARCA4.

The reference marker may comprise at least one selected from the group consisting of full-length DNAs, cDNAs, and mRNAs of the above described gene, and proteins encoded by the gene. In this case, the cell to be used in measuring the expression level may be a lung cancer cell, for example, a lung cancer adenocarcinoma cell, a non-small cell lung cancer cell, etc., but not be limited thereto. The information of the genes useful as a reference marker is summarized in following Table 2:

TABLE 2

| Gene | NCBI Accession No.(mRNA) |
| --- | --- |
| EEF1A1 | NM_001402.5 |
| RPL23A | NM_000984.5 |
| TPT1 | NM_001286272.1, NM_003295.3, NM_001286273.1 |
| HUWE1 | NM_031407.6 |
| MATR3 | NM_199189.2, NM_018834.5, NM_001194954.1, NM_001194955.1, NM_001194956.1, NM_001282278.1 |
| SRSF3 | NM_003017.4, NR_036610.1 |
| HNRNPC | NM_031314.2, NM_001077442.1, NM_004500.3, NM_001077443.1 |
| SMARCA4 | NM_001128849.1, NM_001128844.1, NM_003072.3, NM_001128845.1, NM_001128846.1, NM_001128847.1, NM_001128848.1 |
| WDR90 | NM_145294.4 |
| TUT1 | NM_022830.2 |

Another embodiment provides a method of determining (or evaluating) an expression level of a target gene, using a reference marker as a reference for comparison, wherein the reference marker may be at least one selected from the group consisting of EEF1A1, RPL23A, TPT1, HUWE1, MATR3, SRSF3, HNRNPC, SMARCA4, WDR90, and TUT1. The method of determining (or evaluating) an expression level of a gene may comprise measuring the expression level of a target gene in a biological sample, and comparing the expression level of the target gene to that of the reference marker. The method of determining (or evaluating) an expression level of a gene may further comprise measuring the expression level of a reference marker. The expression level may be measured in a cell or a tissue which is isolated (separated) from a living body, or a gene (DNA or RNA) or protein which is extracted from the cell or tissue. The measurement of the expression level may be carried out by measuring the amount of the gene (e.g., full-length DNA, cDNA, mRNA, etc.) or the protein encoded by the gene in a biological sample separated from a living body.

Another embodiment provides a composition for predicting an effect of an anti-c-Met antibody on a subject (or a responsiveness or sensitivity of a subject to an anti-c-Met antibody) or selecting a selecting a subject for application of the anti-c-Met antibody comprising a molecule or agent for detecting a biomarker or a protein encoded by the biomarker. The composition for predicting an effect of an anti-c-Met antibody on a subject or selecting a selecting a subject for application of the anti-c-Met antibody may further comprise a molecule or agent for detecting a reference marker gene (full-length DNA, cDNA, or mRNA) or a protein encoded by the reference marker gene.

Another embodiment provides a kit for predicting an effect of an anti-c-Met antibody on a subject (or a responsiveness or sensitivity of a subject to an anti-c-Met antibody) or selecting a selecting a subject for application of the anti-c-Met antibody comprising a molecule or agent for detecting a biomarker or a protein encoded the biomarker. The kit for predicting an effect of an anti-c-Met antibody on a subject or selecting a selecting a subject for application of the anti-c-Met antibody may further comprise a molecule or composition for detecting a reference marker gene (full-length DNA, cDNA, or mRNA) or a protein encoded by the reference marker gene.

Another embodiment provides a reference composition or a kit for (determining or evaluating) an expression level of a target gene, comprising a molecule or agent for detecting a reference marker gene (full-length DNA, cDNA, or mRNA) or a protein encoded by the reference marker gene. In one embodiment, when the target gene is the biomarker as described above, the composition or kit can be used for predicting an effect of an anti-c-Met antibody on a subject or selecting a subject for application of the anti-c-Met antibody.

The molecule or agent for detecting a biomarker or a reference marker may be any type typically used for a gene or protein detection assay. For example, the gene or protein detection assay may be performed via an ordinary enzyme reaction, fluorescence, luminescence, and/or radioactivity detection. More particularly, the protein may be detected by a method selected from the group consisting of immunochromatography, immunohistochemistry, enzyme linked immunosorbent assay (ELISA), radioimmunoassay (RIA), enzyme immunoassay (EIA), fluorescence immunoassay (FIA), luminescence immunoassay (LIA), western blotting, microarray, surface plasmon resonance (SPR), flow cytometry assay, and the like, but is not limited thereto. In addition, the gene may be detected by using any ordinary gene (DNA or RNA) detection methods including, but not limited to, an ordinary polymerase chain reaction (PCR; e.g., qPCR, RT-PCR, etc.), FISH (fluorescent in situ hybridization), and/or microarray, using a primer or probe hybridizable with the gene. For example, the molecule or agent for detecting a biomarker or a reference marker may be a primer, probe or aptamer capable of binding (hybridizing) with the gene, an antibody or aptamer specifically recognizing and/or binding to a protein encoded by the gene, or any combination thereof. The primer, probe, aptamer or antibody may be synthetic or recombinant. The primer may be able to detect an entire gene or a gene fragment of about 5 to about 1000 bp, about 10 to about 500 bp, about 20 to about 200 bp, or about 50 to about 200 bp within the biomarker gene or the reference marker gene (full-length DNA, cDNA, or mRNA), and may comprise or consist essentially of a nucleotide sequence hybridizable with (e.g., complementary to) a region of about 5 to about 100 bp, about 5 to about 50 bp, about 5 to about 30 bp, or about 10 to about 25 bp, of 3'-end and/or 5'-end of the entire gene or the gene fragment. The probe or the aptamer capable of hybridizing with the gene may comprise or consist essentially of a nucleotide sequence with a size of from about 5 to about 100 bp, from about 5 to about 50 bp, from about 5 to about 30 bp, or from about 5 to about 25 bp, which is capable of hybridizing with (or complementary to) a fragment (about 5 to about 100 bp, about 5 to about 50 bp, about 5 to about 30 bp, or about 5 to about 25 bp) of the biomarker or a reference marker (full-length DNA, cDNA or mRNA). As used herein, the term "capable of hybridizing" may refer to complementarily binding to a specific region of the gene, with a sequence complementarity of 80% or higher, e.g., 90% or higher, 95% or higher, 98% or higher, 99% or higher, or 100% between the primer, probe or aptamer and the gene region.

Examples of probes and primers useful for detecting a biomarker or a reference marker are illustrated in following Tables 3-5:

TABLE 3

| Gene | Probe Sequence (5'-3') |
|---|---|
| THSD7A | CCTCTTGAACTTGCGTGCCTG (SEQ ID NO: 109) |
| MET | CTTCACTTCGCAGGCAGATTCC (SEQ ID NO: 143) |
| RAB31 | ATACGCTGAATCCATAGGTGCCA (SEQ ID NO: 155) |
| FAM126A | TCTCTGCTGACCTGATTGATGCT (SEQ ID NO: 178) |
| PHC1 | ACCTCCTCACCTGTTGTAGCC (SEQ ID NO: 201) |
| ST8SIA4 | ACTGCTCTTGACCACTGACACA (SEQ ID NO: 236) |
| CHML | CCTCTGGCTGCTTATCATCACC (SEQ ID NO: 213) |
| CAV1 | TAGATAACAAGACCTCAGTGCCTTCC (SEQ ID NO: 248) |
| RPL23A | ACTGGCTCCTGATTACGATGCTT (SEQ ID NO: 260) |
| TPT1 | CATAACTGGCTTCTGCTTGTCATCC (SEQ ID NO: 261) |
| EEF1A1 | CCAGCAGCAACAATCAGGACAG (SEQ ID NO: 262) |
| SRSF3 | TTCCACTCTTACACGGCAGC (SEQ ID NO: 263) |
| TUT1 | CCTGTGGTCAAGTTCTGTCATCG (SEQ ID NO: 264) |
| HNRNPC | CTGCTGCTCTGCTCCTCTTCT (SEQ ID NO: 265) |
| HUWE1 | TCCTCTTCCTCCTCATCCTCACT (SEQ ID NO: 266) |
| WDR90 | TGGTCACTCAGCACACGGAA (SEQ ID NO: 267) |
| MATR3 | TGACCAGACAGAGCAGGAACC (SEQ ID NO: 268) |
| SMARCA4 | CCTTCCTCATCATCGTGCCTCT (SEQ ID NO: 269) |

TABLE 4

| Gene | Probe Sequence (5'-3') |
|---|---|
| THSD7A | TTTTTAAGACTTCTTGTCTCTCTCC (SEQ ID NO: 110) |
| | AACGAGTCCTCAAGTTCAGTATTTT (SEQ ID NO: 111) |
| | TACAATACGTTTCTACTTTCCCTGA (SEQ ID NO: 112) |
| | TGATTTTCAAACTGGTTGCCTGCAT (SEQ ID NO: 113) |
| | GGAAGGCACATTTTTGCACTATATT (SEQ ID NO: 114) |
| | AGTGCAGCACGATAGGCGCTTAACC (SEQ ID NO: 115) |
| | TAGGCGCTTAACCAGTATTGCCATA (SEQ ID NO: 116) |
| | GTATTGCCATAGAAAACTGCCTCTTT (SEQ ID NO: 117) |
| | AACTGCCTCTTTTCATGTGGGATGA (SEQ ID NO: 118) |
| | GACATTTGCAAGTTCTTGTATCCTG (SEQ ID NO: 119) |
| | GCTATTACACCTGCTGTACACACAC (SEQ ID NO: 120) |
| THSD7A | ACTTCTCTATTGACACTTTTACCTC (SEQ ID NO: 121) |
| | TGACACTTTTACCTCACCGAGGGGG (SEQ ID NO: 122) |
| | GAACTGCTGTTCCCTAGAATGAAGG (SEQ ID NO: 123) |
| | AGAATGAAGGTCTGTTGTTTGGTTT (SEQ ID NO: 124) |
| | TTATATGATTTTGCTGGACTATTTC (SEQ ID NO: 125) |
| | GGACTATTTCACTAGAAACCACGTA (SEQ ID NO: 126) |
| | GAATAGGACTAACTGATCTCTTTTG (SEQ ID NO: 127) |
| | AAAGGGGCTGATTTGCTTATTCATC (SEQ ID NO: 128) |
| | ATGTGGACAGTAATCTTAATTTCAA (SEQ ID NO: 129) |
| | GAGGATACTACGGTGTAGCTTAAGT (SEQ ID NO: 130) |
| | AGCACAAATTACTTCTAACAAGGCA (SEQ ID NO: 131) |
| THSD7A | GTATTTTCCCCTACGTAATGTACAT (SEQ ID NO: 132) |
| | GTACATGTCTTTAGGCCACAGTATT (SEQ ID NO: 133) |
| | AGGTGGCAGTGGTCATTGTAGCTTA (SEQ ID NO: 134) |
| | TAATCAGACCCCTGTTAAGTTCCTG (SEQ ID NO: 135) |
| | CAAGGTAAATTCACGTCTTCCTTCT (SEQ ID NO: 136) |
| | AATAGACCTCTCACACACTTATTTA (SEQ ID NO: 137) |
| | GTCTCTTTCTACTCTTGACAGCTAT (SEQ ID NO: 138) |
| | CTTGACAGCTATTCTTACCTACTTC (SEQ ID NO: 139) |
| | TTCCCACTAAACATGCCCAATTTTT (SEQ ID NO: 140) |
| | TCCTATATTTCCTTCCCTATTAGAA (SEQ ID NO: 141) |
| | GAATCAAAGTGTCACTCACTCAGAG (SEQ ID NO: 142) |
| MET | GTTGTCGACACCTACTATGATGATC (SEQ ID NO: 144) |
| | CAGCGTCAACAGAGGGACCTGCCAG (SEQ ID NO: 145) |
| | TTTCCCCACAATCATACTGCTGACA (SEQ ID NO: 146) |
| | AGATAGAAGAGCCCAGCCAGTGTCC (SEQ ID NO: 147) |
| | GGAGCCAAAGTCCTTTCATCTGTAA |

TABLE 4-continued

| Gene | Probe Sequence(5'-3') |
|---|---|
| | TAAAGGACCGGTTCATCAACTTCTT (SEQ ID NO: 148) |
| | ATTTCCCAGATCATCCATTGCATTC (SEQ ID NO: 149) |
| | ACGGACCAGTCCTACATTGATGTTT (SEQ ID NO: 150) |
| | GAGTTCAGAGATTCTTACCCCATTA (SEQ ID NO: 151) |
| | CTAGATGCTCAGACTTTTCACACAA (SEQ ID NO: 152) |
| | ATCAGGTTCTGTTCCATAAACTCTG (SEQ ID NO: 153) |
| RAB31 | AACATTGTAATGGCCATCGCTGGAA (SEQ ID NO: 156) |
| | GAAACAAGTGCGACCTCTCAGATAT (SEQ ID NO: 157) |
| | GGAGGTTCCCCTGAAGGATGCTAAG (SEQ ID NO: 158) |
| | TACGCTGAATCCATAGGTGCCATCG (SEQ ID NO: 159) |
| | GTGCCATCGTGGTTGAGACAAGTGC (SEQ ID NO: 160) |
| | TTCAAGGAATCAGCCGCCAGATCCC (SEQ ID NO: 161) |
| | TGAGAAGCCAACCATGCAAGCCAGC (SEQ ID NO: 162) |
| | CGTGGTCCACGGTACTTGAAGAAGC (SEQ ID NO: 163) |
| | ATCCTGTGCACTGCTGAAGGACCCT (SEQ ID NO: 164) |
| | GAGTGAGCACACTGGCTTTGCATCC (SEQ ID NO: 165) |
| | ACCACCACAAAATGGCCTTTAGTGT (SEQ ID NO: 166) |
| RAB31 | GAATATGACGTTACCTTGCAGACTA (SEQ ID NO: 167) |
| | TTTTTTGTGTGGGCTCCAGTTCTCA (SEQ ID NO: 168) |
| | GTTCTGCAATGCTCATGGCAAGTTG (SEQ ID NO: 169) |
| | ACCGACTGGGTATCTCTAGCTTACTGT (SEQ ID NO: 170) |
| | ATCATTGTTGAAACCAGACCCTGTA (SEQ ID NO: 171) |
| | AGACCCTGTAGTCCAGTGGTGCTGC (SEQ ID NO: 172) |
| | TAAAGAGCTTCCATCTGGGCTGGAC (SEQ ID NO: 173) |
| | TGGACCCAGTTCTTGCACATACAAG (SEQ ID NO: 174) |
| | GCACATACAAGACACCGCTGCAGTC (SEQ ID NO: 175) |
| | ACCGCTGCAGTCAGCTAGGACCTTT (SEQ ID NO: 176) |
| | GGTTTAACACACACTGATTCATACT (SEQ ID NO: 177) |
| FAM126A | GACTTACTTTAACAACCAGCCAATC (SEQ ID NO: 179) |
| | AATCCCTACCTAAGCCTAGTAGCCA (SEQ ID NO: 180) |
| | GCCATGGTTTGGCTAAGACCGCAGC (SEQ ID NO: 181) |
| | GTCAGTGGTGTCACAGTCCCACATA (SEQ ID NO: 182) |
| | ACATAACCCGTCATCTGCTGTTGGT (SEQ ID NO: 183) |
| | GCCAATAGGTTTTCCGCTTGTAGTC (SEQ ID NO: 184) |
| | GCAGAGACCTCCTAGTATTAGCATT (SEQ ID NO: 185) |
| | TTTTCTCCCATAACCTAGTGAACCT (SEQ ID NO: 186) |
| | GAAAGTACCCTGGGTCTTTCATCCG (SEQ ID NO: 187) |
| | CTTTCATCCGTATTCCTGACAGGAG (SEQ ID NO: 188) |
| | GGAGCCCTGATGTCTTAAATTCTGA (SEQ ID NO: 189) |
| FAM126A | CCGCGGCTCGGAGCAAGCGGTGCAG (SEQ ID NO: 190) |
| | GGAGCGATTCCCATTCGAGGAGTTT (SEQ ID NO: 191) |
| | TCTCATTTTAATACAACCCCGCCT (SEQ ID NO: 192) |
| | AACACCCGCCTCTTAGAGGCAGCAG (SEQ ID NO: 193) |
| | CAGACCAGTCCAGCCAGGTCAAGGT (SEQ ID NO: 194) |
| | TGTGGACCGCACAACGGGGTGCACA (SEQ ID NO: 195) |
| | TAAACGAGCCCTGGATCTGCAAAGC (SEQ ID NO: 196) |
| | GTGATCCCAACCTTAGCAACATAAT (SEQ ID NO: 197) |
| | TATATGTCAGGTGCCAGTGCTATGG (SEQ ID NO: 198) |
| | ATACCATTATTACCACTTCTCAGT (SEQ ID NO: 199) |
| | GAGGCTGTAACTCTGGTTGTCGAAA (SEQ ID NO: 200) |
| PHC1 | TTTCACGTACCTTAATCCAATCTTT (SEQ ID NO: 202) |
| | AGAACTAGGACTGCTCAGCCTTATC (SEQ ID NO: 203) |
| | GCCCAGGTCTTAATTCTCCAAGAGG (SEQ ID NO: 204) |
| | GGTGGAATGTCAGGTTGCCTGCCCA (SEQ ID NO: 205) |
| | AGGGTTTTCTAGCTTGTGTGACAG (SEQ ID NO: 206) |
| | TTGTCACTTACTCCCTTGTGATTGA (SEQ ID NO: 207) |
| | TGATTGAATTTTTTCTCCTGCATCC (SEQ ID NO: 208) |
| | AGAGACTTGGTTGGCATCTTCTGCT (SEQ ID NO: 209) |
| | GGCACATGTGGCTGTTGTCATTCTT (SEQ ID NO: 210) |
| | TGTTCCCCTCCAATTTATGTTATTT (SEQ ID NO: 211) |
| | GTACCTGCCTTAGGCACTATTCCTT (SEQ ID NO: 212) |
| CHML | GCAACTTTGACTTAGTTCATGCTAT (SEQ ID NO: 214) |
| | CTGTTTTAATTGCATGTGTCCTTAT (SEQ ID NO: 215) |
| | GTGTCCTTATAGCAGCAGCATTGTG (SEQ ID NO: 216) |
| | GCAGCATTGTGTATTAGTAGCCTTT (SEQ ID NO: 217) |
| | AGGGCTTTATAACTGATCTTTTGAC (SEQ ID NO: 218) |
| | GATCTTTTGACATACTCACTTTGAG (SEQ ID NO: 219) |
| | CACTTTGAGTGGCATATGCCCAGGA (SEQ ID NO: 220) |
| | AAGTTTTCTAGCAGTTCCACTCAGA (SEQ ID NO: 221) |
| | GTTCCACTCAGATAACTTTAAGGGG (SEQ ID NO: 222) |
| | TGGTGTATTGCTAGTGCTATCACAG (SEQ ID NO: 223) |
| | ATTGTGTTTACTGATACATGTGAAA (SEQ ID NO: 224) |
| FAM126A | TCTAGTCCTTTAATGAGCATGAATT (SEQ ID NO: 225) |
| | TATACTTCTACATTTGTTGCTTAGT (SEQ ID NO: 226) |

TABLE 4-continued

| Gene | Probe Sequence (5'-3') |
|---|---|
| | ATATTGTCTTCTATACTTTGTAACT (SEQ ID NO: 227) |
| | ATTTCACGTATTGTTGCTTTCTCTT (SEQ ID NO: 228) |
| | GTTGCTTTCTCTTATATGGAACTTA (SEQ ID NO: 229) |
| | GGAACTTATTGTGTACCTCTTACCT (SEQ ID NO: 230) |
| | GTATTCCTAGAGTTTACATTCCTAA (SEQ ID NO: 231) |
| | ACGACGACTTTGGCTATTTTTGTGT (SEQ ID NO: 232) |
| | GTTCCCTACCTTCTTAAGGCTATGG (SEQ ID NO: 233) |
| | ATTTGTGTAAATGTTCTCCATATGT (SEQ ID NO: 234) |
| | CAAGTGTTGCCTCTTGTTTTATTGA (SEQ ID NO: 235) |
| ST8SIA4 | TTTATTTTGCACGGCTCTAAACCTC (SEQ ID NO: 237) |
| | TAAACCTCCATGTTATTTTCCAGTG (SEQ ID NO: 238) |
| | GGTGTAGAAGGTACCAGCTAAAGTG (SEQ ID NO: 239) |
| | AGATGTTCCATGTCATCAGAGATGG (SEQ ID NO: 240) |
| | GGTACCAAAGATTACACTTGTGTTT (SEQ ID NO: 241) |
| | ACTTGTGTTTCTACACAGCAAACCA (SEQ ID NO: 242) |
| | GCTATTAATGTGAAAGTTGTCTCTA (SEQ ID NO: 243) |
| | ATGTTTTTCACACCTTTTGCATTAC (SEQ ID NO: 244) |
| | TTTTCACACCTTTTGCATTACATAA (SEQ ID NO: 245) |
| | AATTTTGTGGAAGCATTTTGCCCTT (SEQ ID NO: 246) |
| | GGAAGCATTTTGCCCTTTAGAATAA (SEQ ID NO: 247) |
| CAV1 | GAATTTCACCTGTAAACCTGAGTCG (SEQ ID NO: 249) |
| | CAGAAAGCTGCCTGGTATATCCAAA (SEQ ID NO: 250) |
| | TATTCCTCCTGCTCATATTGTGATT (SEQ ID NO: 251) |
| | GTCTTCCTGACACTTTAATTACCAA (SEQ ID NO: 252) |
| | TACCAACCTGTTACCTACTTTGACT (SEQ ID NO: 253) |
| | GTTACCTACTTTGACTTTTTGCATT (SEQ ID NO: 254) |
| | ATGTGCTATACTGCATACTTTTTAA (SEQ ID NO: 255) |
| | AACTGTGTATTCCAAGACATGTCTG (SEQ ID NO: 256) |
| | CATAGATGCTTAGTCCCTCATGCAA (SEQ ID NO: 257) |
| | AATTTTTTATCATGCATGTCCTGTA (SEQ ID NO: 258) |
| | TAAAGGTTACAAGCCTGCACAATAA (SEQ ID NO: 259) |

TABLE 5

| Gene | Sense Primer | Anti-sense Primer |
|---|---|---|
| THSD7A | GCCTGTTATGACTGGAAA (SEQ ID NO: 270) | CTGTCAACTTCTTCTCCA (SEQ ID NO: 271) |
| MET | CCTTGAACAGAATCACTG (SEQ ID NO: 272) | CCATGTTTCATGTATGGTA (SEQ ID NO: 273) |
| FAM126A | GCTTGTAGTCTCCAAGAA (SEQ ID NO: 274) | GGACAGAGTAATGCTAATAC (SEQ ID NO: 275) |
| PHC1 | GACAGCACATGTGGTAAA (SEQ ID NO: 276) | CACAGACTGCATATAGAAGG (SEQ ID NO: 277) |
| RAB31 | CTCAGATATTAGGGAGGTTC (SEQ ID NO: 278) | GCTGATTCCTTGAAAGAG (SEQ ID NO: 279) |
| ST8SIA4 | GCACAATGTAGAAGGTTG (SEQ ID NO: 280) | CAAGCACATAGTGTATGAC (SEQ ID NO: 281) |
| CHML | CTCCAAATCCAGAAGACA (SEQ ID NO: 282) | GGCCATTACTACATTATTGG (SEQ ID NO: 283) |
| CAV1 | CTGTGCCTGAATATTTGTTA (SEQ ID NO: 284) | CTGAGTTAGACCCTATTTGA (SEQ ID NO: 285) |
| RPL23A | GAGAGAAGAAGGCATATG (SEQ ID NO: 286) | TGGACTCAGTTTAGATGA (SEQ ID NO: 287) |
| TPT1 | GGCAATTATTTTGGATCTATC (SEQ ID NO: 288) | CAGTCCCATTTGTCTTAA (SEQ ID NO: 289) |
| EEF1A1 | CAGGACACAGAGACTTTA (SEQ ID NO: 290) | CAGCTTCAAATTCACCAA (SEQ ID NO: 291) |
| SRSF3 | CGAGAGCTAGATGGAAGA (SEQ ID NO: 292) | GGCCACGATTTCTACTTC (SEQ ID NO: 293) |
| TUT1 | GGTGTATCGAGTCCAAAC (SEQ ID NO: 294) | CAGGAAACGGGAGTTATG (SEQ ID NO: 295) |
| HNRNPC | CAAGCAGTAGAGATGAAG (SEQ ID NO: 296) | CTCCATCTTCACATTAGTC (SEQ ID NO: 297) |
| HUWE1 | CAAGGTCTAATCATGCTG (SEQ ID NO: 298) | CTGCTGGGTAGAATTAAAG (SEQ ID NO: 299) |
| WDR90 | CTCTGGAGACAAGGATGG (SEQ ID NO: 300) | GACACAGATGGTAGAGATTG (SEQ ID NO: 301) |
| MATR3 | GGTGAGAAAGACACAAAG (SEQ ID NO: 302) | CTGCTTCTTCTTCATCTAC (SEQ ID NO: 303) |
| SMARCA4 | GTACCTCATGGAGCACAA (SEQ ID NO: 304) | CCTTGTAAGACACCTTCAC (SEQ ID NO: 305) |

In one embodiment, the probe for detecting biomarker THSD7A may be at least one selected from the group consisting of SEQ ID NOS: 109 to 142, for example, at least one selected from the group consisting of a probe of SEQ ID NO: 109, a probe set comprising SEQ ID NOS: 110 to 120, a probe set comprising SEQ ID NOS: 121 to 131, and a probe set comprising SEQ ID NOS: 132 to 142. The primer for detecting biomarker THSD7A may be a primer of SEQ ID NO: 270, a primer of SEQ ID NO: 271, or a primer pair comprising the two primers, but not be limited thereto.

The probe for detecting biomarker MET may be at least one selected from the group consisting of SEQ ID NOS: 143 to 154, for example, a probe of SEQ ID NO: 143, a probe set comprising SEQ ID NOS: 144 to 154, or a combination thereof. The primer for detecting biomarker MET may be a primer of SEQ ID NO: 272, a primer of SEQ ID NO: 273, or a primer pair comprising the two primers, but not be limited thereto.

The probe for detecting biomarker RAB31 may be at least one selected from the group consisting of SEQ ID NOS: 155 to 177, for example, at least one selected from the group consisting of a probe of SEQ ID NO: 155, a probe set comprising SEQ ID NOS: 156 to 166, and a probe set comprising SEQ ID NOS: 167 to 177. The primer for detecting biomarker RAB31 may be a primer of SEQ ID NO: 278, a primer of SEQ ID NO: 279, or a primer pair comprising the two primers, but not be limited thereto.

The probe for detecting biomarker FAM126A may be at least one selected from the group consisting of SEQ ID NOS: 178 to 200 and 225 to 235, for example, at least one selected from the group consisting of a probe of SEQ ID NO: 178, a probe set comprising SEQ ID NOS: 179 to 189, a probe set comprising SEQ ID NOS: 190 to 200, and a probe set comprising SEQ ID NOS: 225 to 235. The primer for detecting biomarker FAM126A may be a primer of SEQ ID NO: 274, a primer of SEQ ID NO: 275, or a primer pair comprising the two primers, but not be limited thereto.

The probe for detecting biomarker PHC1 may be at least one selected from the group consisting of SEQ ID NOS: 201 to 212, for example, a probe of SEQ ID NO: 201, a probe set comprising SEQ ID NOS: 202 to 212, or a combination thereof. The primer for detecting biomarker PHC1 may be a primer of SEQ ID NO: 276, a primer of SEQ ID NO: 277, or a primer pair comprising the two primers, but not be limited thereto.

The probe for detecting biomarker CHML may be at least one selected from the group consisting of SEQ ID NOS: 213 to 224, for example, a probe of SEQ ID NO: 213, a probe set comprising SEQ ID NOS: 214 to 224, or a combination thereof. The primer for detecting biomarker CHML may be a primer of SEQ ID NO: 282, a primer of SEQ ID NO: 283, or a primer pair comprising the two primers, but not be limited thereto.

The probe for detecting biomarker ST8SIA4 may be at least one selected from the group consisting of SEQ ID NOS: 236 to 247, for example, a probe of SEQ ID NO: 236, a probe set comprising SEQ ID NOS: 237 to 247, or a combination thereof. The primer for detecting biomarker ST8SIA4 may be a primer of SEQ ID NO: 280, a primer of SEQ ID NO: 281, or a primer pair comprising the two primers, but not be limited thereto.

The probe for detecting biomarker CAV1 may be at least one selected from the group consisting of SEQ ID NOS: 248 to 259, for example, a probe of SEQ ID NO: 248, a probe set comprising SEQ ID NOS: 249 to 259, or a combination thereof. The primer for detecting biomarker CAV1 may be a primer of SEQ ID NO: 284, a primer of SEQ ID NO: 285, or a primer pair comprising the two primers, but not be limited thereto.

The probe for detecting reference marker EEF1A1 may a probe of SEQ ID NO: 262, but not be limited thereto. The primer for detecting reference marker EEF1A1 may be a primer of SEQ ID NO: 290, a primer of SEQ ID NO: 291, or a primer pair comprising the two primer, but not be limited thereto.

The probe for detecting reference marker RPL23A may a probe of SEQ ID NO: 260, but not be limited thereto. The primer for detecting reference marker RPL23A may be a primer of SEQ ID NO: 286, a primer of SEQ ID NO: 287, or a primer pair comprising the two primers, but not be limited thereto.

The probe for detecting reference marker TPT1 may a probe of SEQ ID NO: 261, but not be limited thereto. The primer for detecting reference marker TPT1 may be a primer of SEQ ID NO: 288 a primer of SEQ ID NO: 289, or a primer pair comprising the two primer, but not be limited thereto.

The probe for detecting reference marker HUWE1 may a probe of SEQ ID NO: 266, but not be limited thereto. The primer for detecting reference marker HUWE1 may be a primer of SEQ ID NO: 298 a primer of SEQ ID NO: 299, or a primer pair comprising the two primer, but not be limited thereto.

The probe for detecting reference marker MATR3 may a probe of SEQ ID NO: 268, but not be limited thereto. The primer for detecting reference marker MATR3 may be a primer of SEQ ID NO: 302 a primer of SEQ ID NO: 303, or a primer pair comprising the two primer, but not be limited thereto.

The probe for detecting reference marker SRSF3 may a probe of SEQ ID NO: 263, but not be limited thereto. The primer for detecting reference marker SRSF3 may be a primer of SEQ ID NO: 292 a primer of SEQ ID NO: 293, or a primer pair comprising the two primer, but not be limited thereto.

The probe for detecting reference marker HNRNPC may a probe of SEQ ID NO: 265, but not be limited thereto. The primer for detecting reference marker HNRNPC may be a primer of SEQ ID NO: 296 a primer of SEQ ID NO: 297, or a primer pair comprising the two primer, but not be limited thereto.

The probe for detecting reference marker SMARCA4 may a probe of SEQ ID NO: 269, but not be limited thereto. The primer for detecting reference marker SMARCA4 may be a primer of SEQ ID NO: 304 a primer of SEQ ID NO: 305, or a primer pair comprising the two primer, but not be limited thereto.

The probe for detecting reference marker WDR90 may a probe of SEQ ID NO: 267, but not be limited thereto. The primer for detecting reference marker WDR90 may be a primer of SEQ ID NO: 300 a primer of SEQ ID NO: 301, or a primer pair comprising the two primer, but not be limited thereto.

The probe for detecting reference marker TUT1 may a probe of SEQ ID NO: 264, but not be limited thereto. The primer for detecting reference marker TUT1 may be a primer of SEQ ID NO: 294 a primer of SEQ ID NO: 295, or a primer pair comprising the two primer, but not be limited thereto.

Another embodiment provides a method of predicting an effect of an anti-c-Met antibody on a subject (or a responsiveness or sensitivity of a subject to an anti-c-Met antibody) or selecting (or identifying) a subject for application of the anti-c-Met antibody (e.g., administration of or treatment with an anti-c-Met antibody), comprising determining (or measuring) the presence and/or the level of the biomarker (e.g., presence and/or amount of the biomarker) in a biological sample from a subject. In the method, the determination or measurement of presence and/or the level of the biomarker may be carried out using the reference marker as a reference for comparison.

For example, in the case of CAV1, FAM126A, MET, RAB31, ST8SIA4, and/or THSD7A, when the expression level of the gene(s) is high, it can be determined (or predicted) that an anti-c-Met antibody can exhibit an effect (i.e., the treatment using an anti-c-Met antibody is effective) or the biological sample or the subject from which the biological sample is obtained (isolated or separated) is suitable for application of the anti-c-Met antibody. In addition, in the case of CMHL and/or PHC1, when the expression level is low, it can be determined (or predicted) that an anti-c-Met antibody can exhibit an effect (i.e., the treatment using an anti-c-Met antibody is effective) or the biological sample or the subject from which the biological sample is obtained (isolated or separated) is suitable for application of the anti-c-Met antibody.

The method may further comprise administering an anti-c-Met antibody to a subject who is determined as being sensitive or suitable for application of the anti-c-Met antibody.

The expression level of the biomarker may be evaluated by comparing it to that of the reference marker. For example, the evaluation of the expression of the biomarker and the determination (or prediction) of the effect and/or applicability of an anti-c-Met antibody may be performed using a polymerase chain reaction (PCR; e.g., competitive PCR, real-time PCR (RT-PCR), etc.), referring to Table 6.

TABLE 6

| Gene (biomarker) | Reference standard value | Determination |
|---|---|---|
| CAV1, FAM126A, MET, RAB31, ST8SIA4, THSD7A | An average value between minimum ΔCt of efficacy group and maximum ΔCt of non-efficacy group: [Min(efficacy value (ΔCt)) + Max(non-efficacy value (ΔCt))]/2 | When Ct value of a biomarker in a biological sample is higher than the standard value, it is determined that the expression level of the biomarker is "high" → the biological sample or a subject from which the biological sample is obtained from is determined to be responsive to an anti-c-Met antibody or suitable for application of an anti-c-Met antibody |
| CMHL, PHC1 | An average value between minimum ΔCt of efficacy group and maximum ΔCt of non-efficacy group: [Min(non-efficacy value (ΔCt)) + Max(efficacy value (ΔCt))]/2 | When Ct value of a biomarker in a biological sample is lower than the standard value, it is determined that the expression level of the biomarker is "low" → the biological sample or a subject from which the biological sample is obtained from is determined to be responsive to an anti-c-Met antibody or suitable for application of an anti-c-Met antibody |

(ΔCt = Ct (threshold cycle) value of reference marker (if two or more reference markers are used, this term means "an average value of Ct values of reference markers") − Ct value of a biomarker)

In the Table 6, the reference marker may be at least one selected from the group consisting of EEF1A1, RPL23A, TPT1, HUWE1, MATR3, SRSF3, HNRNPC, SMARCA4, WDR90, and TUT1, as described above.

The methods described herein may further comprise determining, for each biomarker, a reference standard expression value, as set forth in Table 6, against which the biomarkers may be compared. The reference standard expression value can be determined, for example, by (i) determining ΔCt for each biomarker in (a) a population of subjects known to be anti-c-Met antibody sensitive (also called as "efficacy group") and (b) a population of subjects known to be anti-c-Met antibody insensitive (e.g., resistant) (also called as "non-efficacy group"); and (ii) averaging the ΔCt from (a) and (b) to provide a standard expression value. As explained above, ΔCt is the average Ct value of one or more reference markers (EEF1A1, RPL23A, TPT1, HUWE1, MATR3, SRSF3, HNRNPC, SMARCA4, WDR90, and TUT1)−Ct value of a given biomarker for which the standard expression value is calculated. The efficacy group and non-efficacy group may be determined by a preceding in vivo test (e.g., clinical test) or ex vivo test (e.g., cell test) for confirming an efficacy (e.g., an anticancer efficacy such as inhibition of cancer cell proliferation, etc.) of an anti-c-Met antibody.

Alternatively, the "low or high expression level" may be determined by comparing the expression level of a biomarker in a biological sample from a subject with that in a reference sample. The reference sample may be any cell or tissue on which an anti-c-Met antibody has no effect or having a resistance to an anti-c-Met antibody (e.g., c-Met antibody non-efficacy group, such as c-Met antibody insensitive group or c-Met antibody resistant group). For example, the reference sample may be at least one selected from the group consisting of cell lines H1373 (ATCC, CRL-5866), HCC1806 (ATCC, CRL-2335), Caki-1 (ATCC, HTB-46), SKBR3 (ATCC, HTB-30), BT474 (ATCC, HTB-20), HT-29 (ATCC, HTB-38), LoVo (ATCC, CCL-229), HCT116 (ATCC, CCL-247), SW620 (ATCC, CCL-227), Ls174T (ATCC, CL-188), and cells acquiring a resistance to an anti-c-Met antibody by repeated and/or consistent administration of the anti-c-Met antibody. Therefore, the method of predicting an effect of an anti-c-Met antibody on a subject or selecting (or identifying) a subject for application of the anti-c-Met antibody may further comprise a step of comparing the expression level of a biomarker in a biological sample with that of a reference sample as described above. In this case, the method may further comprise a step of measuring the expression level of a biomarker in the reference sample. The method may further comprise a step of determining (predicting or selecting) that the anti-c-Met antibody has an effect on the biological sample or the subject from which the biological sample is obtained (separated) or the biological sample or the subject from which the biological sample is obtained (separated) is suitable for application of an anti-c-Met antibody, when the expression level of the biomarker (at least one selected from the group consisting of CAV1, FAM126A, MET, RAB31, ST8SIA4, and THSD7A) is higher than that of the reference sample or when the expression level of the biomarker (CMHL, PHC1, or a combination thereof) is lower than that of the reference sample.

Measuring a level of the biomarker or reference marker may comprise i) treating (reacting or contacting) a biological sample with a molecule or composition for detecting the biomarker or reference marker; and ii) quantitatively analyzing the reaction mixture to determine the level of the biomarker or reference marker. In an embodiment, prior to step i), a step of providing a biological sample may be further performed, wherein the preparation step may comprise obtaining (isolating) a biological sample from a patient or obtaining a biological sample which has been isolated from a patient. In step i), the molecule or composition for detecting the biomarker or reference marker may be as described above. In an embodiment, the molecule or composition for detecting the biomarker or reference marker may be conjugated with a general label, such as a fluorescent, a secondary antibody, a bead (e.g., a magnetic bead or polystyrene bead), a dye, or any combination thereof. The step i) may be configured to form a complex by adding the molecule or composition for detecting the biomarker or reference marker may be to the biological sample. In step ii), the reaction mixture may be the complex resulting from interaction (binding) between the biomarker or reference marker and the molecule or composition for detecting the biomarker or reference marker, which can be obtained in step i). Quantitatively analyzing may comprise quantifying the complex, the label conjugated to the complex, or the biomarker or reference marker segregated from the complex after the isolation of the complex from the biological sample.

The subject may refer to any patient suitable for the application of a therapy with an anti-c-Met antibody. The subject may be any mammal, for example, a primate such as human or a monkey, a rodent a rat or a mouse, and the like. For example, the subject may be a patient suffering from cancer. The biological sample may be at least one selected from a cell, a tissue, body fluid (e.g., blood, serum, blood plasma, etc.), and the like, which is separated from a subject (e.g., any mammal, for example, a primate such as human or a monkey, a rodent a rat or a mouse, and the like), or artificially cultured. For example, the biological sample may be a cancer cell or a cancer tissue, or DNA or RNA extracted from the cell or tissue, or a protein isolated from the cell or tissue. The biological sample may be a non-processed sample or a processed sample (e.g., RRPE (formalin fixed paraffin embedded) sample).

In an embodiment, the subject may be a cancer patient. The cancer may be associated with over-expression and/or abnormal activation of c-Met. The cancer may be a solid cancer or a blood cancer. The cancer may be a primary cancer or a metastatic cancer. For example, the cancer may be, but not limited to, one or more selected from the group consisting of squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastric cancer, gastrointestinal cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, head or neck cancer, brain cancer, osteosarcoma, and the like. In one embodiment, the subject may be a patient suffering from lung cancer (e.g., lung cancer adenocarcinoma, non-small cell adenocarcinoma, etc.).

The measurement of the presence and/or expression level of a biomarker and/or a reference marker may be carried out by any general gene assay using a primer, a probe, or an aptamer, which is capable of hybridizing with the gene, for example, by polymerase chain reaction (PCR; e.g., q PCR or RT-PCR), fluorescent in situ hybridization (FISH), or microarray assay, but not be limited thereto. In one embodiment, the presence and/or expression level of a biomarker and/or a reference marker may be measured by a general gene quantification assay, for example by PCR. Alternatively, the presence of a biomarker may be identified by a general sequencing. In one embodiment, the primer may be designed to detect an entire gene or a fragment of contiguous nucleotides within a biomarker or reference marker gene (full-length DNA, cDNA or mRNA), for example, a fragment of about 5 to about 100 bp, e.g., about 10 to about 500 bp, about 20 to about 200 bp, or about 50 to about 200 bp. The primer may be a pair of primers comprising or consisting essentially of nucleotide sequences which are respectively capable of hybridizing with (e.g., complementary to) 3'- and 5'-terminal regions ranging in size from about 5 to about 100 bp, e.g., about 5 to about 50 bp, about 5 to about 30 bp, or about 10 to 25 bp. The probe or the aptamer capable of hybridizing with the gene may comprise or consist essentially of a nucleotide sequence with a size of from about 5 to about 100 bp, from about 5 to about 50 bp, from about 5 to about 30 bp, or from about 5 to about 25 bp, which is capable of hybridizing with (or complementary to) a fragment (about 5 to about 100 bp, about 5 to about 50 bp, about 5 to about 30 bp, or about 5 to about 25 bp) of the biomarker or reference marker gene (full-length DNA, cDNA or mRNA). As used herein, the term "capable of hybridizing" may refer to complementarily binding to a specific region of the gene, with a sequence complementarity of 80% or higher, e.g., 90% or higher, 95% or higher, 98% or higher, 99% or higher, or 100% between the primer, probe or aptamer and the gene region.

The presence and/or expression level of a biomarker and/or a reference marker can be measured by quantifying a protein encoded thereby. The protein quantification may be performed by detecting enzymatic reactions, fluorescence, luminescence, and/or radioactivity using a chemical, an antibody, and/or an aptamer, which specifically bind to the protein. For example, the protein quantification may be carried out using an analysis technique selected from the group consisting of, but not limited to, immunochromatography, immunohistochemical staining, enzyme linked immunosorbent assay (ELISA), radioimmunoassay (RIA), enzyme immunoassay (EIA), fluorescence immunoassay (FIA), luminescence immunoassay (LIA), Western blotting, microarray, flow cytometry, immunohistochemistry (IHC), surface plasmon resonance (SPR), and the like.

Another embodiment provides a method of inhibiting c-Met or preventing and/or treating cancer, comprising administering an anti-c-Met antibody to a subject who has a high level of CAV1, FAM126A, MET, RAB31, ST8SIA4, and/or THSD7A, and/or a low level of CMHL and/or PHC1, wherein the term "high level" and "low level" can be determined as described above. In an embodiment, the subject may be one selected as above.

The method of inhibiting c-Met or preventing and/or treating cancer may further comprise a step of identifying a subject for application of an anti-c-Met antibody, prior to the step of administration. The step of identifying may be a step of identifying a biological sample or subject which is selected by the method of a subject for application of an anti-c-Met antibody, and may be carried out by performing the steps described in the selecting method or by confirming that a subject or biological sample of interest is selected by the selecting method.

In one embodiment, the method of inhibiting c-Met or preventing and/or treating cancer may comprise:

identifying a subject for application of an anti-c-Met antibody; and administering an anti-c-Met antibody to the subject who is identified (or selected) as being suitable for application of an anti-c-Met antibody.

Alternatively, the method of inhibiting c-Met or preventing and/or treating cancer may comprise:

selecting a subject for application of an anti-c-Met antibody by measuring the presence and/or level of a biomarker; and administering an anti-c-Met antibody to the selected subject.

In the above methods, the anti-c-Met antibody may be administered in an effective amount for inhibiting c-Met or preventing and/or treating cancer.

In an embodiment, the anti-c-Met antibody may be any antibody and/or antigen-binding fragment thereof, which recognizes c-Met protein as an antigen. For example, the anti-c-Met antibody may recognize a specific region of c-Met, e.g., a specific region in the SEMA domain, as an epitope. It may be any antibody or antigen-binding fragment that acts on c-Met to induce c-Met intracellular internalization and degradation.

As used herein, unless otherwise stated, the term "anti-c-Met antibody" may be used to include not only a complete form of antibody but also an antigen-binding fragment thereof.

The term "c-Met" or "c-Met protein" refers to a receptor tyrosine kinase (RTK) which binds hepatocyte growth factor (HGF). c-Met may be a c-Met protein from any species, particularly a mammal, for instance, primates such as human c-Met (e.g., NP_000236) or monkey c-Met (e.g., *Macaca mulatta*, NP_001162100), or rodents such as mouse c-Met (e.g., NP_032617.2) or rat c-Met (e.g., NP_113705.1). The c-Met protein may include a polypeptide encoded by the nucleotide sequence identified as GenBank Accession Number NM_000245, a polypeptide having the amino acid sequence identified as GenBank Accession Number NP_000236 or extracellular domains thereof. The receptor tyrosine kinase c-Met participates in various mechanisms, such as cancer development, metastasis, migration of cancer cell, invasion of cancer cell, and angiogenesis.

c-Met, a receptor for hepatocyte growth factor (HGF), may be divided into three portions: extracellular, transmembrane, and intracellular. The extracellular portion is composed of an α (alpha)-subunit and a β (beta)-subunit which are linked to each other through a disulfide bond, and contains a SEMA domain responsible for binding HGF, a PSI domain (plexin-semaphorins-integrin homology domain) and an IPT domain (immunoglobulin-like fold shared by plexins and transcriptional factors domain). The SEMA domain of c-Met protein may have the amino acid sequence of SEQ ID NO: 79, and is an extracellular domain that functions to bind HGF. A specific region of the SEMA domain, that is, a region having the amino acid sequence of SEQ ID NO: 71, which corresponds to a range from amino acid residues 106 to 124 of the amino acid sequence of the SEMA domain (SEQ ID NO: 79) of c-Met protein, is a loop region between the second and the third propellers within the epitopes of the SEMA domain. The region acts as an epitope for the specific anti-c-Met antibody of the present disclosure.

The term "epitope" as used herein, refers to an antigenic determinant, a part of an antigen recognized by an antibody. In one embodiment, the epitope may be a region comprising 5 or more contiguous amino acid residues within the SEMA domain (SEQ ID NO: 79) of c-Met protein, for instance, 5 to 19 contiguous amino acid residues within the amino acid sequence of SEQ ID NO: 71. Contiguous amino acids may be consecutive amino acids in the linear sequence, or contiguous in a three-dimensional configuration of the epitope without necessarily being consecutive in the linear sequence. For example, the epitope may be a polypeptide having 5 to 19 contiguous (or consecutive) amino acids selected from among partial combinations of the amino acid sequence of SEQ ID NO: 71, wherein the polypeptide essentially includes the amino sequence of SEQ ID NO: 73 (EEPSQ) serving as an essential element for the epitope. For example, the epitope may be a polypeptide comprising, consisting essentially of, or consisting of the amino acid sequence of SEQ ID NO: 71, SEQ ID NO: 72, or SEQ ID NO: 73.

The epitope having the amino acid sequence of SEQ ID NO: 72 corresponds to the outermost part of the loop between the second and third propellers within the SEMA domain of a c-Met protein. The epitope having the amino acid sequence of SEQ ID NO: 73 is a site to which the antibody or antigen-binding fragment according to one embodiment most specifically binds.

Thus, the anti-c-Met antibody may specifically bind to an epitope which has 5 to 19 contiguous (or consecutive) amino acids selected from the amino acid sequence of SEQ ID NO: 71, including SEQ ID NO: 73 (EEPSQ), as an essential element. For example, the anti-c-Met antibody may specifically bind to an epitope including the amino acid sequence of SEQ ID NO: 71, SEQ ID NO: 72, or SEQ ID NO: 73.

In one embodiment, the anti-c-Met antibody or an antigen-binding fragment thereof may include:

at least one heavy chain complementarity determining region (CDR) selected from the group consisting of (a) a CDR-H1 comprising the amino acid sequence of SEQ ID NO: 4; (b) a CDR-H2 comprising the amino acid sequence of SEQ ID NO: 5, SEQ ID NO: 2, or an amino acid sequence comprising 8-19 consecutive amino acids within SEQ ID NO: 2 including amino acid residues from the $3^{rd}$ to $10^{th}$ positions of SEQ ID NO: 2; and (c) a CDR-H3 comprising the amino acid sequence of SEQ ID NO: 6, SEQ ID NO: 85, or an amino acid sequence comprising 6-13 consecutive amino acids within SEQ ID NO: 85 including amino acid residues from the $1^{st}$ to $6^{th}$ positions of SEQ ID NO: 85, or a heavy chain variable region including the at least one heavy chain complementarity determining region;

at least one light chain complementarity determining region (CDR) selected from the group consisting of (a) a CDR-L1 comprising the amino acid sequence of SEQ ID NO: 7, (b) a CDR-L2 comprising the amino acid sequence of SEQ ID NO: 8, and (c) a CDR-L3 comprising the amino acid sequence of SEQ ID NO: 9, SEQ ID NO: 15, SEQ ID NO: 86, or an amino acid sequence comprising 9-17 consecutive amino acids within SEQ ID NO: 89 including amino acid residues from the $1^{st}$ to $9^{th}$ positions of SEQ ID NO: 89, or a light chain variable region including the at least one light chain complementarity determining region;

a combination of the at least one heavy chain complementarity determining region and at least one light chain complementarity determining region; or a combination of the heavy chain variable region and the light chain variable region.

Herein, the amino acid sequences of SEQ ID NOS: 4 to 9 are respectively represented by following Formulas I to VI, below:

Formula I
(SEQ ID NO: 4)
$Xaa_1$-$Xaa_2$-Tyr-Tyr-Met-Ser, wherein $Xaa_1$ is absent or Pro or Ser, and $Xaa_2$ is Glu or Asp, Formula II
(SEQ ID NO: 5)
Arg-Asn-$Xaa_3$-$Xaa_4$-Asn-Gly-$Xaa_5$-Thr, wherein $Xaa_3$ is Asn or Lys, $Xaa_4$ is Ala or Val, and $Xaa_5$ is Asn or Thr, Formula III
(SEQ ID NO: 6)
Asp-Asn-Trp-Leu-$Xaa_6$-Tyr, wherein $Xaa_6$ is Ser or Thr, Formula IV
(SEQ ID NO: 7)
Lys-Ser-Ser-$Xaa_7$-Ser-Leu-Leu-Ala-$Xaa_8$-Gly-Asn-$Xaa_9$-$Xaa_{10}$-Asn-Tyr-Leu-Ala wherein $Xaa_7$ is His, Arg, Gln, or Lys, $Xaa_8$ is Ser or Trp, $Xaa_9$ is His or Gln, and $Xaa_{10}$ is Lys or Asn, Formula V
(SEQ ID NO: 8)
Trp-Xaa$_{11}$-Ser-Xaa$_{12}$-Arg-Val-Xaa$_{13}$ wherein Xaa$_{11}$ is Ala or Gly, Xaa$_{12}$ is Thr or Lys, and Xaa$_{13}$ is Ser or Pro, and Formula VI
(SEQ ID NO: 9)
Xaa$_{14}$-Gln-Ser-Tyr-Ser-Xaa$_{15}$-Pro-Xaa$_{16}$-Thr wherein Xaa$_{14}$ is Gly, Ala, or Gln, Xaa$_{15}$ is Arg, His, Ser, Ala, Gly, or Lys, and Xaa$_{16}$ is Leu, Tyr, Phe, or Met.

In one embodiment, the CDR-H1 may include an amino acid sequence selected from the group consisting of SEQ ID NOS: 1, 22, 23, and 24. The CDR-H2 may include an amino acid sequence selected from the group consisting of SEQ ID NOS: 2, 25, and 26. The CDR-H3 may include an amino acid sequence selected from the group consisting of SEQ ID NOS: 3, 27, 28, and 85.

The CDR-L1 may include an amino acid sequence selected from the group consisting of SEQ ID NOS: 10, 29, 30, 31, 32, 33, and 106. The CDR-L2 may include an amino acid sequence selected from the group consisting of SEQ ID NOS: 11, 34, 35, and 36. The CDR-L3 may include an amino acid sequence selected from the group consisting of SEQ ID NOS: 12, 13, 14, 15, 16, 37, 86, and 89.

In another embodiment, the antibody or antigen-binding fragment may comprise a heavy chain variable region comprising a polypeptide (CDR-H1) comprising an amino acid sequence selected from the group consisting of SEQ ID NOS: 1, 22, 23, and 24, a polypeptide (CDR-H2) comprising an amino acid sequence selected from the group consisting of SEQ ID NOS: 2, 25, and 26, and a polypeptide (CDR-H3) comprising an amino acid sequence selected from the group consisting of SEQ ID NOS: 3, 27, 28, and 85; and a light chain variable region comprising a polypeptide (CDR-L1) comprising an amino acid sequence selected from the group consisting of SEQ ID NOS: 10, 29, 30, 31, 32, 33 and 106, a polypeptide (CDR-L2) comprising an amino acid sequence selected from the group consisting of SEQ ID NOS: 11, 34, 35, and 36, and a polypeptide (CDR-L3) comprising an amino acid sequence selected from the group consisting of SEQ ID NOS 12, 13, 14, 15, 16, 37, 86, and 89.

In one embodiment of the anti-c-Met antibody or antigen-binding fragment, the variable region of the heavy chain includes the amino acid sequence of SEQ ID NO: 17, 74, 87, 90, 91, 92, 93, or 94 and the variable region of the light chain includes the amino acid sequence of SEQ ID NO: 306, 18, 19, 20, 21, 75, 88, 95, 96, 97, 98, 99, or 107.

Animal-derived antibodies produced by immunizing non-immune animals with a desired antigen generally invoke immunogenicity when injected to humans for the purpose of medical treatment, and thus chimeric antibodies have been developed to inhibit such immunogenicity. Chimeric antibodies are prepared by replacing constant regions of animal-derived antibodies that cause an anti-isotype response with constant regions of human antibodies by genetic engineering. Chimeric antibodies are considerably improved in terms of anti-isotype response compared to animal-derived antibodies, but variable regions still have animal-derived amino acid sequences, so that chimeric antibodies have side effects with respect to a potential anti-idiotype response. Humanized antibodies have been developed to reduce such side effects. Humanized antibodies are produced by grafting complementarity determining regions (CDR) which serve an important role in antigen binding in variable regions of chimeric antibodies into a human antibody framework.

In using CDR grafting to produce humanized antibodies, choosing which optimized human antibodies to use for accepting CDRs of animal-derived antibodies is critical. Antibody databases, analysis of a crystal structure, and technology for molecule modeling are used. However, even when the CDRs of animal-derived antibodies are grafted to the most optimized human antibody framework, amino acids positioned in a framework of the animal-derived CDRs affecting antigen binding are present. Therefore, in many cases, antigen binding affinity is not maintained, and thus application of additional antibody engineering technology for recovering the antigen binding affinity is necessary.

The anti c-Met antibodies may be, but are not limited to, mouse-derived antibodies, mouse-human chimeric antibodies, humanized antibodies, or human antibodies. The antibodies or antigen-binding fragments thereof may be isolated from a living body or non-naturally occurring. The antibodies or antigen-binding fragments thereof may be synthetic or recombinant.

An intact antibody includes two full-length light chains and two full-length heavy chains, in which each light chain is linked to a heavy chain by disulfide bonds. The antibody has a heavy chain constant region and a light chain constant region. The heavy chain constant region is of a gamma (γ), mu (μ), alpha (α), delta (δ), or epsilon (ε) type, which may be further categorized as gamma 1 (γ1), gamma 2 (γ2), gamma 3 (γ3), gamma 4 (γ4), alpha 1 (α1), or alpha 2 (α2). The light chain constant region is of either a kappa (κ) or lambda (λ) type.

As used herein, the term "heavy chain" refers to full-length heavy chain, and fragments thereof, including a variable region $V_H$ that includes amino acid sequences sufficient to provide specificity to antigens, and three constant regions, $C_{H1}$, $C_{H2}$, and $C_{H3}$, and a hinge. The term "light chain" refers to a full-length light chain and fragments thereof, including a variable region $V_L$ that includes amino acid sequences sufficient to provide specificity to antigens, and a constant region $C_L$.

The term "complementarity determining region (CDR)" refers to an amino acid sequence found in a hyper variable region of a heavy chain or a light chain of immunoglobulin. The heavy and light chains may respectively include three CDRs (CDRH1, CDRH2, and CDRH3; and CDRL1, CDRL2, and CDRL3). The CDR may provide contact residues that play an important role in the binding of antibodies to antigens or epitopes. The terms "specifically binding" and "specifically recognized" are well known to one of ordinary skill in the art, and indicate that an antibody and an antigen specifically interact with each other to lead to an immunological activity.

The term "antigen-binding fragment" used herein refers to fragments of an intact immunoglobulin including portions of a polypeptide including antigen-binding regions having the ability to specifically bind to the antigen. In a particular embodiment, the antigen-binding fragment may be scFv, (scFv)$_2$, scFvFc, Fab, Fab', or F(ab')$_2$, but is not limited thereto.

Among the antigen-binding fragments, Fab that includes light chain and heavy chain variable regions, a light chain constant region, and a first heavy chain constant region $C_{H1}$, has one antigen-binding site.

The Fab' fragment is different from the Fab fragment, in that Fab' includes a hinge region with at least one cysteine residue at the C-terminal of $C_{H1}$.

The F(ab')₂ antibody is formed through disulfide bridging of the cysteine residues in the hinge region of the Fab' fragment.

Fv is the smallest antibody fragment with only a heavy chain variable region and a light chain variable region. Recombination techniques of generating the Fv fragment are widely known in the art.

Two-chain Fv includes a heavy chain variable region and a light chain variable region which are linked by a non-covalent bond. Single-chain Fv generally includes a heavy chain variable region and a light chain variable region which are linked by a covalent bond via a peptide linker or linked at the C-terminals to have a dimer structure like the two-chain Fv. The peptide linker may be the same as described above, including, but not limited to, those having an amino acid length of 1 to 100, 2 to 50, particularly 5 to 25, and any kinds of amino acids may be included without any restrictions.

The antigen-binding fragments may be obtained using protease (for example, the Fab fragment may be obtained by restricted cleavage of a whole antibody with papain, and the F(ab')₂ fragment may be obtained by cleavage with pepsin), or may be prepared by using a genetic recombination technique.

The term "hinge region," as used herein, refers to a region between CH1 and CH2 domains within the heavy chain of an antibody which functions to provide flexibility for the antigen-binding site.

When an animal antibody undergoes a chimerization process, the IgG1 hinge of animal origin is replaced with a human IgG1 hinge or IgG2 hinge while the disulfide bridges between two heavy chains are reduced from three to two in number. In addition, an animal-derived IgG1 hinge is shorter than a human IgG1 hinge. Accordingly, the rigidity of the hinge is changed. Thus, a modification of the hinge region may bring about an improvement in the antigen binding efficiency of the humanized antibody. The modification of the hinge region through amino acid deletion, addition, or substitution is well-known to those skilled in the art.

In one embodiment, the anti-c-Met antibody or an antigen-binding fragment thereof may be modified by any combination of deletion, insertion, addition, or substitution of at least one amino acid residue on the amino acid sequence of the hinge region so that it exhibit enhanced antigen-binding efficiency. For example, the antibody may include a hinge region including the amino acid sequence of SEQ ID NO: 100 (U7-HC6), 101 (U6-HC7), 102 (U3-HC9), 103 (U6-HC8), or 104 (U8-HC5), or a hinge region including the amino acid sequence of SEQ ID NO: 105 (non-modified human hinge). In particular, the hinge region has the amino acid sequence of SEQ ID NO: 100 or 101.

In one embodiment, the anti-c-Met antibody may be a monoclonal antibody. The monoclonal antibody may be produced by the hybridoma cell line deposited with Accession No. KCLRF-BP-00220, which binds specifically to the extracellular region of c-Met protein (refer to Korean Patent Publication No. 2011-0047698, the disclosure of which is incorporated in its entirety herein by reference). The anti-c-Met antibody may include all the antibodies defined in Korean Patent Publication No. 2011-0047698.

In the anti-c-Met antibody, the rest portion of the light chain and the heavy chain portion except the CDRs or the light chain variable region and the heavy chain variable region as defined above, for example, the light chain constant region and the heavy chain constant region, may be those from any subtype of immunoglobulin (e.g., IgA, IgD, IgE, IgG (IgG1, IgG2, IgG3, IgG4), IgM, and the like).

By way of further example, the anti-c-Met antibody or the antibody fragment may include:

a heavy chain including the amino acid sequence selected from the group consisting of the amino acid sequence of SEQ ID NO: 62 (wherein the amino acid sequence from amino acid residues from the $1^{st}$ to $17^{th}$ positions is a signal peptide), or the amino acid sequence from the $18^{th}$ to $462^{nd}$ positions of SEQ ID NO: 62, the amino acid sequence of SEQ ID NO: 64 (wherein the amino acid sequence from the $1^{st}$ to $17^{th}$ positions is a signal peptide), the amino acid sequence from the $18^{th}$ to $461^{st}$ positions of SEQ ID NO: 64, the amino acid sequence of SEQ ID NO: 66 (wherein the amino acid sequence from the $1^{st}$ to $17^{th}$ positions is a signal peptide), and the amino acid sequence from the $18^{th}$ to $460^{th}$ positions of SEQ ID NO: 66; and a light chain including the amino acid sequence selected from the group consisting of the amino acid sequence of SEQ ID NO: 68 (wherein the amino acid sequence from the $1^{st}$ to $20^{th}$ positions is a signal peptide), the amino acid sequence from the $21^{st}$ to $240^{th}$ positions of SEQ ID NO: 68, the amino acid sequence of SEQ ID NO: 70 (wherein the amino acid sequence from the $1^{st}$ to $20^{th}$ positions is a signal peptide), the amino acid sequence from the $21^{st}$ to $240^{th}$ positions of SEQ ID NO: 70, and the amino acid sequence of SEQ ID NO: 108.

For example, the anti-c-Met antibody may be selected from the group consisting of:

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 62 or the amino acid sequence from the 18$^{th}$ to 462$^{nd}$ positions of SEQ ID NO: 62 and a light chain including the amino acid sequence of SEQ ID NO: 108;

an antibody including a heavy chain including the amino acid sequence of SEQ ID NO: 64 or the amino acid sequence from the 18$^{th}$ to 461$^{st}$ positions of SEQ ID NO: 64 and a light chain including the amino acid sequence of SEQ ID NO: 108; and an antibody including a heavy chain including the amino acid sequence of SEQ ID NO: 66 or the amino acid sequence from the 18$^{th}$ to 460$^{th}$ positions of SEQ ID NO: 66 and a light chain including the amino acid sequence of SEQ ID NO: 108.

According to an embodiment, the anti-c-Met antibody may include a heavy chain including the amino acid sequence from the 18$^{th}$ to 460$^{th}$ positions of SEQ ID NO: 66 and a light chain including the sequence from the 21$^{st}$ to 240$^{th}$ positions of SEQ ID NO: 68, or a heavy chain including the amino acid sequence from the 18$^{th}$ to 460$^{th}$ positions of SEQ ID NO: 66 and a light chain including the sequence of SEQ ID NO: 108.

The polypeptide of SEQ ID NO: 70 is a light chain including human kappa (κ) constant region, and the polypeptide with the amino acid sequence of SEQ ID NO: 68 is a polypeptide obtained by replacing histidine at position 62 (corresponding to position 36 of SEQ ID NO: 68 according to kabat numbering) of the polypeptide with the amino acid sequence of SEQ ID NO: 70 with tyrosine. The production yield of the antibodies may be increased by the replacement. The polypeptide with the amino acid sequence of SEQ ID NO: 108 is a polypeptide obtained by replacing serine at position 32 (position 27e according to kabat numbering in the amino acid sequence from amino acid residues 21 to 240 of SEQ ID NO: 68; positioned within CDR-L1) with tryptophan. By such replacement, antibodies and antibody fragments including such sequences exhibits increased activities, such as c-Met biding affinity, c-Met degradation activity, and Akt phosphorylation inhibition.

The anti-c-Met antibody may be formulated with a pharmaceutically acceptable carrier. The pharmaceutically acceptable carrier to be included in the mixture or the pharmaceutical composition may be those commonly used for the formulation of antibodies, which may be one or more selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but are not limited thereto. The anti-c-Met antibody may further include one or more selected from the group consisting of a lubricant, a wetting agent, a sweetener, a flavor enhancer, an emulsifying agent, a suspension agent, and preservative.

The anti-c-Met antibody may be administered orally or parenterally. The parenteral administration may include intravenous injection, subcutaneous injection, muscular injection, intraperitoneal injection, endothelial administration, local administration, intranasal administration, intrapulmonary administration, and rectal administration. Since oral administration leads to digestion of proteins or peptides, an active ingredient in the compositions for oral administration must be coated or formulated to prevent digestion in the stomach. In addition, the compositions may be administered using an optional device that enables an active substance to be delivered to target cells.

The anti-c-Met antibody may be used for the prevention and/or treatment of a cancer. The cancer may be associated with overexpression and/or (abnormal) activation of c-Met. The cancer may be a solid cancer or a blood cancer. For example, the cancer may be at least one selected from the group consisting of squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastrointestinal cancer, gastric cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, head and neck cancers, brain cancer, and osteosarcoma but is not limited thereto.

The prevention and/or treatment effects of the cancers may include effects of not only suppressing the growth of the cancer cells but also suppressing progression of cancers due to migration, invasion, and metastasis thereof. Therefore, the cancer may include a primary cancer or a metastatic cancer.

The biomarker and/or reference marker suggested by this description may be useful in selecting a subject suitable for application of an anti-c-Met antibody at a high accuracy, thereby achieving an individual therapy so that the anti-c-Met antibody can exhibit the greatest effect on the individual patient. The biomarker and/or reference marker may also be useful in clinical test of the anti-c-Met antibody.

EXAMPLES

Hereafter, the present invention will be described in detail by examples.

The following examples are intended merely to illustrate the invention and are not construed to restrict the invention.

Reference Example 1

Construction of Anti-c-Met Antibody 1.1. Production of "AbF46", a Mouse Antibody to c-Met
1.1.1. Immunization of Mouse To obtain immunized mice necessary for the development of a hybridoma cell line, each of five BALB/c mice (Japan SLC, Inc.), 4 to 6 weeks old, was intraperitoneally injected with a mixture of 100 μg of human c-Met/Fc fusion protein (R&D Systems) and one volume of complete Freund's adjuvant. Two weeks after the injection, a second intraperitoneal injection was conducted on the same mice with a mixture of 50 μg of human c-Met/Fc protein and one volume of incomplete Freund's adjuvant. One week after the second immunization, the immune response was finally boosted. Three days later, blood was taken from the tails of the mice and the sera were 1/1000 diluted in PBS and used to examine a titer of antibody to c-Met by ELISA. Mice found to have a sufficient antibody titer were selected for use in the cell fusion process.

1.1.2. Cell Fusion and Production of Hybridoma

Three days before cell fusion, BALB/c mice (Japan SLC, Inc.) were immunized with an intraperitoneal injection of a mixture of 50 μg of human c-Met/Fc fusion protein and one volume of PBS. The immunized mice were anesthetized before excising the spleen from the left half of the body. The spleen was meshed to separate splenocytes which were then suspended in a culture medium (DMEM, GIBCO, Invitrogen). The cell suspension was centrifuged to recover the cell layer. The splenocytes thus obtained ($1 \times 10^8$ cells) were mixed with myeloma cells (Sp2/0) ($1 \times 10^8$ cells), followed by spinning to give a cell pellet. The cell pellet was slowly suspended, treated with 45% polyethylene glycol (PEG) (1 mL) in DMEM for 1 min at 37° C., and supplemented with 1 mL of DMEM. To the cells was added 10 mL of DMEM over 10 min, after which incubation was conducted in a water bath at 37° C. for 5 min. Then the cell volume was adjusted to 50 mL before centrifugation. The cell pellet thus formed was resuspended at a density of $1\sim2\times10^5$ cells/mL in a selection medium (HAT medium) and 0.1 mL of the cell suspension was allocated to each well of 96-well plates which were then incubated at 37° C. in a $CO_2$ incubator to establish a hybridoma cell population.

1.1.3. Selection of Hybridoma Cells Producing Monoclonal Antibodies to c-Met Protein From the hybridoma cell population established in Reference Example 1.1.2, hybridoma cells which showed a specific response to c-Met protein were screened by ELISA using human c-Met/Fc fusion protein and human Fc protein as antigens.

Human c-Met/Fc fusion protein was seeded in an amount of 50 µL (2 µg/mL)/well to microtiter plates and allowed to adhere to the surface of each well. The antibody that remained unbound was removed by washing. For use in selecting the antibodies that do not bind c-Met but recognize Fc, human Fc protein was attached to the plate surface in the same manner.

The hybridoma cell culture obtained in Reference Example 1.1.2 was added in an amount of 50 µL to each well of the plates and incubated for 1 hour. The cells remaining unreacted were washed out with a sufficient amount of Tris-buffered saline and Tween 20 (TBST). Goat anti-mouse IgG-horseradish peroxidase (HRP) was added to the plates and incubated for 1 hour at room temperature. The plates were washed with a sufficient amount of TBST, followed by reacting the peroxidase with a substrate (OPD). Absorbance at 450 nm was measured on an ELISA reader.

Hybridoma cell lines which secrete antibodies that specifically and strongly bind to human c-Met but not human Fc were selected repeatedly. From the hybridoma cell lines obtained by repeated selection, a single clone producing a monoclonal antibody was finally separated by limiting dilution. The single clone of the hybridoma cell line producing the monoclonal antibody was deposited with the Korean Cell Line Research Foundation, an international depository authority located at Yungun-Dong, Jongno-Gu, Seoul, Korea, on Oct. 6, 2009, with Accession No. KCLRF-BP-00220 according to the Budapest Treaty (refer to Korean Patent Laid-Open Publication No. 2011-0047698).

1.1.4. Production and Purification of Monoclonal Antibody

The hybridoma cell line obtained in Reference Example 1.1.3 was cultured in a serum-free medium, and the monoclonal antibody (AbF46) was produced and purified from the cell culture.

First, the hybridoma cells cultured in 50 mL of a medium (DMEM) supplemented with 10% (v/v) FBS were centrifuged and the cell pellet was washed twice or more with 20 mL of PBS to remove the FBS therefrom. Then, the cells were resuspended in 50 mL of DMEM and incubated for 3 days at 37° C. in a $CO_2$ incubator.

After the cells were removed by centrifugation, the supernatant was stored at 4° C. before use or immediately used for the separation and purification of the antibody. An AKTA system (GE Healthcare) equipped with an affinity column (Protein G agarose column; Pharmacia, USA) was used to purify the antibody from 50 to 300 mL of the supernatant, followed by concentration with a filter (Amicon). The antibody in PBS was stored before use in the following examples.

1.2. Construction of chAbF46, a Chimeric Antibody to c-Met

A mouse antibody is apt to elicit immunogenicity in humans. To solve this problem, chAbF46, a chimeric antibody, was constructed from the mouse antibody AbF46 produced in Experimental Example 1.1.4 by replacing the constant region, but not the variable region responsible for antibody specificity, with an amino sequence of the human IgG1 antibody.

In this regard, a gene was designed to include the nucleotide sequence of "EcoRI-signal sequence-VH-NheI-CH-TGA-XhoI" (SEQ ID NO: 38) for a heavy chain and the nucleotide sequence of "EcoRI-signal sequence-VL-BsiWI-CL-TGA-XhoI" (SEQ ID NO: 39) for a light chain and synthesized. Then, a DNA fragment having the heavy chain nucleotide sequence (SEQ ID NO: 38) and a DNA fragment having the light chain nucleotide sequence (SEQ ID NO: 39) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen), and a pcDNA™3.3-TOPO TA Cloning Kit (Cat no. 8300-01), respectively.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day prior to the transient expression, the cells were provided in the concentration of $5 \times 10^5$ cells/ml, and after 24 hours, when the cell number reached $1 \times 10^6$ cells/ml, the transient expression was performed. A transfection was performed by a liposomal reagent method using Freestyle™ MAX reagent (Invitrogen), wherein in a 15 ml tube, the DNA was provided in the mixture ratio of 1:1 (heavy chain DNA: light chain DNA) and mixed with 2 ml of OptiPro™ SFM (Invitrogen) (tube A), and in another 15 ml tube, 100 ul (microliter) of Freestyle™ MAX reagent and 2 ml of OptiPro™ SFM were mixed (tube B), followed by mixing tube A and tube B and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

Afterwards, the cells were incubated in DMEM supplemented with 10% (v/v) FBS for 5 hours at 37° C. under a 5% $CO_2$ condition and then in FBS-free DMEM for 48 hours at 37° C. under a 5% $CO_2$ condition.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a chimeric antibody AbF46 (hereinafter referred to as "chAbF46").

1.3. Construction of Humanized Antibody huAbF46 from Chimeric Antibody chAbF46

1.3.1. Heavy Chain Humanization

To design two domains H1-heavy and H3-heavy, human germline genes which share the highest identity/homology with the VH gene of the mouse antibody AbF46 purified in Reference Example 1.2 were analyzed. An Ig BLAST (www.ncbi.nlm.nih.gov/igblast/) result revealed that VH3-71 has an identity/identity/homology of 83% at the amino acid level. CDR-H1, CDR-H2, and CDR-H3 of the mouse antibody AbF46 were defined according to Kabat numbering. A design was made to introduce the CDR of the mouse antibody AbF46 into the framework of VH3-71. Hereupon, back mutations to the amino acid sequence of the mouse AbF46 were conducted at positions 30 (S→T), 48 (V→L), 73 (D→N), and 78 (T→L). Then, H1 was further mutated at positions 83 (R→K) and 84 (A→T) to finally establish H1-heavy (SEQ ID NO: 40) and H3-heavy (SEQ ID NO: 41).

For use in designing H4-heavy, human antibody frameworks were analyzed by a BLAST search. The result revealed that the VH3 subtype, known to be most stable, is very similar in framework and sequence to the mouse antibody AbF46. CDR-H1, CDR-H2, and CDR-H3 of the mouse antibody AbF46 were defined according to Kabat numbering and introduced into the VH3 subtype to construct H4-heavy (SEQ ID NO: 42).

1.3.2. Light Chain Humanization

To design two domains, H1-light (SEQ ID NO: 43) and H2-light (SEQ ID NO: 44), human germline genes which share the highest identity/homology with the VH gene of the mouse antibody AbF46 were analyzed. An Ig BLAST search result revealed that VK4-1 has a identity/homology of 75% at the amino acid level. CDR-L1, CDR-L2, and CDR-L3 of the mouse antibody AbF46 were defined according to Kabat numbering. A design was made to introduce the CDR of the mouse antibody AbF46 into the framework of VK4-1. Hereupon, back mutations to the amino acid sequence of the mouse AbF46 were conducted at positions 36 (Y→H), 46 (L→M), and 49 (Y→I). Only one back mutation was conducted at position 49 (Y→I) on H2-light.

To design H3-light (SEQ ID NO: 45), human germline genes which share the highest identity/homology with the VL gene of the mouse antibody AbF46 were analyzed by a search for BLAST. As a result, VK2-40 was selected. VL and VK2-40 of the mouse antibody AbF46 were found to have an identity/homology of 61% at an amino acid level. CDR-L1, CDR-L2, and CDR-L3 of the mouse antibody were defined according to Kabat numbering and introduced into the framework of VK4-1. Back mutations were conducted at positions 36 (Y→H), 46 (L→M), and 49 (Y→I) on H3-light.

For use in designing H4-light (SEQ ID NO: 46), human antibody frameworks were analyzed. A Blast search revealed that the Vk1 subtype, known to be the most stable, is very similar in framework and sequence to the mouse antibody AbF46. CDR-L1, CDR-L2, and CDR-L3 of the mouse antibody AbF46 were defined according to Kabat numbering and introduced into the Vk1 subtype. Hereupon, back mutations were conducted at positions 36 (Y→H), 46 (L→M), and 49 (Y→I) on H4-light.

Thereafter, DNA fragments having the heavy chain nucleotide sequences (H1-heavy: SEQ ID NO: 47, H3-heavy: SEQ ID NO: 48, H4-heavy: SEQ ID NO: 49) and DNA fragments having the light chain nucleotide sequences (H1-light: SEQ ID NO: 50, H2-light: SEQ ID NO: 51, H3-light: SEQ ID NO: 52, H4-light: SEQ ID NO: 53) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™3.3-TOPO TA Cloning Kit (Cat no. 8300-01), respectively, so as to construct recombinant vectors for expressing a humanized antibody.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (Invitrogen), wherein in a 15 ml tube, the DNA was provided in the mixture ratio of 1:1 (heavy chain DNA: light chain DNA) and mixed with 2 ml of OptiPro™ SFM (Invitrogen) (tube A), and in another 15 ml tube, 100 ul (microliter) of Freestyle™ MAX reagent and 2 ml of OptiPro™ SFM were mixed (tube B), followed by mixing tube A and tube B and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a humanized antibody AbF46 (hereinafter referred to as "huAbF46"). The humanized antibody huAbF46 used in the following examples comprised a combination of H4-heavy (SEQ ID NO: 42) and H4-light (SEQ ID NO: 46).

1.4. Construction of scFV Library of huAbF46 Antibody

For use in constructing an scFv of the huAbF46 antibody from the heavy and light chain variable regions of the huAbF46 antibody, a gene was designed to have the structure of "VH-linker-VL" for each of the heavy and the light chain variable region, with the linker having the amino acid sequence "GLGGLGGGGSGGGGSGGSSGVGS" (SEQ ID NO: 54). A polynucleotide sequence (SEQ ID NO: 55) encoding the designed scFv of huAbF46 was synthesized in Bioneer and an expression vector for the polynucleotide had the nucleotide sequence of SEQ ID NO: 56.

After expression, the product was found to exhibit specificity to c-Met.

1.5. Construction of Library Genes for Affinity Maturation 1.5.1. Selection of Target CDRs and Synthesis of Primers The affinity maturation of huAbF46 was achieved in the following steps. First, six complementary determining regions (CDRs) were defined according to Kabat numbering. The CDRs are given in Table 7, below.

TABLE 7

| CDR | Amino Acid Sequence |
|---|---|
| CDR-H1 | DYYMS<br>(SEQ ID NO: 1) |

TABLE 7-continued

| CDR | Amino Acid Sequence |
|---|---|
| CDR-H2 | FIRNKANGYTTEYSASVKG (SEQ ID NO: 2) |
| CDR-H3 | DNWFAY (SEQ ID NO: 3) |
| CDR-L1 | KSSQSLLASGNQNNYLA (SEQ ID NO: 10) |
| CDR-L2 | WASTRVS (SEQ ID NO: 11) |
| CDR-L3 | QQSYSAPLT (SEQ ID NO: 12) |

For use in the introduction of random sequences into the CDRs of the antibody, primers were designed as follows. Conventionally, N codons were utilized to introduce bases at the same ratio (25% A, 25% G, 25% C, 25% T) into desired sites of mutation. In this experiment, the introduction of random bases into the CDRs of huAbF46 was conducted in such a manner that, of the three nucleotides per codon in the wild-type polynucleotide encoding each CDR, the first and second nucleotides conserved over 85% of the entire sequence while the other three nucleotides were introduced at the same percentage (each 5%) and that the same possibility was imparted to the third nucleotide (33% G, 33% C, 33% T).

1.5.2. Construction of a Library of huAbF46 Antibodies and Affinity for c-Met

The construction of antibody gene libraries through the introduction of random sequences was carried out using the primers synthesized in the same manner as in Reference Example 1.5.1. Two PCR products were obtained using a polynucleotide covering the scFV of huAbF46 as a template, and were subjected to overlap extension PCR to give scFv library genes for huAbF46 antibodies in which only desired CDRs were mutated. Libraries targeting each of the six CDRs prepared from the scFV library genes were constructed.

The affinity for c-Met of each library was compared to that of the wildtype. Most libraries were lower in affinity for c-Met, compared to the wild-type. The affinity for c-Met was retained in some mutants.

1.6. Selection of Antibody with Improved Affinity from Libraries

After affinity maturation of the constructed libraries for c-Met, the nucleotide sequence of scFv from each clone was analyzed. The nucleotide sequences thus obtained are summarized in Table 8 and were converted into IgG forms. Four antibodies which were respectively produced from clones L3-1, L3-2, L3-3, and L3-5 were used in the subsequent experiments.

TABLE 8

| Clone | Library constructed | CDR Sequence |
|---|---|---|
| H11-4 | CDR-H1 | PEYYMS (SEQ ID NO: 22) |
| YC151 | CDR-H1 | PDYYMS (SEQ ID NO: 23) |
| YC193 | CDR-H1 | SDYYMS (SEQ ID NO: 24) |
| YC244 | CDR-H2 | RNNANGNT (SEQ ID NO: 25) |
| YC321 | CDR-H2 | RNKVNGYT (SEQ ID NO: 26) |
| YC354 | CDR-H3 | DNWLSY (SEQ ID NO: 27) |
| YC374 | CDR-H3 | DNWLTY (SEQ ID NO: 28) |
| L1-1 | CDR-L1 | KSSHSLLASGNQNNYLA (SEQ ID NO: 29) |
| L1-3 | CDR-L1 | KSSRSLLSSGNHKNYLA (SEQ ID NO: 30) |
| L1-4 | CDR-L1 | KSSKSLLASGNQNNYLA (SEQ ID NO: 31) |
| L1-12 | CDR-L1 | KSSRSLLASGNQNNYLA (SEQ ID NO: 32) |
| L1-22 | CDR-L1 | KSSHSLLASGNQNNYLA (SEQ ID NO: 33) |
| L2-9 | CDR-L2 | WASKRVS (SEQ ID NO: 34) |
| L2-12 | CDR-L2 | WGSTRVS (SEQ ID NO: 35) |
| L2-16 | CDR-L2 | WGSTRVP (SEQ ID NO: 36) |
| L3-1 | CDR-L3 | QQSYSRPYT (SEQ ID NO: 13) |
| L3-2 | CDR-L3 | GQSYSRPLT (SEQ ID NO: 14) |
| L3-3 | CDR-L3 | AQSYSHPFS (SEQ ID NO: 15) |
| L3-5 | CDR-L3 | QQSYSRPFT (SEQ ID NO: 16) |
| L3-32 | CDR-L3 | QQSYSKPFT (SEQ ID NO: 37) |

1.7. Conversion of Selected Antibodies into IgG

Respective polynucleotides encoding heavy chains of the four selected antibodies were designed to have the structure of "EcoRI-signal sequence-VH-NheI-CH-XhoI" (SEQ ID NO: 38). The heavy chains of huAbF46 antibodies were used as they were because their amino acids were not changed during affinity maturation. In the case of the hinge region, however, the U6-HC7 hinge (SEQ ID NO: 57) was employed instead of the hinge of human IgG1. Genes were also designed to have the structure of "EcoRI-signal sequence-VL-BsiWI-CL-XhoI" for the light chain. Polypeptides encoding light chain variable regions of the four antibodies which were selected after the affinity maturation were synthesized in Bioneer. Then, a DNA fragment having the heavy chain nucleotide sequence (SEQ ID NO: 38) and DNA fragments having the light chain nucleotide sequences (DNA fragment comprising L3-1-derived CDR-L3: SEQ ID NO: 58, DNA fragment comprising L3-2-derived CDR-L3: SEQ ID NO: 59, DNA fragment comprising L3-3-derived CDR-L3: SEQ ID NO: 60, and DNA fragment comprising L3-5-derived CDR-L3: SEQ ID NO: 61) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™3.3-TOPO TA Cloning Kit (Cat no. 8300-01), respectively, so as to construct recombinant vectors for expressing affinity-matured antibodies.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day prior to initiation of the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (Invitrogen), wherein in a 15 ml tube, the DNA was provided in the mixture ratio of 1:1 (heavy chain DNA:light chain DNA) and mixed with 2 ml of OptiPro™ SFM (Invitrogen) (tube A), and in another 15 ml tube, 100 ul (microliter) of Freestyle™ MAX reagent and 2 ml of OptiPro™ SFM were mixed (tube B), followed by mixing tube A and tube B and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify four affinity-matured antibodies (hereinafter referred to as "huAbF46-H4-A1 (L3-1 origin), huAbF46-H4-A2 (L3-2 origin), huAbF46-H4-A3 (L3-3 origin), and huAbF46-H4-A5 (L3-5 origin)," respectively).

1.8. Construction of Constant Region- and/or Hinge Region-Substituted huAbF46-H4-A1

Among the four antibodies selected in Reference Example 1.7, huAbF46-H4-A1 was found to be the highest in affinity for c-Met and the lowest in Akt phosphorylation and c-Met degradation degree. In the antibody, the hinge region, or the constant region and the hinge region, were substituted.

The antibody huAbF46-H4-A1 (U6-HC7) was composed of a heavy chain comprising the heavy chain variable region of huAbF46-H4-A1, U6-HC7 hinge, and the constant region of human IgG1 constant region, and a light chain comprising the light chain variable region of huAbF46-H4-A1 and human kappa constant region. The antibody huAbF46-H4-A1 (IgG2 hinge) was composed of a heavy chain comprising a heavy chain variable region, a human IgG2 hinge region, and a human IgG1 constant region, and a light chain comprising the light chain variable region of huAbF46-H4-A1 and a human kappa constant region. The antibody huAbF46-H4-A1 (IgG2 Fc) was composed of the heavy chain variable region of huAbF46-H4-A1, a human IgG2 hinge region, and a human IgG2 constant region, and a light chain comprising the light variable region of huAbF46-H4-A1 and a human kappa constant region. Hereupon, the histidine residue at position 36 on the human kappa constant region of the light chain was changed to tyrosine in all of the three antibodies to increase antibody production.

For use in constructing the three antibodies, a polynucleotide (SEQ ID NO: 63) encoding a polypeptide (SEQ ID NO: 62) composed of the heavy chain variable region of huAbF46-H4-A1, a U6-HC7 hinge region, and a human IgG1 constant region, a polynucleotide (SEQ ID NO: 65) encoding a polypeptide (SEQ ID NO: 64) composed of the heavy chain variable region of huAbF46-H4-A1, a human IgG2 hinge region, and a human IgG1 constant region, a polynucleotide (SEQ ID NO: 67) encoding a polypeptide (SEQ ID NO: 66) composed of the heavy chain variable region of huAbF46-H4-A1, a human IgG2 hinge region, and a human IgG2 constant region, and a polynucleotide (SEQ ID NO: 69) encoding a polypeptide (SEQ ID NO: 68) composed of the light chain variable region of huAbF46-H4-A1, with a tyrosine residue instead of histidine at position 36, and a human kappa constant region were synthesized in Bioneer. Then, the DNA fragments having heavy chain nucleotide sequences were inserted into a pOptiVEC™-TOPO TA Cloning Kit enclosed in an OptiCHO™ Antibody Express Kit (Cat no. 12762-019, Invitrogen) while DNA fragments having light chain nucleotide sequences were inserted into a pcDNA™3.3-TOPO TA Cloning Kit (Cat no. 8300-01) so as to construct vectors for expressing the antibodies.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (Invitrogen), wherein in a 15 ml tube, the DNA was provided in the mixture ratio of 1:1 (heavy chain DNA:light chain DNA) and mixed with 2 ml of OptiPro™ SFM (Invitrogen) (tube A), and in another 15 ml tube, 100 ul (microliter) of Freestyle™ MAX reagent and 2 ml of OptiPro™ SFM were mixed (tube B), followed by mixing tube A and tube B and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with IgG elution buffer (Thermo Scientific, 21004). The buffer was exchanged with PBS to finally purify three antibodies (huAbF46-H4-A1 (U6-HC7), huAbF46-H4-A1 (IgG2 hinge), and huAbF46-H4-A1 (IgG2 Fc)). Among the three antibodies, huAbF46-H4-A1 (IgG2 Fc) was representatively selected for the following examples, and referred as anti-c-Met antibody L3-1Y/IgG2.

Reference Example 2

Preparation of Xenograft Models and Test Samples

Fourteen species of mouse xenograft models grafted with patient driven tumor tissues (tumor: Non-small cell lung cancer (NSCLC)) through intraperitoneal injection were obtained from Oncotest GmbH (Germany).

To the 14 species of mouse xenograft models, a candidate drug final form (L3-1Y/IgG2: n (of each model)=10) and empty vehicle (control: n (of each model)=10) are administered respectively, and the tumor size in each model was measured, thereby determining the response to the antibody.

L3-1Y/IgG2 was administered once a week at the amount of 5 mg/kg (in the case of control, PBS buffer was administered), wherein the administration was started from the time when the tumor size in the mouse xenograft model reaches 500 mm³ or more. The experiment was conducted for 6 weeks in total, and stopped when the tumor size reaches 2000 mm³ or more.

The tumor size was calculated by the following formula:

Tumor size (mm³)=(long diameter*short diameter*short diameter)/2

The determination of an efficacy group was carried out through ANOVA analysis, and the cases where p-value is 0.05 or less were excluded. That is, the assumption that the distribution of tumor size in an antibody treated group is not changed compared to that of an antibody non-treated group was tested by ANOVA analysis, wherein a group is determined as a non-efficacy group when p-value is 0.05 or less, and a group is determined as an efficacy group when p-value is more than 0.05.

The responding results from the above mouse xenograft models for L3-1Y/IgG2 treatment are shown in Table 9:

TABLE 9

|  | Responding (efficacy) group | Non-responding (non-efficacy) group |
| --- | --- | --- |
| Sample | LXFA1647, LXFA2158, LXFA526, LXFA623 | LXFA1041, LXFA162, LXFA1848, LXFA2201, LXFA289, LXFA297, LXFA400, LXFA749, LXFA923, LXFA983 |

Tumor tissues were extracted from the mice after finishing the above experiment, a part of them were prepared as a formalin fixed paraffin embedded (FFPE) block, and the rest were subjected to total RNA extraction using Qiagen RNeasy Mini Kit (Cat. No. 74104) according to manufacturer's protocol.

The prepared FFPE block was used for measuring surface expression c-MET using Ventana MET IHC (immunohistochemistry) (Roche; US2013089541 A1) according to manufacturer's standard protocol, and the extracted total RNA was used for measuring c-MET mRNA expression by Real Time PCR (RT-PCR) (MET sense primer: CCTTGAACA-GAATCACTG (SEQ ID NO: 272); MET anti-sense primer: CCATGTTTCATGTATGGTA (SEQ ID NO: 273)).

The results obtained from Ventana MET IHC are shown in FIG. 1A. In this assay, when the IHC score is 2~3, the sample is determined as an efficacy group. As shown in FIG. 1A, even LXFA297, LXFA983, and LXFA1041, which are non-efficacy groups, have IHC score of 2~3, indicating that IHC assay does not provide a high accurate selection for an efficacy or non-efficacy group (accuracy: about 50%).

Figure 1B:
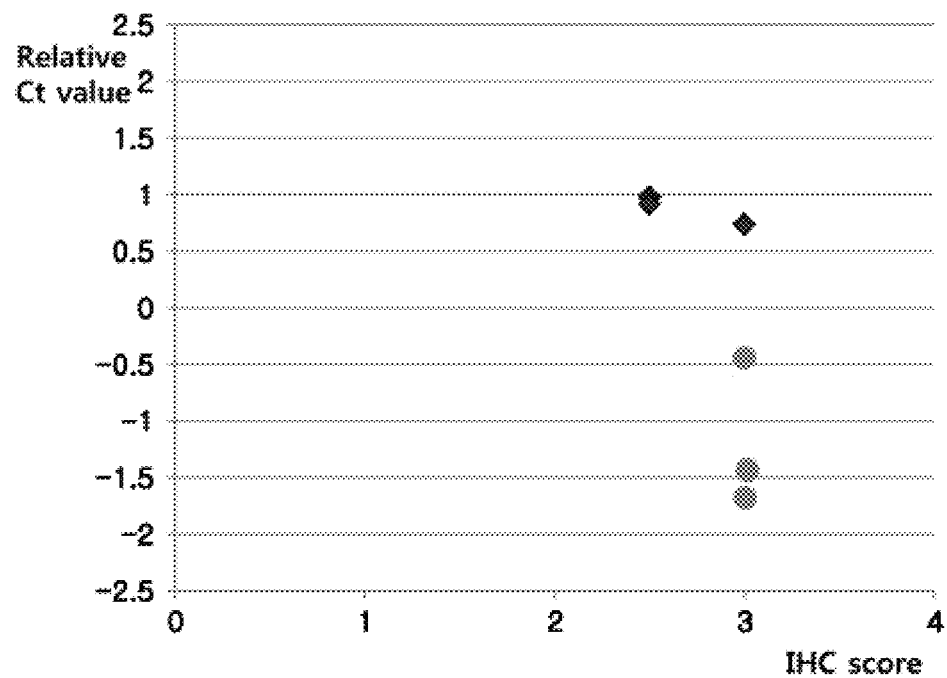
FIG. 1B is a graph showing relative Ct values obtained by RT-PCR, indicating which model is a non-responding (non-efficacy) group or a responding (efficacy) group (Y axis: relative Ct value, X axis: IHC score, ♦: non-responding (non-efficacy) group, ●: responding (efficacy) group).

Meanwhile, the obtained RT-PCR results of six models (LXFA297, LXFA983, LXFA1041, LXFA623, LXFA526, and LXFA1647), which are determined as efficacy groups in FIG. 1A, are shown in FIG. 1B. In FIG. 1B, Y axis is Ct value measured from RT-PCR, X axis is the above obtained IHC score, "♦" refers to a non-efficacy group, and "●" refers to an efficacy group. As shown in FIG. 1B, according to the result of RT-PCR, the Ct values in the non-efficacy groups are all 0 or more, and the Ct values in the efficacy groups are all less than 0. Therefore, the selection according to RT-PCR results provides more accurate selection of non-efficacy or efficacy group (accuracy: about 71% to about 93%), compared to pre-existing IHC assay. Therefore, if RT-PCR result is mainly used mainly and IHC score is additionally considered, more accurate selection can be achieved (for example, when Ct value of RT-PCR is less than 0 and IHC score is 2 to 3, the sample can be selected as an efficacy group).

Example 1

Selection of Biomarkers

Using the xenograft sample (14 species of pre-clinical sample) in Reference Example 2 for test of efficacy of c-Met antibody L3-1Y/IgG2 prepared in Reference Example 1, the expression levels of genes in L3-1Y/IgG2 efficacy and non-efficacy groups were measured. Using the obtained gene expression levels, the difference ($\Delta$ log 2(exp)) of gene expression between efficacy and non-efficacy groups was determined, and genes having high difference between efficacy and non-efficacy groups were selected.

The difference of gene expression was measured using Affymatrix human u133 plus 2.0 microarray experiment raw data (cell file), and using a microarray analysis console provided by Affymatrix, log 2(probe intensity) value of each probe was measured to be used as a standard. The used probes are summarized in Table 10:

TABLE 10

| Gene | Probe Sequence(5'-3') | Probe Interrogation | Target Strandedness |
| --- | --- | --- | --- |
| THSD7A (213894_at) | TTTTTAAGACTTCTTGTCTCTCTCC (SEQ ID NO: 110) | 4486 | Antisense |
|  | AACGAGTCCTCAAGTTCAGTATTTT (SEQ ID NO: 111) | 4549 | Antisense |
|  | TACAATACGTTTCTACTTTCCCTGA (SEQ ID NO: 112) | 4614 | Antisense |
|  | TGATTTTCAAACTGGTTGCCTGCAT (SEQ ID NO: 113) | 4636 | Antisense |
|  | GGAAGGCACATTTTTGCACTATATT (SEQ ID NO: 114) | 4675 | Antisense |
|  | AGTGCAGCACGATAGGCGCTTAACC (SEQ ID NO: 115) | 4700 | Antisense |
|  | TAGGCGCTTAACCAGTATTGCCATA (SEQ ID NO: 116) | 4712 | Antisense |

TABLE 10-continued

| Gene | Probe Sequence(5'-3') | Probe Interrogation | Target Strandedness |
|---|---|---|---|
| | GTATTGCCATAGAAACTGCCTCTTT (SEQ ID NO: 117) | 4726 | Antisense |
| | AACTGCCTCTTTTCATGTGGGATGA (SEQ ID NO: 118) | 4739 | Antisense |
| | GACATTTGCAAGTTCTTGTATCCTG (SEQ ID NO: 119) | 4791 | Antisense |
| | GCTATTACACCTGCTGTACACACAC (SEQ ID NO: 120) | 4858 | Antisense |
| THSD7A (214920_at) | ACTTCTCTATTGACACTTTTACCTC (SEQ ID NO: 121) | 2072 | Antisense |
| | TGACACTTTTACCTCACCGAGGGGG (SEQ ID NO: 122) | 2082 | Antisense |
| | GAACTGCTGTTCCCTAGAATGAAGG (SEQ ID NO: 123) | 2118 | Antisense |
| | AGAATGAAGGTCTGTTGTTTGGTTT (SEQ ID NO: 124) | 2133 | Antisense |
| | TTATATGATTTTGCTGGACTATTTC (SEQ ID NO: 125) | 2194 | Antisense |
| | GGACTATTTCACTAGAAACCACGTA (SEQ ID NO: 126) | 2209 | Antisense |
| | GAATAGGACTAACTGATCTCTTTTG (SEQ ID NO: 127) | 2234 | Antisense |
| | AAAGGGGCTGATTTGCTTATTCATC (SEQ ID NO: 128) | 2259 | Antisense |
| | ATGTGGACAGTAATCTTAATTTCAA (SEQ ID NO: 129) | 2299 | Antisense |
| | GAGGATACTACGGTGTAGCTTAAGT (SEQ ID NO: 130) | 2334 | Antisense |
| | AGCACAAATTACTTCTAACAAGGCA (SEQ ID NO: 131) | 2407 | Antisense |
| THSD7A (230008_at) | GTATTTTCCCCTACGTAATGTACAT (SEQ ID NO: 132) | 177 | Antisense |
| | GTACATGTCTTTAGGCCACAGTATT (SEQ ID NO: 133) | 196 | Antisense |
| | AGGTGGCAGTGGTCATTGTAGCTTA (SEQ ID NO: 134) | 255 | Antisense |
| | TAATCAGACCCCTGTTAAGTTCCTG (SEQ ID NO: 135) | 278 | Antisense |
| | CAAGGTAAATTCACGTCTTCCTTCT (SEQ ID NO: 136) | 310 | Antisense |
| | AATAGACCTCTCACACACTTATTTA (SEQ ID NO: 137) | 346 | Antisense |
| | GTCTCTTTCTACTCTTGACAGCTAT (SEQ ID NO: 138) | 420 | Antisense |
| | CTTGACAGCTATTCTTACCTACTTC (SEQ ID NO: 139) | 433 | Antisense |
| | TTCCCACTAAACATGCCCAATTTTT (SEQ ID NO: 140) | 455 | Antisense |
| | TCCTATATTTCCTTCCCTATTAGAA (SEQ ID NO: 141) | 499 | Antisense |
| | GAATCAAAGTGTCACTCACTCAGAG (SEQ ID NO: 142) | 521 | Antisense |
| MET (213816_s_at) | GTTGTCGACACCTACTATGATGATC (SEQ ID NO: 144) | 567 | Antisense |
| | CAGCGTCAACAGAGGGACCTGCCAG (SEQ ID NO: 145) | 608 | Antisense |
| | TTTCCCCACAATCATACTGCTGACA (SEQ ID NO: 146) | 642 | Antisense |
| | AGATAGAAGAGCCCAGCCAGTGTCC (SEQ ID NO: 147) | 700 | Antisense |
| | GGAGCCAAAGTCCTTTCATCTGTAA (SEQ ID NO: 148) | 747 | Antisense |
| | TAAAGGACCGGTTCATCAACTTCTT (SEQ ID NO: 149) | 769 | Antisense |
| | ATTTCCCAGATCATCCATTGCATTC (SEQ ID NO: 150) | 820 | Antisense |
| | ACGGACCAGTCCTACATTGATGTTT (SEQ ID NO: 151) | 894 | Antisense |
| | GAGTTCAGAGATTCTTACCCCATTA (SEQ ID NO: 152) | 924 | Antisense |
| | CTAGATGCTCAGACTTTTCACACAA (SEQ ID NO: 153) | 1011 | Antisense |
| | ATCAGGTTCTGTTCCATAAACTCTG (SEQ ID NO: 154) | 1041 | Antisense |

TABLE 10-continued

| Gene | Probe Sequence(5'-3') | Probe Interrogation | Target Strandedness |
|---|---|---|---|
| RAB31 (217763_s_at) | AACATTGTAATGGCCATCGCTGGAA (SEQ ID NO: 156) | 400 | Antisense |
| | GAAACAAGTGCGACCTCTCAGATAT (SEQ ID NO: 157) | 422 | Antisense |
| | GGAGGTTCCCCTGAAGGATGCTAAG (SEQ ID NO: 158) | 450 | Antisense |
| | TACGCTGAATCCATAGGTGCCATCG (SEQ ID NO: 159) | 478 | Antisense |
| | GTGCCATCGTGGTTGAGACAAGTGC (SEQ ID NO: 160) | 494 | Antisense |
| | TTCAAGGAATCAGCCGCCAGATCCC (SEQ ID NO: 161) | 548 | Antisense |
| | TGAGAAGCCAACCATGCAAGCCAGC (SEQ ID NO: 162) | 618 | Antisense |
| | CGTGGTCCACGGTACTTGAAGAAGC (SEQ ID NO: 163) | 666 | Antisense |
| | ATCCTGTGCACTGCTGAAGGACCCT (SEQ ID NO: 164) | 701 | Antisense |
| | GAGTGAGCACACTGGCTTTGCATCC (SEQ ID NO: 165) | 758 | Antisense |
| | ACCACCACAAAATGGCCTTTAGTGT (SEQ ID NO: 166) | 856 | Antisense |
| RAB31 (217764_s_at) | GAATATGACGTTACCTTGCAGACTA (SEQ ID NO: 167) | 3398 | Antisense |
| | TTTTTTGTGTGGGCTCCAGTTCTCA (SEQ ID NO: 168) | 3570 | Antisense |
| | GTTCTGCAATGCTCATGGCAAGTTG (SEQ ID NO: 169) | 3597 | Antisense |
| | ACCGACTGGGTATCTAGCTTACTGT (SEQ ID NO: 170) | 3668 | Antisense |
| | ATCATTGTTGAAACCAGACCCTGTA (SEQ ID NO: 171) | 3699 | Antisense |
| | AGACCCTGTAGTCCAGTGGTGCTGC (SEQ ID NO: 172) | 3714 | Antisense |
| | TAAAGAGCTTCCATCTGGGCTGGAC (SEQ ID NO: 173) | 3776 | Antisense |
| | TGGACCCAGTTCTTGCACATACAAG (SEQ ID NO: 174) | 3796 | Antisense |
| | GCACATACAAGACACCGCTGCAGTC (SEQ ID NO: 175) | 3810 | Antisense |
| | ACCGCTGCAGTCAGCTAGGACCTTT (SEQ ID NO: 176) | 3823 | Antisense |
| | GGTTTAACACACACTGATTCATACT (SEQ ID NO: 177) | 3915 | Antisense |
| FAM126A (223625_at) | GACTTACTTTAACAACCAGCCAATC (SEQ ID NO: 179) | 1447 | Antisense |
| | AATCCCTACCTAAGCCTAGTAGCCA (SEQ ID NO: 180) | 1468 | Antisense |
| | GCCATGGTTTGGCTAAGACCGCAGC (SEQ ID NO: 181) | 1489 | Antisense |
| | GTCAGTGGTGTCACAGTCCCACATA (SEQ ID NO: 182) | 1542 | Antisense |
| | ACATAACCCGTCATCTGCTGTTGGT (SEQ ID NO: 183) | 1562 | Antisense |
| | GCCAATAGGTTTTCCGCTTGTAGTC (SEQ ID NO: 184) | 1605 | Antisense |
| | GCAGAGACCTCCTAGTATTAGCATT (SEQ ID NO: 185) | 1697 | Antisense |
| | TTTTCTCCCATAACCTAGTGAACCT (SEQ ID NO: 186) | 1752 | Antisense |
| | GAAAGTACCCTGGGTCTTTCATCCG (SEQ ID NO: 187) | 1801 | Antisense |
| | CTTTCATCCGTATTCCTGACAGGAG (SEQ ID NO: 188) | 1816 | Antisense |
| | GGAGCCCTGATGTCTTAAATTCTGA (SEQ ID NO: 189) | 1837 | Antisense |
| FAM126A | CCGCGGCTCGGAGCAAGCGGTGCAG (SEQ ID NO: 190) | 33 | Antisense |
| | GGAGCGATTCCCATTCGAGGAGTTT (SEQ ID NO: 191) | 63 | Antisense |
| | TCTCATTTTAATACAACACCCGCCT (SEQ ID NO: 192) | 92 | Antisense |
| | AACACCCGCCTCTTAGAGGCAGCAG (SEQ ID NO: 193) | 106 | Antisense |

TABLE 10-continued

| Gene | Probe Sequence(5'-3') | Probe Interrogation | Target Strandedness |
|---|---|---|---|
| | CAGACCAGTCCAGCCAGGTCAAGGT (SEQ ID NO: 194) | 128 | Antisense |
| | TGTGGACCGCACAACGGGGTGCACA (SEQ ID NO: 195) | 152 | Antisense |
| | TAAACGAGCCCTGGATCTGCAAAGC (SEQ ID NO: 196) | 214 | Antisense |
| | GTGATCCCAACCTTAGCAACATAAT (SEQ ID NO: 197) | 263 | Antisense |
| | TATATGTCAGGTGCCAGTGCTATGG (SEQ ID NO: 198) | 434 | Antisense |
| | ATACCATTTATTACCACTTCTCAGT (SEQ ID NO: 199) | 480 | Antisense |
| | GAGGCTGTAACTCTGGTTGTCGAAA (SEQ ID NO: 200) | 511 | Antisense |
| PHC1 (218338_at) | TTTCACGTACCTTAATCCAATCTTT (SEQ ID NO: 202) | 3474 | Antisense |
| | AGAACTAGGACTGCTCAGCCTTATC (SEQ ID NO: 203) | 3517 | Antisense |
| | GCCCAGGTCTTAATTCTCCAAGAGG (SEQ ID NO: 204) | 3559 | Antisense |
| | GGTGGAATGTCAGGTTGCCTGCCCA (SEQ ID NO: 205) | 3616 | Antisense |
| | AGGGTTTTCTAGCTTGTGTGACAG (SEQ ID NO: 206) | 3652 | Antisense |
| | TTGTCACTTACTCCCTTGTGATTGA (SEQ ID NO: 207) | 3740 | Antisense |
| | TGATTGAATTTTTCTCCTGCATCC (SEQ ID NO: 208) | 3758 | Antisense |
| | AGAGACTTGGTTGGCATCTTCTGCT (SEQ ID NO: 209) | 3806 | Antisense |
| | GGCACATGTGGCTGTTGTCATTCTT (SEQ ID NO: 210) | 3856 | Antisense |
| | TGTTCCCCTCCAATTTATGTTATTT (SEQ ID NO: 211) | 3893 | Antisense |
| | GTACCTGCCTTAGGCACTATTCCTT (SEQ ID NO: 212) | 4002 | Antisense |
| CHML (226350_at) | GCAACTTTGACTTAGTTCATGCTAT (SEQ ID NO: 214) | 2504 | Antisense |
| | CTGTTTTAATTGCATGTGTCCTTAT (SEQ ID NO: 215) | 2542 | Antisense |
| | GTGTCCTTATAGCAGCAGCATTGTG (SEQ ID NO: 216) | 2557 | Antisense |
| | GCAGCATTGTGTATTAGTAGCCTTT (SEQ ID NO: 217) | 2571 | Antisense |
| | AGGGCTTTATAACTGATCTTTTGAC (SEQ ID NO: 218) | 2624 | Antisense |
| | GATCTTTTGACATACTCACTTTGAG (SEQ ID NO: 219) | 2638 | Antisense |
| | CACTTTGAGTGGCATATGCCCAGGA (SEQ ID NO: 220) | 2654 | Antisense |
| | AAGTTTTCTAGCAGTTCCACTCAGA (SEQ ID NO: 221) | 2712 | Antisense |
| | GTTCCACTCAGATAACTTTAAGGGG (SEQ ID NO: 222) | 2725 | Antisense |
| | TGGTGTATTGCTAGTGCTATCACAG (SEQ ID NO: 223) | 2788 | Antisense |
| | ATTGTGTTTACTGATACATGTGAAA (SEQ ID NO: 224) | 2898 | Antisense |
| FAM126A (227239_at) | TCTAGTCCTTTAATGAGCATGAATT (SEQ ID NO: 225) | 1179 | Antisense |
| | TATACTTCTACATTTGTTGCTTAGT (SEQ ID NO: 226) | 1204 | Antisense |
| | ATATTGTCTTCTATACTTTGTAACT (SEQ ID NO: 227) | 1304 | Antisense |
| | ATTTCACGTATTGTTGCTTTCTCTT (SEQ ID NO: 228) | 1449 | Antisense |
| | GTTGCTTTCTCTTATATGGAACTTA (SEQ ID NO: 229) | 1461 | Antisense |
| | GGAACTTATTGTGTACCTCTTACCT (SEQ ID NO: 230) | 1478 | Antisense |
| | GTATTCCTAGAGTTTACATTCCTAA (SEQ ID NO: 231) | 1562 | Antisense |
| | ACGACGACTTTGGCTATTTTTGTGT (SEQ ID NO: 232) | 1594 | Antisense |

TABLE 10-continued

| Gene | Probe Sequence(5'-3') | Probe Interrogation | Target Strandedness |
|---|---|---|---|
| | GTTCCCTACCTTCTTAAGGCTATGG (SEQ ID NO: 233) | 1619 | Antisense |
| | ATTTGTGTAAATGTTCTCCATATGT (SEQ ID NO: 234) | 1680 | Antisense |
| | CAAGTGTTGCCTCTTGTTTTATTGA (SEQ ID NO: 235) | 1721 | Antisense |
| ST8SIA4 (242943_at) | TTTATTTTGCACGGCTCTAAACCTC (SEQ ID NO: 237) | 302 | Antisense |
| | TAAACCTCCATGTTATTTTCCAGTG (SEQ ID NO: 238) | 319 | Antisense |
| | GGTGTAGAAGGTACCAGCTAAAGTG (SEQ ID NO: 239) | 343 | Antisense |
| | AGATGTTCCATGTCATCAGAGATGG (SEQ ID NO: 240) | 402 | Antisense |
| | GGTACCAAAGATTACACTTGTGTTT (SEQ ID NO: 241) | 455 | Antisense |
| | ACTTGTGTTTCTACACAGCAAACCA (SEQ ID NO: 242) | 470 | Antisense |
| | GCTATTAATGTGAAAGTTGTCTCTA (SEQ ID NO: 243) | 543 | Antisense |
| | ATGTTTTTCACACCTTTTGCATTAC (SEQ ID NO: 244) | 611 | Antisense |
| | TTTTCACACCTTTTGCATTACATAA (SEQ ID NO: 245) | 615 | Antisense |
| | AATTTTGTGGAAGCATTTTGCCCTT (SEQ ID NO: 246) | 641 | Antisense |
| | GGAAGCATTTTGCCCTTTAGAATAA (SEQ ID NO: 247) | 649 | Antisense |
| CAV1 (212097_at) | GAATTTCACCTGTAAACCTGAGTCG (SEQ ID NO: 249) | 1175 | Antisense |
| | CAGAAAGCTGCCTGGTATATCCAAA (SEQ ID NO: 250) | 1202 | Antisense |
| | TATTCCTCCTGCTCATATTGTGATT (SEQ ID NO: 251) | 1235 | Antisense |
| | GTCTTCCTGACACTTTAATTACCAA (SEQ ID NO: 252) | 1353 | Antisense |
| | TACCAACCTGTTACCTACTTTGACT (SEQ ID NO: 253) | 1372 | Antisense |
| | GTTACCTACTTTGACTTTTTGCATT (SEQ ID NO: 254) | 1381 | Antisense |
| | ATGTGCTATACTGCATACTTTTTAA (SEQ ID NO: 255) | 1463 | Antisense |
| | AACTGTGTATTCCAAGACATGTCTG (SEQ ID NO: 256) | 1556 | Antisense |
| | CATAGATGCTTAGTCCCTCATGCAA (SEQ ID NO: 257) | 1586 | Antisense |
| | AATTTTTTATCATGCATGTCCTGTA (SEQ ID NO: 258) | 1668 | Antisense |
| | TAAAGGTTACAAGCCTGCACAATAA (SEQ ID NO: 259) | 1691 | Antisense |

Based on the measured expression level differences between efficacy and non-efficacy groups, genes were listed from greatest to smallest.

The obtained results are summarized in Table 11 (in Table 11, greater delta expFold refers to greater expression level difference between efficacy and non-efficacy):

TABLE 11

| gene | Δ exprFold | probeID |
|---|---|---|
| THSD7A | 4.29 | 213894_at |
| THSD7A | 4.29 | 214920_at |
| THSD7A | 3.73 | 230008_at |
| MET | 2.64 | 213816_s_at |
| RAB31 | 2.46 | 217763_s_at |
| RAB31 | 2.30 | 217764_s_at |
| FAM126A | 2.30 | 223625_at |
| PHC1 | 2.14 | 218338_at |
| CHML | 2.00 | 226350_at |
| FAM126A | 2.00 | 227239_at |
| ST8SIA4 | 2.00 | 242943_at |
| CAV1 | 1.62 | 212097_at |

As shown in Table 11, the expression level difference between efficacy and non-efficacy is listed in order of THSD7A>MET>RAB31>FAM126A>PHC1>CHML>ST8SIA4>CAV1.

The 8 genes were selected as biomarkers for determining the efficacy of anti-c-Met antibody.

Example 2

Selection of Reference Markers

Using a total of 120 lung cancer adenocarcinoma microarray data (public DB—GEO: gene expression omnibus; http://www.ncbi.nlm.nih.gov/geo/), genes having low expression level variations between cells were selected.

For NSCLC tumor driven total RNA obtained from the GEO, log2(int) value for each probe was measured using affymetrix U133 plus2.0 microarray raw data (cell file), and genes having low coefficient of variation (CV) between the above 120 samples were listed. Then, genes having similar distribution of log2(int) values to that of target genes (the 8 species biomarkers selected in Example 1) were selected. The used primers are summarized in Table 12:

TABLE 12

| Gene | Sense Primer | Position | Tm | Anti-sense Primer | Position | Tm |
|---|---|---|---|---|---|---|
| RPL23A | GAGAGAAGAAGGCATATG (SEQ ID NO: 286) | 419 | 57.9 | TGGACTCAGTTTAGATGA (SEQ ID NO: 287) | 505 | 58.2 |
| TPT1 | GGCAATTATTTTGGATCTATC (SEQ ID NO: 288) | 620 | 58.7 | CAGTCCCATTTGTCTTAA (SEQ ID NO: 289) | 707 | 57.9 |
| EEF1A1 | CAGGACACAGAGACTTTA (SEQ ID NO: 290) | 341 | 59.3 | CAGCTTCAAATTCACCAA (SEQ ID NO: 291) | 439 | 59.6 |
| SRSF3 | CGAGAGCTAGATGGAAGA (SEQ ID NO: 292) | 361 | 61.3 | GGCCACGATTTCTACTTC (SEQ ID NO: 293) | 445 | 61.6 |
| TUT1 | GGTGTATCGAGTCCAAAC (SEQ ID NO: 294) | 1214 | 61.2 | CAGGAAACGGGAGTTATG (SEQ ID NO: 295) | 1340 | 61.2 |
| HNRNPC | CAAGCAGTAGAGATGAAG (SEQ ID NO: 296) | 914 | 58.2 | CTCCATCTTCACATTAGTC (SEQ ID NO: 297) | 1000 | 58.5 |
| HUWE1 | CAAGGTCTAATCATGCTG (SEQ ID NO: 298) | 2499 | 58.9 | CTGCTGGGTAGAATTAAAG (SEQ ID NO: 299) | 2590 | 59.1 |
| WDR90 | CTCTGGAGACAAGGATGG (SEQ ID NO: 300) | 4677 | 62.6 | GACACAGATGGTAGAGATTG (SEQ ID NO: 301) | 4782 | 61.3 |
| MATR3 | GGTGAGAAAGACACAAAG (SEQ ID NO: 302) | 2681 | 59.3 | CTGCTTCTTCTTCATCTAC (SEQ ID NO: 303) | 2774 | 58.8 |
| SMARCA4 | GTACCTCATGGAGCACAA (SEQ ID NO: 304) | 2456 | 62.9 | CCTTGTAAGACACCTTCAC (SEQ ID NO: 305) | 2580 | 61.6 |

Figure 2A:
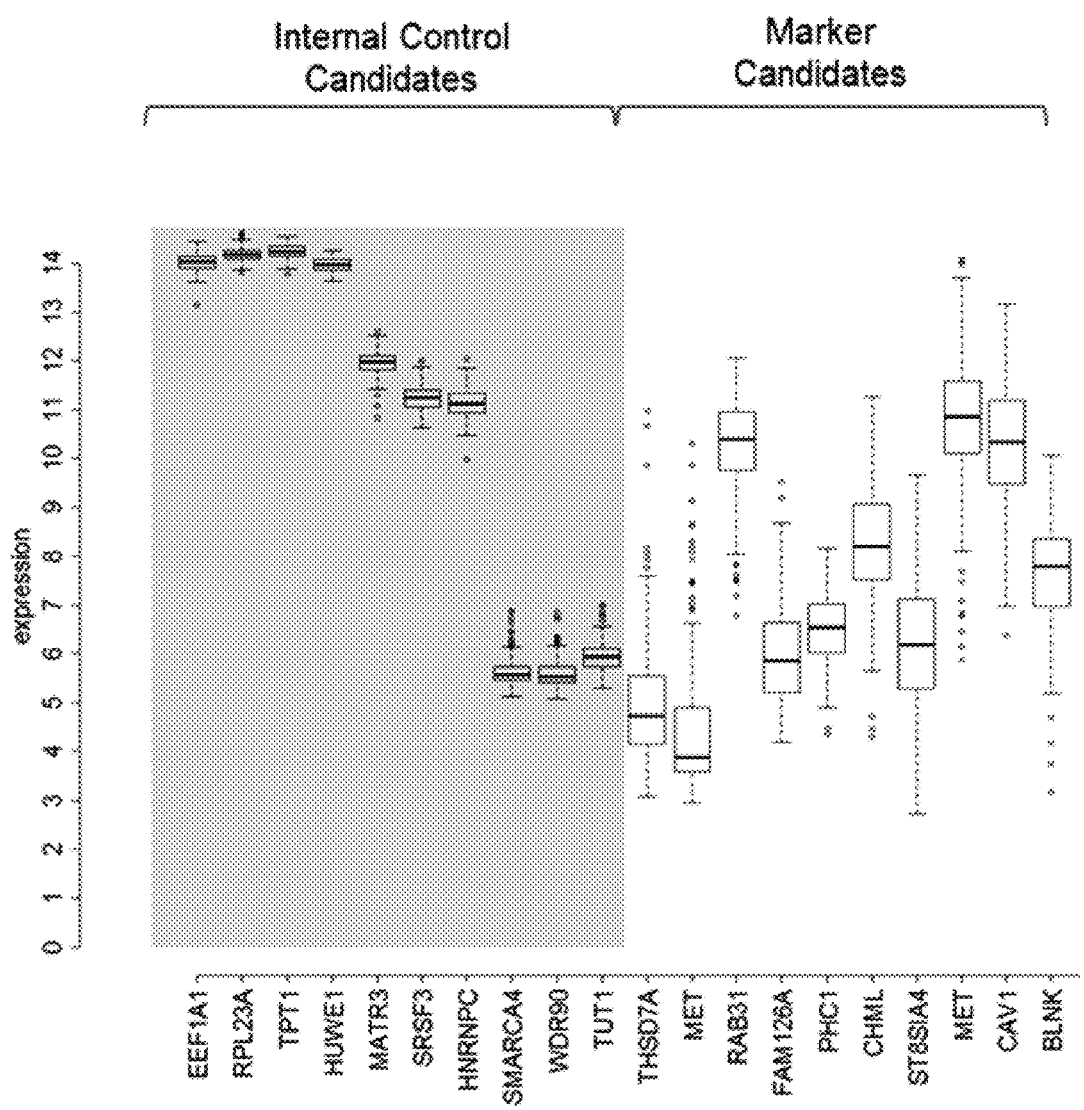
FIG. 2A is a graph showing the expression level of reference markers (control genes) and biomarkers (marker candidates).
Figure 2B:
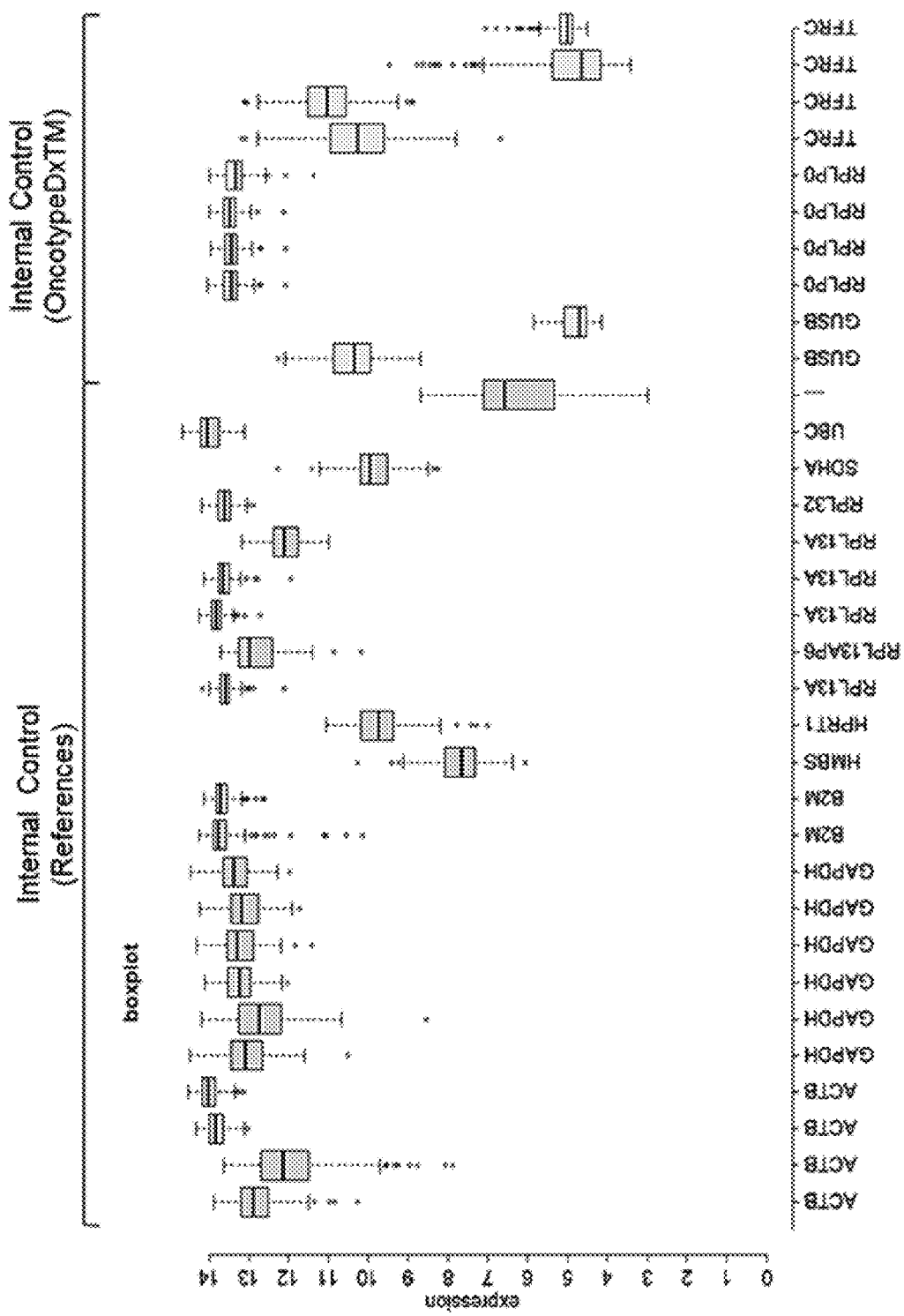
FIG. 2B is a graph showing the expression level of internal reference markers (control genes).

The obtained results are shown in FIGS. 2A and 2B. As shown in FIG. 2A, 10 genes, which have low gene expression variation, i.e., EEF1A1, RPL23A, TPT1, HUWE1, MATR3, SRSF3, HNRNPC, SMARCA4, WDR90, and TUT1, were selected as reference markers.

Variance and classification performance difference of the selected reference markers was measured, compared to pre-existing control genes (Oncotype DX™; see FIG. 2B).

The probes and primers used for the selected 10 species of reference markers are summarized in Tables 13 and 14:

TABLE 13

| Gene | robe Sequence (5'-3') | Position | Tm |
|---|---|---|---|
| RPL23A | ACTGGCTCCTGATTACGATGCTT (SEQ ID NO: 260) | 441 | 69.1 |
| TPT1 | CATAACTGGCTTCTGCTTGTCATCC (SEQ ID NO: 261) | 650 | 69 |
| EEF1A1 | CCAGCAGCAACAATCAGGACAG (SEQ ID NO: 262) | 419 | 69.1 |
| SRSF3 | TTCCACTCTTACACGGCAGC (SEQ ID NO: 263) | 408 | 67.6 |
| TUT1 | CCTGTGGTCAAGTTCTGTCATCG (SEQ ID NO: 264) | 1251 | 68.3 |
| HNRNPC | CTGCTGCTCTGCTCCTCTTCT (SEQ ID NO: 265) | 963 | 69.1 |
| HUWE1 | TCCTCTTCCTCCTCATCCTCACT (SEQ ID NO: 266) | 2553 | 69 |
| WDR90 | TGGTCACTCAGCACACGGAA (SEQ ID NO: 267) | 4751 | 69.1 |
| MATR3 | TGACCAGACAGAGCAGGAACC (SEQ ID NO: 268) | 2701 | 69 |
| SMARCA4 | CCTTCCTCATCATCGTGCCTCT (SEQ ID NO: 269) | 2488 | 69 |

TABLE 14

| Gene | Sense Primer | Position | Tm | Anti-sense Primer | Position | Tm |
|---|---|---|---|---|---|---|
| RPL23A | GAGAGAAGAAGGCATATG (SEQ ID NO: 286) | 419 | 57.9 | TGGACTCAGTTTAGATGA (SEQ ID NO: 287) | 505 | 58.2 |
| TPT1 | GGCAATTATTTTGGATCTATC (SEQ ID NO: 288) | 620 | 58.7 | CAGTCCCATTTGTCTTAA (SEQ ID NO: 289) | 707 | 57.9 |
| EEF1A1 | CAGGACACAGAGACTTTA (SEQ ID NO: 290) | 341 | 59.3 | CAGCTTCAAATTCACCAA (SEQ ID NO: 291) | 439 | 59.6 |
| SRSF3 | CGAGAGCTAGATGGAAGA (SEQ ID NO: 292) | 361 | 61.3 | GGCCACGATTTCTACTTC (SEQ ID NO: 293) | 445 | 61.6 |
| TUT1 | GGTGTATCGAGTCCAAAC (SEQ ID NO: 294) | 1214 | 61.2 | CAGGAAACGGGAGTTATG (SEQ ID NO: 295) | 1340 | 61.2 |
| HNRNPC | CAAGCAGTAGAGATGAAG (SEQ ID NO: 296) | 914 | 58.2 | CTCCATCTTCACATTAGTC (SEQ ID NO: 297) | 1000 | 58.5 |
| HUWE1 | CAAGGTCTAATCATGCTG (SEQ ID NO: 298) | 2499 | 58.9 | CTGCTGGGTAGAATTAAAG (SEQ ID NO: 299) | 2590 | 59.1 |
| WDR90 | CTCTGGAGACAAGGATGG (SEQ ID NO: 300) | 4677 | 62.6 | GACACAGATGGTAGAGATTG (SEQ ID NO: 301) | 4782 | 61.3 |
| MATR3 | GGTGAGAAAGACACAAAG (SEQ ID NO: 302) | 2681 | 59.3 | CTGCTTCTTCTTCATCTAC (SEQ ID NO: 303) | 2774 | 58.8 |
| SMARCA4 | GTACCTCATGGAGCACAA (SEQ ID NO: 304) | 2456 | 62.9 | CCTTGTAAGACACCTTCAC (SEQ ID NO: 305) | 2580 | 61.6 |

Using the 14 NSCLC mRNA samples prepared in Reference Example 2 and the method described above, variances of CV (Coefficient of Variation) values of the selected 10 species of reference markers to control genes were measured.

Figure 3A:
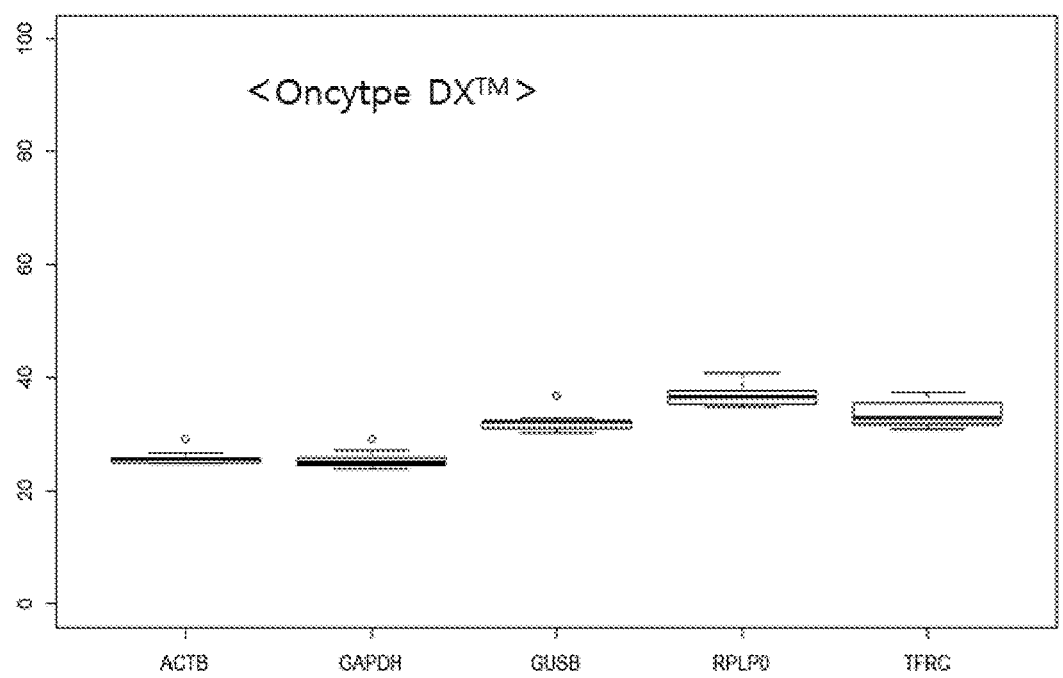
FIG. 3A is a graph showing the expression level of internal reference markers (control genes) measured using particular primers.
Figure 3B:
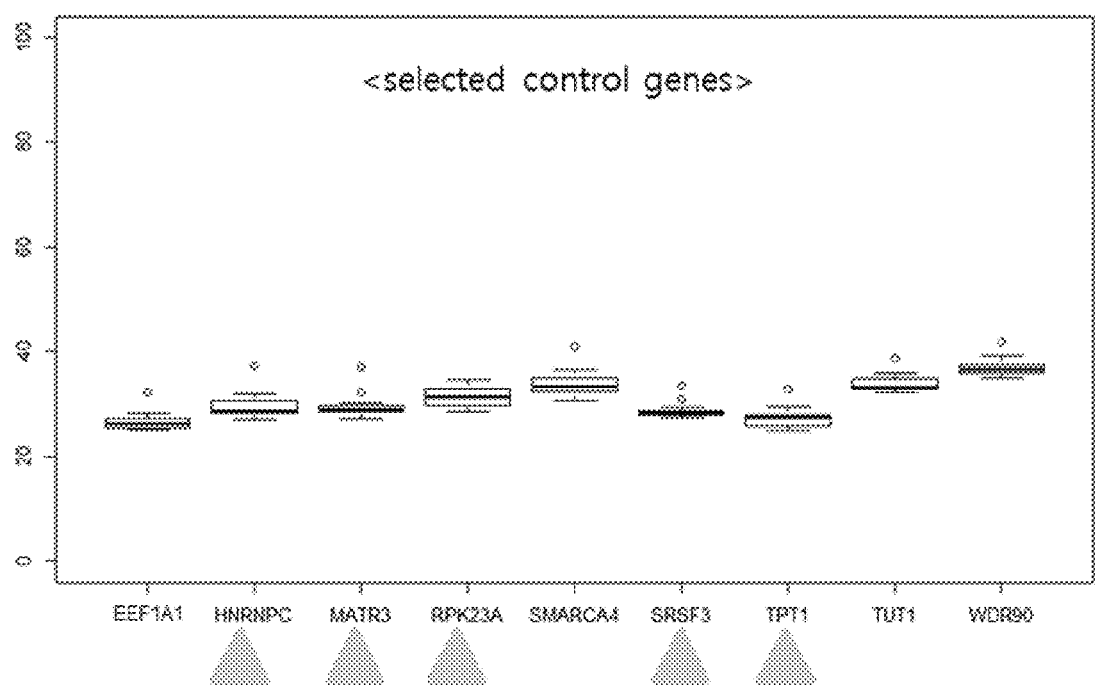
FIG. 3B is a graph showing the expression level of the selected reference markers (control genes) measured using particular primers.

The obtained results are shown in FIGS. 3A (control gene) and 3B (selected reference markers). As shown in FIGS. 3A and 3B, the average CV value of the selected 10 reference markers is 11.770, which is considerably decreased compared to that of pre-existing control genes (Oncotype DX™) (average CV=15.40335). Among the 10 reference markers, 5 genes, RPL23A, TPT1, MATR3, SRSF3, and HNRNPC, exhibit particularly low gene expression variation (average CV value of the 5 genes=8.39).

Example 3

Selection of an Efficacy Group of Anti-c-Met Antibody Using the Selected Biomarkers and Reference Markers The selected biomarkers and reference markers were applied to the mouse xenograft models, and the efficacy/non-efficacy group selection accuracy of the markers was examined.

For this, the total RNA extracted from the tumor tissue of the mouse xenograft model was subjected to PCR using probes of Table 15 and primers of Table 16 under the conditions of Table 17, Ct values of the 8 biomarkers and 5 reference markers (TPT1, EEF1M, TUT1, MATR3, and SMARCA4) were obtained.

TABLE 15

| Gene | Probe Sequence (5'-3') | Position | Tm |
|---|---|---|---|
| THSD7A | CCTCTTGAACTTGCGTGCCTG (SEQ ID NO: 109) | 2.053 | 69.1 |
| MET | CTTCACTTCGCAGGCAGATTCC (SEQ ID NO: 143) | 3.692 | 68.8 |
| RAB31 | ATACGCTGAATCCATAGGTGCCA (SEQ ID NO: 155) | 583 | 69 |
| FAM126A | TCTCTGCTGACCTGATTGATGCT (SEQ ID NO: 178) | 1.785 | 68.8 |
| PHC1 | ACCTCCTCACCTGTTGTAGCC (SEQ ID NO: 201) | 1.987 | 68.8 |
| ST8SIA4 | ACTGCTCTTGACCACTGACACA (SEQ ID NO: 236) | 631 | 69 |
| CHML | CCTCTGGCTGCTTATCATCACC (SEQ ID NO: 213) | 2.043 | 67.9 |
| CAV1 | TAGATAACAAGACCTCAGTGCCTTCC (SEQ ID NO: 248) | 1.453 | 68.9 |
| RPL23A | ACTGGCTCCTGATTACGATGCTT (SEQ ID NO: 260) | 441 | 69.1 |
| TPT1 | CATAACTGGCTTCTGCTTGTCATCC (SEQ ID NO: 261) | 650 | 69 |
| EEF1A1 | CCAGCAGCAACAATCAGGACAG (SEQ ID NO: 262) | 419 | 69.1 |
| SRSF3 | TTCCACTCTTACACGGCAGC (SEQ ID NO: 263) | 408 | 67.6 |
| TUT1 | CCTGTGGTCAAGTTCTGTCATCG (SEQ ID NO: 264) | 1251 | 68.3 |
| HNRNPC | CTGCTGCTCTGCTCCTCTTCT (SEQ ID NO: 265) | 963 | 69.1 |

TABLE 15-continued

| Gene | Probe Sequence (5'-3') | Position | Tm |
| --- | --- | --- | --- |
| HUWE1 | TCCTCTTCCTCCTCATCCTCACT (SEQ ID NO: 266) | 2553 | 69 |
| WDR90 | TGGTCACTCAGCACACGGAA (SEQ ID NO: 267) | 4751 | 69.1 |
| MATR3 | TGACCAGACAGAGCAGGAACC (SEQ ID NO: 268) | 2701 | 69 |
| SMARCA4 | CCTTCCTCATCATCGTGCCTCT (SEQ ID NO: 269) | 2488 | 69 |

TABLE 16

| Gene | Sense Primer | Position | Tm | Anti-sense Primer | Position | Tm |
| --- | --- | --- | --- | --- | --- | --- |
| THSD7A | GCCTGTTATGACTGGAAA (SEQ ID NO: 270) | 1.966 | 60.7 | CTGTCAACTTCTTCTCCA (SEQ ID NO: 271) | 2.090 | 59.9 |
| MET | CCTTGAACAGAATCACTG (SEQ ID NO: 272) | 3.573 | 59 | CCATGTTTCATGTATGGTA (SEQ ID NO: 273) | 3.729 | 58.4 |
| FAM126A | GCTTGTAGTCTCCAAGAA (SEQ ID NO: 274) | 1.702 | 60 | GGACAGAGTAATGCTAATAC (SEQ ID NO: 275) | 1.812 | 58.9 |
| PHC1 | GACAGCACATGTGGTAAA (SEQ ID NO: 276) | 1.956 | 61.4 | CACAGACTGCATATAGAAGG (SEQ ID NO: 277) | 2.040 | 61.4 |
| RAB31 | CTCAGATATTAGGGAGGTTC (SEQ ID NO: 278) | 544 | 60.2 | GCTGATTCCTTGAAAGAG (SEQ ID NO: 279) | 667 | 59.1 |
| ST8SIA4 | GCACAATGTAGAAGGTTG (SEQ ID NO: 280) | 523 | 59.8 | CAAGCACATAGTGTATGAC (SEQ ID NO: 281) | 665 | 59.5 |
| CHML | CTCCAAATCCAGAAGACA (SEQ ID NO: 282) | 1.993 | 60 | GGCCATTACTACATTATTGG (SEQ ID NO: 283) | 2.072 | 59.9 |
| CAV1 | CTGTGCCTGAATATTTGTTA (SEQ ID NO: 284) | 1.431 | 59.7 | CTGAGTTAGACCCTATTTGA (SEQ ID NO: 285) | 1.518 | 59.9 |
| RPL23A | GAGAGAAGAAGGCATATG (SEQ ID NO: 286) | 419 | 57.9 | TGGACTCAGTTTAGATGA (SEQ ID NO: 287) | 505 | 58.2 |
| TPT1 | GGCAATTATTTTGGATCTATC (SEQ ID NO: 288) | 620 | 58.7 | CAGTCCCATTTGTCTTAA (SEQ ID NO: 289) | 707 | 57.9 |
| EEF1A1 | CAGGACACAGAGACTTTA (SEQ ID NO: 290) | 341 | 59.3 | CAGCTTCAAATTCACCAA (SEQ ID NO: 291) | 439 | 59.6 |
| SRSF3 | CGAGAGCTAGATGGAAGA (SEQ ID NO: 292) | 361 | 61.3 | GGCCACGATTTCTACTTC (SEQ ID NO: 293) | 445 | 61.6 |
| TUT1 | GGTGTATCGAGTCCAAAC (SEQ ID NO: 294) | 1214 | 61.2 | CAGGAAACGGGAGTTATG (SEQ ID NO: 295) | 1340 | 61.2 |
| HNRNPC | CAAGCAGTAGAGATGAAG (SEQ ID NO: 296) | 914 | 58.2 | CTCCATCTTCACATTAGTC (SEQ ID NO: 297) | 1000 | 58.5 |
| HUWE1 | CAAGGTCTAATCATGCTG (SEQ ID NO: 298) | 2499 | 58.9 | CTGCTGGGTAGAATTAAAG (SEQ ID NO: 299) | 2590 | 59.1 |
| WDR90 | CTCTGGAGACAAGGATGG (SEQ ID NO: 300) | 4677 | 62.6 | GACACAGATGGTAGAGATTG (SEQ ID NO: 301) | 4782 | 61.3 |
| MATR3 | GGTGAGAAAGACACAAAG (SEQ ID NO: 302) | 2681 | 59.3 | CTGCTTCTTCTTCATCTAC (SEQ ID NO: 303) | 2774 | 58.8 |
| SMARCA4 | GTACCTCATGGAGCACAA (SEQ ID NO: 304) | 2456 | 62.9 | CCTTGTAAGACACCTTCAC (SEQ ID NO: 305) | 2580 | 61.6 |

TABLE 17

| Setup | | |
|---|---|---|
| Detection Format | Block Type | Reaction Volume |
| Mono Color Hydrolysis Probes or Multi Color Hydrolysis Probes | 96 | 10-100 μl |

| Programs | | |
|---|---|---|
| Program Name | Cycles | Analysis Mode |
| Reverse Transcription | 1 | None |
| Denaturation | 1 | None |
| Amplification | 45 [1)] | Quantification |
| Cooling | 1 | None |

| Temperature Targets | | | | |
|---|---|---|---|---|
| Target (° C.) | Acquisition Mode | Hold (hh:mm:ss) | Ramp Rate (° C./s) | Acquisitions (per ° C.) |
| Reverse Transcription | | | | |
| 63 [2)] | None | 00:03:00 [3)] | 4.4 | — |
| Denaturation | | | | |
| 95 | None | 00:00:30 | 4.4 | — |
| Amplification | | | | |
| 95 | None | 00:00:10-00:00:15 | 4.4 | — |
| 60 [4)] | None | 00:00:30-00:00:60 | 2.2 [5)] | — |
| 72 | Single | 00:00:01 | 4.4 | — |
| Cooling | | | | |
| 40 | None | 00:00:10 | 2.2 [5)] | — |

The determination of an efficacy or non-efficacy group was carried out according to Table 18:

TABLE 18

| Gene | Standard Reference Value | classifier | Determination |
|---|---|---|---|
| CAV1 | 2.4641667 | up | efficacy |
| CMHL | 5.0303333 | down | efficacy |
| FAM126A | 7.0321667 | up | efficacy |
| MET | 4.9 | up | efficacy |
| PHC1 | 8.4125 | down | efficacy |
| RAB31 | 4.8678333 | up | efficacy |
| ST8SIA4 | 12.038833 | up | efficacy |
| THSD7A | 8.3295 | up | efficacy |

In Table 18:

"Standard Reference Value" for CAV1, FAM126A, MET, RAB31, ST8SIA4, and THSD7A, Value=[Min(efficacy value (ΔCt))+Max(non-efficacy value (ΔCt))]/2;

"Standard Reference Value" for CMHL and PHC1=[Min (non-efficacy value (ΔCt))+Max(efficacy value (ΔCt))]/2;

ΔCt: Average Ct value of 5 reference markers (TPT1, EEF1M, TUT1, MATR3, and SMARCA4)–Ct value of each biomarker;

Min(efficacy value (ΔCt)): minimum ΔCt of efficacy group;

Max(non-efficacy value (ΔCt)): maximum ΔCt of non-efficacy group;

Min(non-efficacy value (ΔCt)): minimum ΔCt of non-efficacy group; and

Max(efficacy value (ΔCt)): maximum ΔCt of efficacy group)

ΔCt value calculated for each biomarker was compared with the values of Table 18. In case of CAV1, FAM126A, MET, RAB31, RAB31, ST8SIA4, and THSD7A, when the ΔCt value for individual biomarker is higher than the value of Table 18, the sample is determined as an efficacy group, and in case of CMHL and PHC1, when ΔCt value for individual biomarker is lower than the value of Table 18, the sample is determined as an efficacy group.

The accuracy of determination of efficacy/non-efficacy group for the 14 mouse xenograft model of Reference Example 2 and ΔFold value are shown in Table 19.

TABLE 19

| ID | Accuracy | Δ Fold |
|---|---|---|
| THSD7A | 0.86 | 0.49 |
| MET | 0.86 | 0.79 |
| RAB31 | 0.79 | 0.53 |
| FAM126A | 0.64 | 0.82 |
| PHC1 | 0.93 | 0.33 |
| CHML | 0.93 | 0.27 |
| ST8SIA4 | 0.93 | 1.36 |
| CAV1 | 0.79 | 1.96 |

(Accuracy: accuracy of predicting efficacy of antibody obtained using each biomarker, as the value is closer to 1 (corresponding to 100%), accuracy is higher, and calculated by the following formula:

Accuracy={$(TP+TN)/14$}

(TP: the number of samples showing positive results in efficacy prediction using the biomarker as well as in actual experiment (see Table 9) with treatment of L3-1Y/IgG2)

(TN: the number of samples showing negative results from efficacy prediction using the biomarker as well as from actual experiment (see Table 9) with treatment of L3-1Y/IgG2);

ΔFold: Difference of delta Ct (control (reference marker) gene Ct (if the number of reference marker is two or more, it means "average Ct value of reference markers")–target (biomarker) gene Ct) between efficacy and non-efficacy groups, indicating mRNA expression range capable of distinguishing between efficacy and non-efficacy group).

As shown in Table 19, the selected biomarker and reference markers can achieve highly accurate determination of efficacy and non-efficacy group of an anti-c-Met antibody, with accuracy of at least about 60%, for example at least about 80%.

It should be understood that the exemplary embodiments described herein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising,"

"having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of selecting a subject for administration of an anti-c-Met antibody or antigen-binding fragment thereof, the method comprising:

selecting for administration of an anti-c-Met antibody or antigen-binding antibody fragment a subject in which the expression level of one or more biomarkers including THSD7A is higher than the expression level of one or more reference markers including MATR3, or higher than the expression level of the one or more biomarkers in a reference sample on which the anti-c-Met antibody or antigen-binding fragment thereof has no effect or having a resistance to an anti-c-Met antibody or antigen-binding fragment thereof;

wherein selecting the subject comprises:

measuring the expression level of the one or more biomarkers in a biological cancer cell or tissue sample from a human subject; and comparing the expression level of the one or more biomarkers to the expression level of the one or more reference markers, or to the expression level of the one or more biomarkers in a reference sample; and administering the anti-c-Met antibody or antigen-binding fragment thereof to the selected subject, wherein the anti-c-Met antibody or antigen-binding fragment thereof specifically binds to an epitope which has 5 to 19 contiguous amino acids selected from the amino acid sequence of SEQ ID NO: 71, wherein the epitope comprises SEQ ID NO: 73; and the anti-c-Met antibody or antigen-binding fragment thereof comprises at least one heavy chain complementarity determining region (CDR) selected from a group consisting of (a) a CDR-H1 comprising SEQ ID NO: 4; (b) a CDR-H2 comprising SEQ ID NO: 5, SEQ ID NO: 2, or an amino acid sequence comprising 8-19 consecutive amino acids of SEQ ID NO: 2 including the $3^{rd}$ to $10^{th}$ positions of SEQ ID NO: 2; and (c) a CDR-H3 comprising SEQ ID NO: 6, SEQ ID NO: 85, or an amino acid sequence comprising 6-13 consecutive amino acids of SEQ ID NO: 85 including the $1^{st}$ to $6^{th}$ positions of SEQ ID NO: 85; and at least one light chain complementarity determining region selected from the group consisting of (a) a CDR-L1 comprising SEQ ID NO: 7, (b) a CDR-L2 comprising SEQ ID NO: 8, and (c) a CDR-L3comprising SEQ ID NO: 9, SEQ ID NO: 15, SEQ ID NO: 86, or an amino acid sequence comprising 9-17 consecutive amino acids of SEQ ID NO: 89 including the $1^{st}$ to $9^{th}$ positions of SEQ ID NO: 89; or a combination thereof.

2. The method of claim 1, wherein the one or more biomarkers further comprises MET and the subject has THSD7A and MET levels that are higher than that of the one or more reference markers or the reference sample.

3. The method of claim 1, wherein the one or more biomarkers further comprises RAB31 and the subject has THSD7A and RAB31 levels that are higher than that of the one or more reference markers or the reference sample.

4. The method of claim 1, wherein the one or more biomarkers further comprises FAM126A and the subject has THSD7A and FAM126A levels that are higher than that of the one or more reference markers or the reference sample.

5. The method of claim 1, wherein the expression level of the one or more biomarkers or one or more reference markers is determined using at least one probe comprising SEQ ID NO: 109 or 268.

6. The method of claim 1, wherein the expression level of the one or more biomarkers or one or more reference markers is determined using at least one primer comprising SEQ ID NOS: 270, 271, 302 or 303.

7. The method of claim 1, wherein the one or more biomarkers comprises THSD7A, MET, and RAB31, and the subject has THSD7A, MET, and RAB31 levels that are higher than that of the one or more reference markers or the reference sample.

8. The method of claim 1, wherein the one or more biomarkers comprises THSD7A, MET, RAB31 and FAM126A, and the subject has THSD7A, MET, RAB31, and FAM126A levels that are higher than that of the one or more reference markers or the reference sample.

9. The method of claim 1, wherein the one or more biomarkers comprises THSD7A, RAB31, FAM126A, PHC1, CHML, ST8SIA4, and CAV1; and the subject has THSD7A, RAB31, FAM126A, and ST8SIA4 levels that are higher than that of the one or more reference markers or the reference sample, and PHC1 and CHML levels that are lower than that of the one or more reference markers or the reference sample.

10. The method of claim 1, wherein the one or more reference markers further comprises EEF1A1.

11. The method of claim 1, wherein the one or more reference markers comprises RPL23A, TPT1, MATR3, SRSF3, and HNRNPC.

12. The method of claim 1, wherein the one or more reference markers comprises TPT1, EEF1M, TUT1, MATR3, and SMARCA4.

13. A method of selecting and treating a human subject with a c-Met inhibitor, the method comprising:

comparing the expression level of one or more biomarkers in a biological cancer cell or tissue sample from a human subject to the expression level of one or more reference markers, or to the expression level of the one or more biomarkers in a reference sample, wherein the one or more biomarkers includes THSD7A; the one or more reference markers includes MATR3; and the reference sample is a sample upon which the anti-c-Met antibody or antigen-binding fragment thereof has no effect or is resistant to treatment with an anti-c-Met antibody or antigen-binding fragment thereof;

and selecting a subject with a THSD7A expression level that is higher than that of one or more reference markers or higher than the THSD7A expression level in the reference sample, and administering to the selected subject an anti-c-Met antibody or antigen-binding fragment thereof;

wherein the anti-c-Met antibody or antigen-binding fragment thereof specifically binds to an epitope which has 5 to 19 contiguous amino acids selected from the amino acid sequence of SEQ ID NO: 71, wherein the epitope comprises SEQ ID NO: 73; and wherein the anti-c-Met antibody or antigen-binding fragment thereof comprises at least one heavy chain complementarity determining region (CDR) selected from a group consisting of (a) a CDR-H1 comprising SEQ ID NO: 4; (b) a CDR-H2 comprising SEQ ID NO: 5, SEQ ID NO: 2, or an amino acid sequence comprising 8-19 consecutive amino acids of SEQ ID NO: 2 including the $3^{rd}$ to $10^{th}$ positions of SEQ ID NO: 2; and (c) a CDR-H3 comprising SEQ ID NO: 6, SEQ ID NO: 85, or an amino acid sequence comprising 6-13 consecutive amino acids of SEQ ID NO: 85 including the $1^{st}$ to $6^{th}$ positions of SEQ ID NO: 85; and at least one light chain complementarity determining region selected from the group consisting of (a) a CDR-L1 comprising SEQ ID NO: 7, (b) a CDR-L2comprising SEQ ID NO: 8, and (c) a CDR-L3 comprising SEQ ID NO: 9, SEQ ID NO: 15, SEQ ID NO: 86, or an amino acid sequence comprising 9-17 consecutive amino acids of SEQ ID NO: 89 including the $1^{st}$ to $9^{th}$ positions of SEQ ID NO: 89; or a combination thereof.

14. The method of claim 13, wherein the one or more biomarkers include THSD7A and MET, and the method comprises selecting a subject with THSD7A and MET expression levels that are higher than that of the one or more reference markers or the reference sample, and administering to the selected subject an anti-c-Met antibody or antigen-binding fragment thereof.

15. The method of claim 13, wherein the one or more biomarkers include THSD7A and RAB31, and the method comprises selecting a subject with THSD7A and RAB31 levels that are higher than that of the one or more reference markers or the reference sample, and administering to the selected subject an anti-c-Met antibody or antigen-binding fragment thereof.

16. The method of claim 13, wherein the one or more biomarkers include THSD7A and FAM126A, and the method comprises selecting a subject with THSD7A and FAM126A levels that are higher than that of the one or more reference markers or the reference sample, and administering to the selected subject an anti-c-Met antibody or antigen-binding fragment thereof.

17. The method of claim 13, wherein the one or more biomarkers include THSD7A, MET and RAB31, and the method comprises selecting a subject with THSD7A, MET, and RAB31 levels that are higher than that of the one or more reference markers or the reference sample, and administering to the selected subject an anti-c-Met antibody or antigen-binding fragment thereof.

18. The method of claim 13, wherein the one or more biomarkers include THSD7A, MET, RAB31 and FAM126A, and the method comprises selecting a subject with THSD7A, MET, RAB31, and FAM126A levels that are higher than that of the one or more reference markers or reference sample, and administering to the selected subject an anti-c-Met antibody or antigen-binding fragment thereof.

19. The method of claim 13, wherein the one or more biomarkers include THSD7A, RAB31, FAM126A and ST8SIA4, and the method comprises selecting a subject with THSD7A, RAB31, FAM126A, and ST8SIA4 levels that are higher than that of the one or more reference markers or the reference sample, and PHC1 and CHML levels that are lower than that of the one or more reference markers or the reference sample, and administering to the selected subject an anti-c-Met antibody or antigen-binding fragment thereof.

20. The method of claim 13, wherein the one or more reference markers comprises MATR3 and EEF1A1.

21. The method of claim 13, wherein the one or more reference markers comprises RPL23A, TPT1, MATR3, SRSF3, and HNRNPC.

22. The method of claim 13, wherein the one or more reference markers comprises TPT1, EEF1M, TUT1, MATR3, and SMARCA4.

23. The method of claim 13, wherein the anti-c-Met antibody or antigen-binding fragment thereof comprises:
a heavy chain comprising:
(a) a CDR-H1 comprising SEQ ID NO: 4;
(b) a CDR-H2 comprising SEQ ID NO: 5, SEQ ID NO: 2, or an amino acid sequence comprising 8-19 consecutive amino acids of SEQ ID NO: 2 including the $3^{rd}$ to $10^{th}$ positions of SEQ ID NO: 2; and
(c) a CDR-H3 comprising SEQ ID NO: 6, SEQ ID NO: 85, or an amino acid sequence comprising 6-13 consecutive amino acids of SEQ ID NO: 85 including the $1^{st}$ to $6^{th}$ positions of SEQ ID NO: 85; and
a light chain comprising
(a) a CDR-L1 comprising SEQ ID NO: 7;
(b) a CDR-L2 comprising SEQ ID NO: 8; and
(c) a CDR-L3 comprising SEQ ID NO: 9, SEQ ID NO: 15, SEQ ID NO: 86, or an amino acid sequence comprising 9-17 consecutive amino acids of SEQ ID NO: 89 including the $1^{st}$ to $9^{th}$ positions of SEQ ID NO: 89.

24. The method of claim 1, wherein the anti-c-Met antibody or antigen-binding fragment thereof comprises:
a heavy chain comprising:
(a) a CDR-H1 comprising SEQ ID NO: 4;
(b) a CDR-H2 comprising SEQ ID NO: 5, SEQ ID NO: 2, or an amino acid sequence comprising 8-19 consecutive amino acids of SEQ ID NO: 2 including the $3^{rd}$ to $10^{th}$ positions of SEQ ID NO: 2; and
(c) a CDR-H3 comprising SEQ ID NO: 6, SEQ ID NO: 85, or an amino acid sequence comprising 6-13 consecutive amino acids of SEQ ID NO: 85 including the $1^{st}$ to $6^{th}$ positions of SEQ ID NO: 85; and
a light chain comprising
(a) a CDR-L1 comprising SEQ ID NO: 7;
(b) a CDR-L2 comprising SEQ ID NO: 8; and
(c) a CDR-L3 comprising SEQ ID NO: 9, SEQ ID NO: 15, SEQ ID NO: 86, or an amino acid sequence comprising 9-17 consecutive amino acids of SEQ ID NO: 89 including the $1^{st}$ to $9^{th}$ positions of SEQ ID NO: 89.

\* \* \* \* \*